US012629362B2

(12) United States Patent
Carew et al.

(10) Patent No.: US 12,629,362 B2
(45) Date of Patent: May 19, 2026

(54) SMALL MOLECULE INHIBITORS OF AUTOPHAGY AND HISTONE DEACTYLASES AND USES THEREOF

(71) Applicant: Arizona Board of Regents on Behalf of the University of Arizona, Tucson, AZ (US)

(72) Inventors: Jennifer S. Carew, Tucson, AZ (US); Steffan Nawrocki, Tucson, AZ (US); Wei Wang, Tucson, AZ (US)

(73) Assignee: Arizona Board of Regents on Behalf of the University of Arizona, Tucson, AZ (US)

( * ) Notice: Subject to any disclaimer, the term of this patent is extended or adjusted under 35 U.S.C. 154(b) by 787 days.

(21) Appl. No.: 17/773,405

(22) PCT Filed: Oct. 29, 2020

(86) PCT No.: PCT/US2020/057903

§ 371 (c)(1),
(2) Date: Apr. 29, 2022

(87) PCT Pub. No.: WO2021/087077

PCT Pub. Date: May 6, 2021

(65) Prior Publication Data

US 2023/0022696 A1 Jan. 26, 2023

Related U.S. Application Data

(60) Provisional application No. 63/075,045, filed on Sep. 4, 2020, provisional application No. 62/927,554, filed on Oct. 29, 2019.

(51) Int. Cl.

| | |
|---|---|
| ***C07D 335/18*** | (2006.01) |
| ***A61K 31/382*** | (2006.01) |
| ***A61K 31/4706*** | (2006.01) |
| ***A61K 31/675*** | (2006.01) |
| ***A61P 3/10*** | (2006.01) |
| ***A61P 9/00*** | (2006.01) |
| ***A61P 9/10*** | (2006.01) |
| ***A61P 9/12*** | (2006.01) |
| ***A61P 31/00*** | (2006.01) |
| ***A61P 31/04*** | (2006.01) |
| ***A61P 31/06*** | (2006.01) |
| ***A61P 31/12*** | (2006.01) |
| ***A61P 35/00*** | (2006.01) |
| ***C07D 215/42*** | (2006.01) |
| ***C07D 215/46*** | (2006.01) |
| ***C07D 401/12*** | (2006.01) |
| ***C07D 409/12*** | (2006.01) |
| ***C07D 417/12*** | (2006.01) |

(52) U.S. Cl.

CPC ........ *A61K 31/4706* (2013.01); *A61K 31/382* (2013.01); *A61K 31/675* (2013.01); *C07D 215/46* (2013.01); *C07D 335/18* (2013.01)

(58) Field of Classification Search

CPC .. C07D 335/18; C07D 215/42; C07D 401/12; C07D 409/12; C07D 417/12; A61K 31/4706; A61K 31/382; A61K 31/675; A61P 35/00; A61P 9/00; A61P 9/10; A61P 9/12; A61P 3/10; A61P 31/00; A61P 31/04; A61P 31/06; A61P 31/12

See application file for complete search history.

(56) References Cited

U.S. PATENT DOCUMENTS

| | | | | |
|---|---|---|---|---|
| 3,989,816 | A | 11/1976 | Rajadhyaksha | |
| 4,444,762 | A | 4/1984 | Rajadhyaksha | |
| 8,524,762 | B2 * | 9/2013 | Nawrocki ............ | A61K 31/427 514/437 |
| 9,000,031 | B2 * | 4/2015 | Nawrocki ............ | A61K 31/517 514/437 |
| 2008/0188462 | A1 * | 8/2008 | Peyton ................. | C07D 401/14 546/159 |
| 2010/0196502 | A1 | 8/2010 | Kozikowski et al. | |
| 2012/0028969 | A1 | 2/2012 | Barnes et al. | |
| 2017/0209441 | A1 | 7/2017 | Rawat et al. | |

FOREIGN PATENT DOCUMENTS

| | | | | |
|---|---|---|---|---|
| WO | WO-2011112623 A1 * | 9/2011 | ............. | A61K 31/00 |
| WO | WO-2016011022 A1 * | 1/2016 | ......... | A61K 31/4709 |

OTHER PUBLICATIONS

CAS Registry RN: 1348155-22-5 (Entered STN date: Dec. 4, 2011). (Year: 2011).*
CAS Registry RN: 774491-15-5 (Entered STN date: Nov. 3, 2004). (Year: 2004).*
CAS Registry RN: 501655-61-4 (Entered STN date: Apr. 4, 2003). (Year: 2003).*
Amaravadi R K, and Thompson C B. Clin Cancer Res. 2007; 13(24):7271-9.
Amaravadi R K, et al., Clin Cancer Res. 2011; 17(4):654-66.
Amaravadi R K, et al., J Clin Invest. 2007; 117(2):326-36.
Amaravadi R K., et al., J Clin Invest. 2008;118(12):3837-3840.
Carew J S, et al., Blood. 2007; 110(1): 313-322.
Codogno et al., Cell Metab 2010; 11: 449-51.
Degenhardt K, et al., Cancer Cell. 2006; 10(1):51-64.

(Continued)

*Primary Examiner* — Kamal A Saeed
*Assistant Examiner* — Sagar Patel
(74) *Attorney, Agent, or Firm* — Casimir Jones, S.C.; Robert A. Goetz

(57) ABSTRACT

This invention is in the field of medicinal chemistry. In particular, the invention relates to a new class of small-molecules having a quinoline or thioxanthenone (or similar) structure which function as autophagy inhibitors and/or histone deactylase inhibitors, and their use as therapeutics for the treatment of conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

12 Claims, 1 Drawing Sheet

(56) References Cited

OTHER PUBLICATIONS

Degtyarev M, et al., J Cell Biol. 2008; 183(1):101-16.
Fuchs Y, Steller H., Cell 2011; 147: 742-58.
Greenberg et al., Proc. Natl. Acad. Sci. USA, 92:3439-3443 (1995).
Hidvegi et al., Science 2010; 329: 229-32.
Lum J J, et al., Nat Rev Mol Cell Biol. 2005; 6(6):439-48.
Mahalingam D, et al., Autophagy. 2014; 10(8).
Pareek et al., Curr Med Res Opin 2014; 30: 1257-66.
Polin et al., Investig. New Drugs, 15:99-108 (1997).
Pub Chem CID 58476679; Aug. 19, 2012; p. 2.
Rebecca V W, et al., Pigment Cell Melanoma Res. 2014; 27(3):465-78.
Rosenfeld M R, et al., Autophagy. 2014; 10(8).
Rubinsztein et al., Cell 2011; 146: 682-95.
Thapalia et al., Int J Clin Exp Pathol. 2014; 7(12):8322-41.
Virgin H W, Levine B. Nat Immunol 2009; 10: 461-70.
International Search Report & Written Opinion; International filing date Oct. 29, 2020; Mailing date Mar. 30, 2021; 10 pages.

* cited by examiner

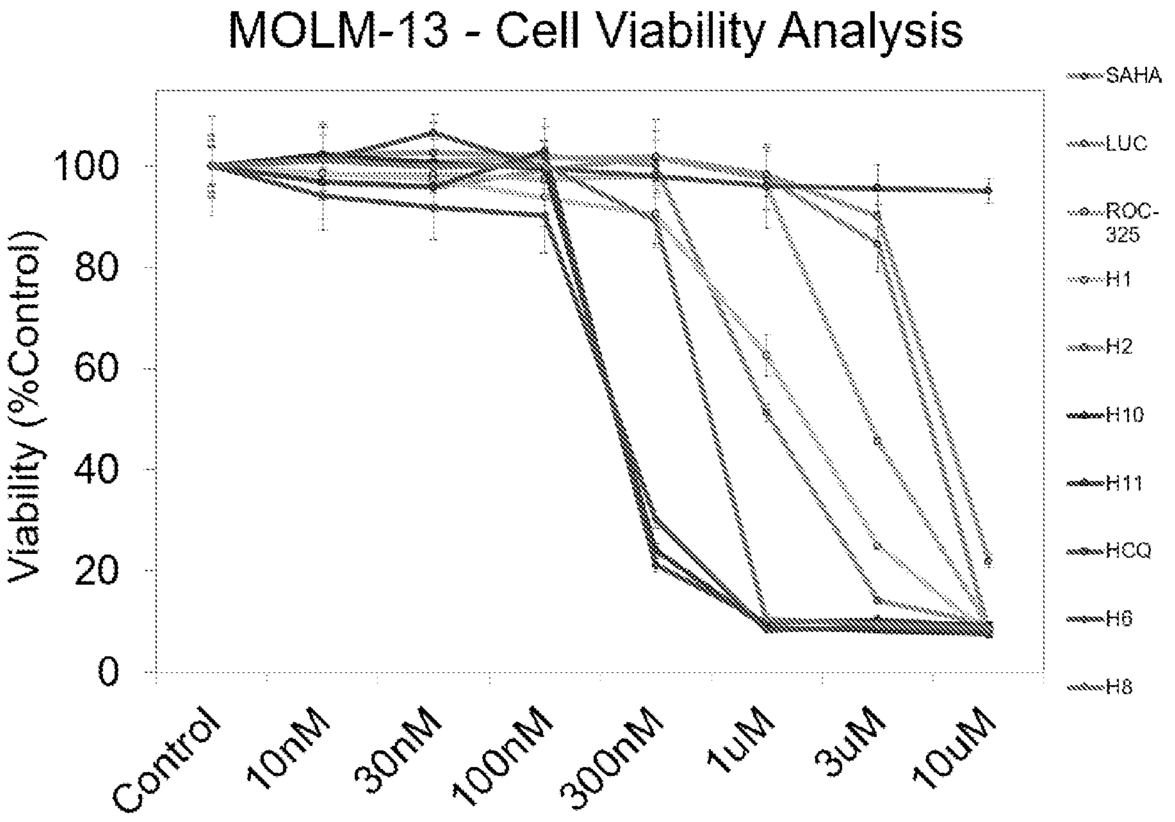
MOLM-13 - Cell Viability Analysis
Viability (%Control)
100
80
60
40
20
0
Control
10nM
30nM
100nM
300nM
1uM
3uM
10uM
SAHA
LUC
ROC-325
H1
H2
H10
H11
HCQ
H6
H8

SMALL MOLECULE INHIBITORS OF AUTOPHAGY AND HISTONE DEACTYLASES AND USES THEREOF

CROSS REFERENCE TO RELATED APPLICATIONS

This application is a U.S. 371 national phase entry of International Patent No. PCT/US2020/057903, filed Oct. 29, 2020 which claims priority to and the benefit of U.S. Provisional Application No. 62/927,554, filed Oct. 29, 2019 and U.S. Provisional Application No. 63/075,045, filed Sep. 4, 2020, which are incorporated herein by reference in their entireties.

FIELD OF THE INVENTION

This invention is in the field of medicinal chemistry. In particular, the invention relates to a new class of small-molecules having a quinoline or thioxanthenone (or similar) structure which function as autophagy inhibitors and/or histone deactylase inhibitors, and their use as therapeutics for the treatment of conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

INTRODUCTION

Autophagy consists of the sequestration of organelles and proteins in autophagic vesicles and degradation of this cargo through lysosomal fusion (see, Lum J J, et al., Nat Rev Mol Cell Biol. 2005; 6(6):439-48). Autophagy allows tumor cells to survive metabolic and therapeutic stresses (see, Amaravadi R K, and Thompson C B. Clin Cancer Res. 2007; 13(24):7271-9; Amaravadi R K, et al., J Clin Invest. 2007; 117(2):326-36; Degenhardt K, et al., Cancer Cell. 2006; 10(1):51-64; Amaravadi R K., et al., J Clin Invest. 2008; Carew J S, et al., Blood. 2007). Multiple publications indicate therapy-induced autophagy is a key resistance mechanism to many anti-cancer agents. Chloroquine (CQ) derivatives block autophagy by inhibiting the lysosome (see, Amaravadi R K, et al., J Clin Invest. 2007; 117(2):326-36; Carew J S, et al., Blood. 2007; Degtyarev M, et al., J Cell Biol. 2008; 183(1):101-16). Based on these findings, clinical trials combining cancer therapies with hydroxychloroquine (HCQ) have been launched. Results indicate these combinations have activity (see, Amaravadi R K, et al., Clin Cancer Res. 2011; 17(4):654-66; Rebecca V W, et al., Pigment Cell Melanoma Res. 2014; 27(3):465-78; Mahalingam D, et al., Autophagy. 2014; 10(8); Rangwala R, et al., Autophagy. 2014; 10(8); Rangwala R, et al., Autophagy. 2014; 10(8); Rosenfeld M R, et al., Autophagy. 2014; 10(8)), but it is still unclear if this activity is consistently due to the addition of HCQ. High micromolar concentrations of HCQ are required to inhibit autophagy. While there is some pharmacodynamic evidence of autophagy inhibition with HCQ in cancer patients, it is inconsistent because adequate concentrations are not achieved in all patients.

As such, there is an unmet need to develop more potent inhibitors of autophagy.

The present invention addresses this need.

SUMMARY OF THE INVENTION

Experiments conducted during the course of developing embodiments for the present invention designed, synthesized and biologically evaluated compounds having a quinoline or thioxanthenone (or similar) structure as autophagy inhibitors and/or histone deacetylase (HDAC) inhibitors, and their potential for use as therapeutics against conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, etc.).

Certain quinoline or thioxanthenone (or similar) compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, compounds encompassed within the following formulas are provided:

(Formula I)

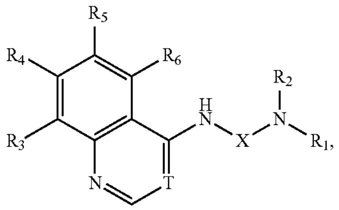

(Formula II)

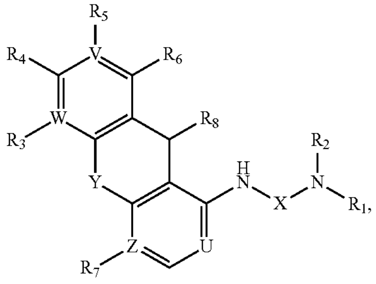

(Formula III)

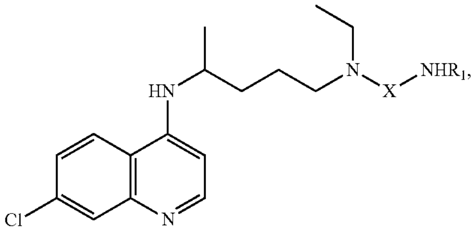

and (Formula IV)

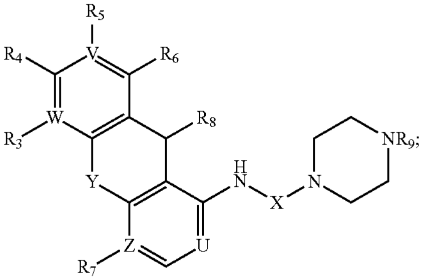

including pharmaceutically acceptable salts, solvates, and/or prodrugs thereof.

Formulas I, III, and III are not limited to a particular chemical moiety for T, U, V, W, X, Y, Z, $R_1$, $R_2$, $R_3$, $R_4$, $R_5$, $R_6$, $R_7$, $R_8$, and $R_9$. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular autophagy. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular HDAC activity. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular autophagy and cellular HDAC activity. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to act as an effective therapeutic for treating conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

Such embodiments are not limited to a particular definition for T.

In some embodiments, T is selected from Carbon and Nitrogen.

Such embodiments are not limited to a particular definition for U.

In some embodiments, U is selected from Carbon and Nitrogen.

Such embodiments are not limited to a particular definition for V.

In some embodiments, V is selected from Carbon and Nitrogen.

Such embodiments are not limited to a particular definition for W.

In some embodiments, W is selected from Carbon and Nitrogen.

Such embodiments are not limited to a particular definition for X.

In some embodiments, X is selected from

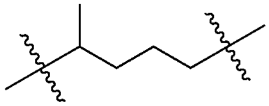 , 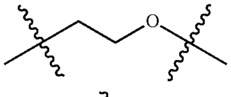 ,

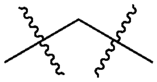 , 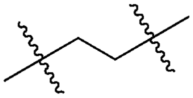 ,

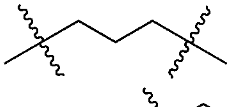 , 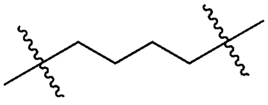 ,

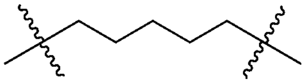 ,

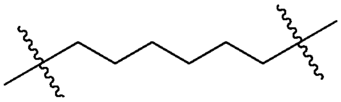 ,

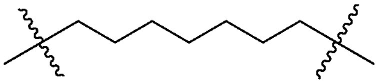 ,

-continued

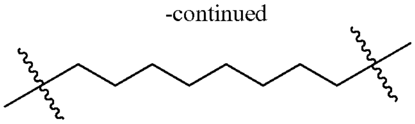 ,

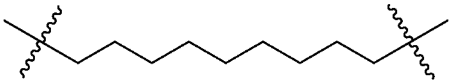 ,

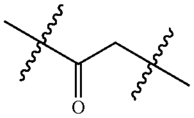 , 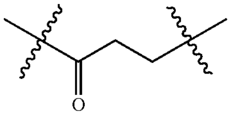 ,

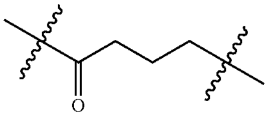 ,

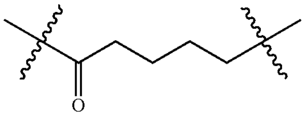 ,

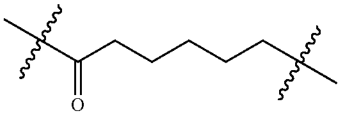 ,

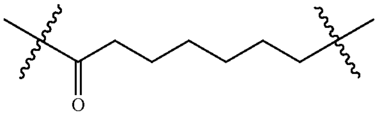 ,

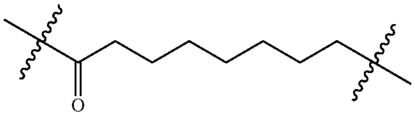 ,

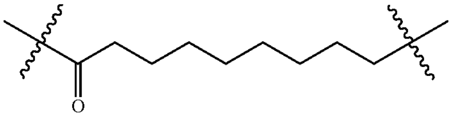 ,

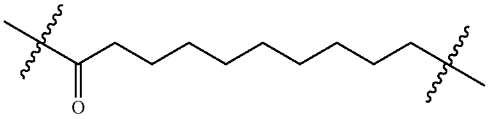 ,

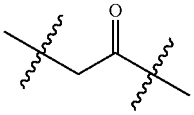 , 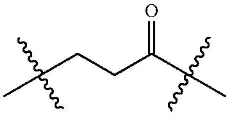 ,

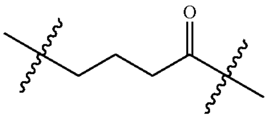 ,

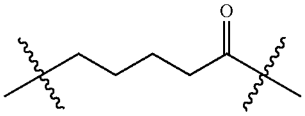 ,

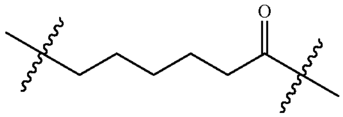 ,

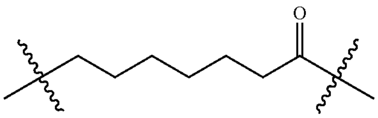 ,

-continued

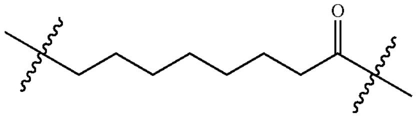,

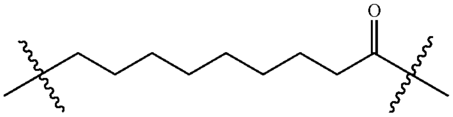,

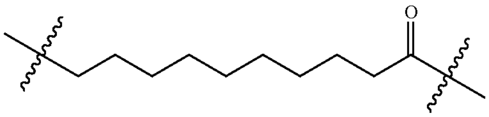,

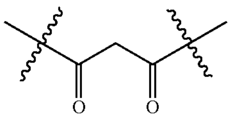, 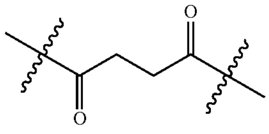,

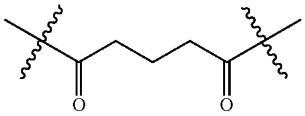,

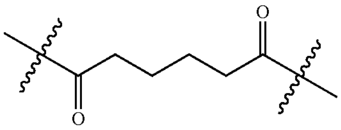,

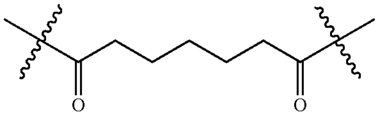,

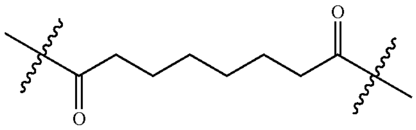,

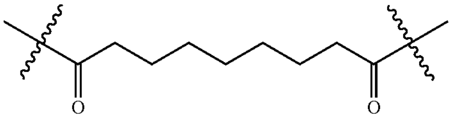,

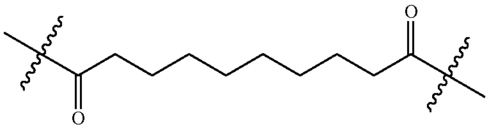,

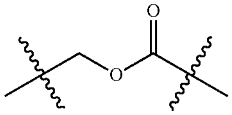, 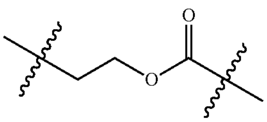,

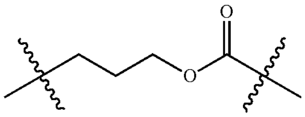,

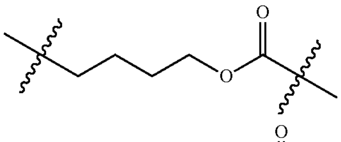,

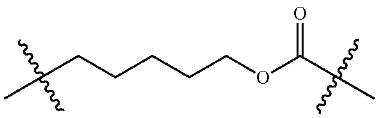,

-continued

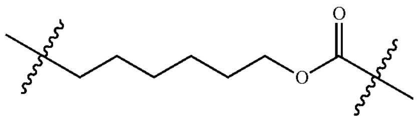,

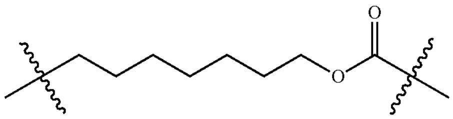, and

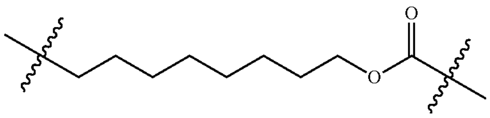.

Such embodiments are not limited to a particular definition for Y.

In some embodiments, Y is selected from S, NH, $NCH_3$, and Oxygen.

Such embodiments are not limited to a particular definition for Z.

In some embodiments, Z is selected from Carbon and Nitrogen.

Such embodiments are not limited to a particular definition for $R_1$.

In some embodiments, $R_1$ is selected from hydrogen, methyl, ethyl, hydroxyl,

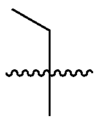, 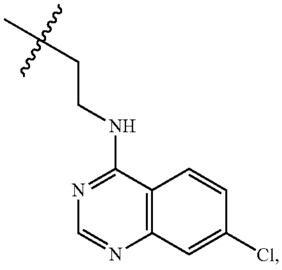

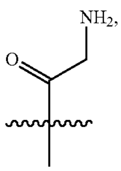 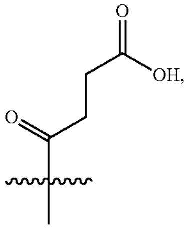 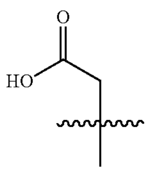,

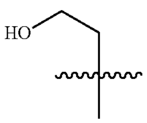, 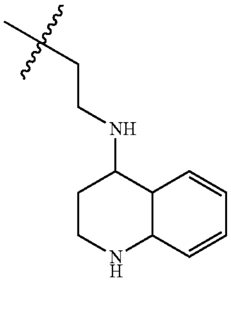,

-continued
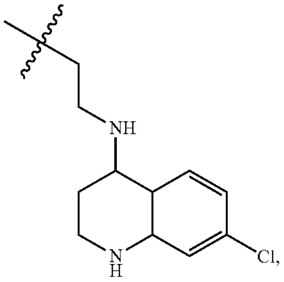
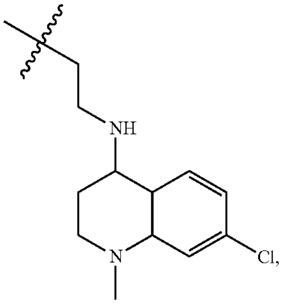
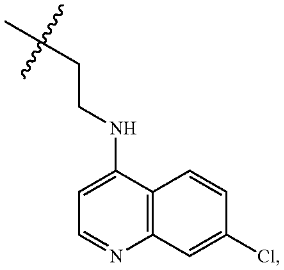
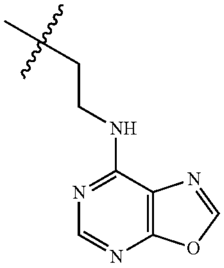
,
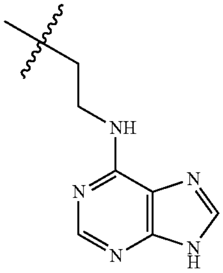
,
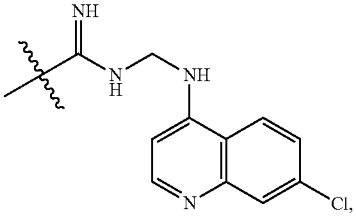
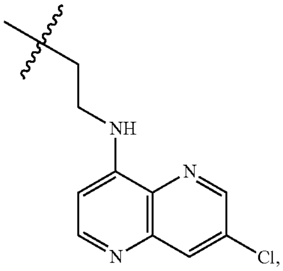
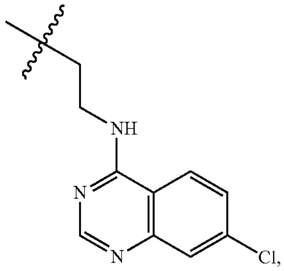
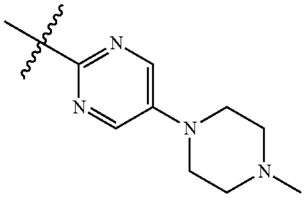
,
-continued
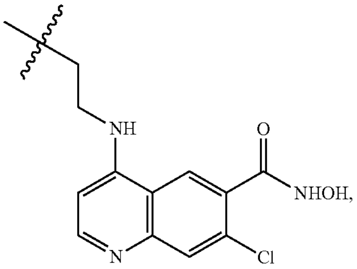
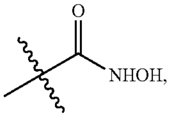
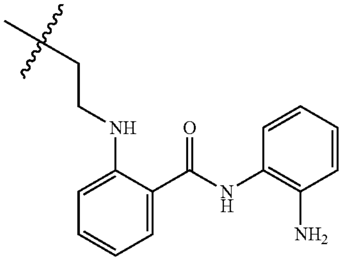
,
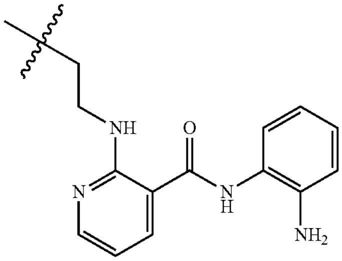
,
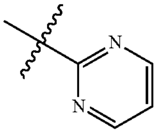
,
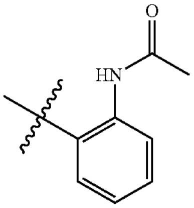
,
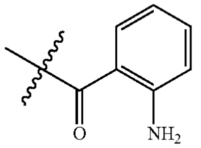
,
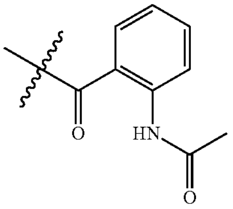
,
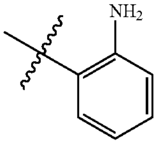
,
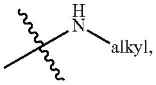
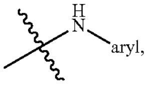
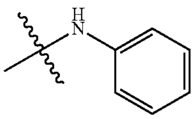
,
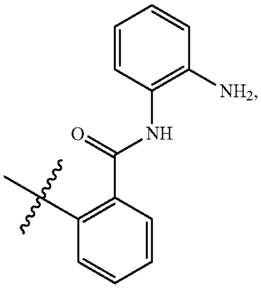

-continued
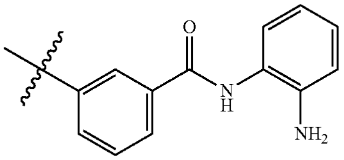
,
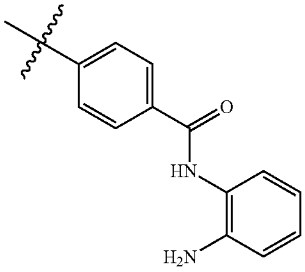
,
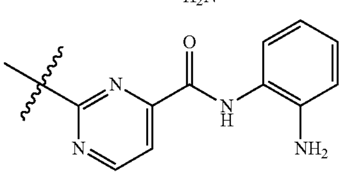
,
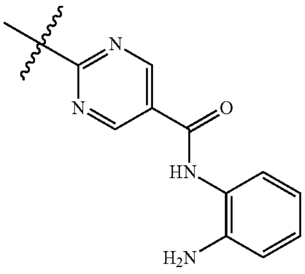
,
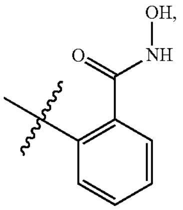
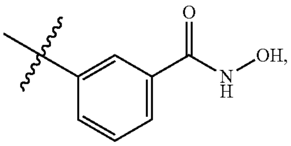
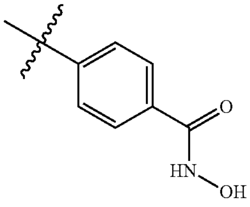
,
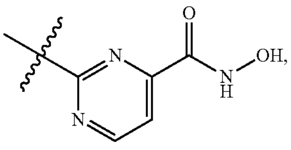
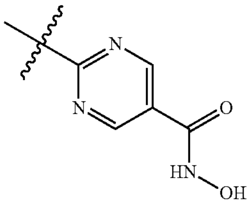
,
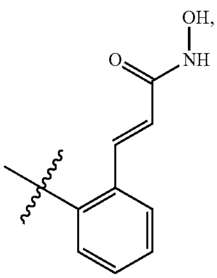
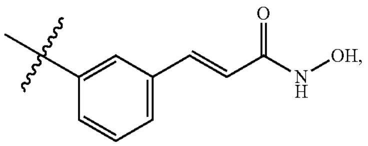
-continued
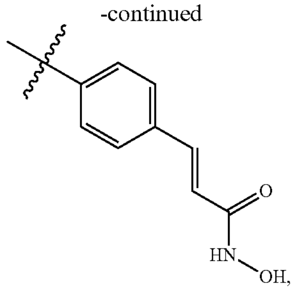
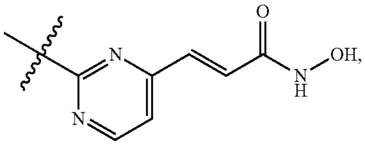
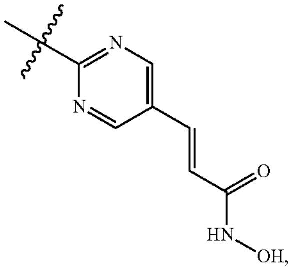
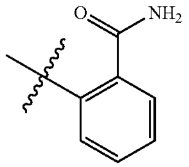
,
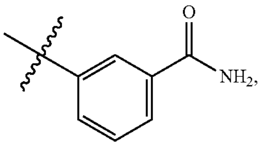
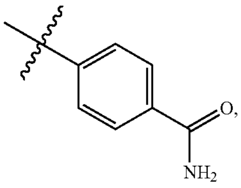
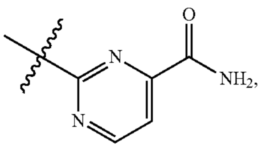
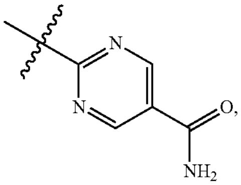
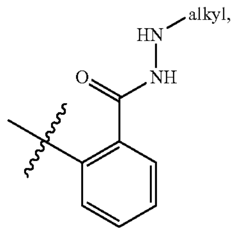
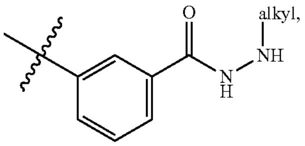
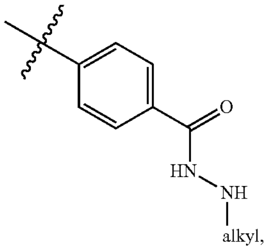
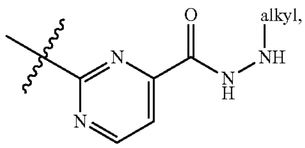

-continued
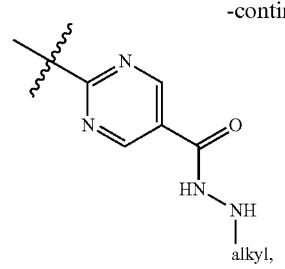
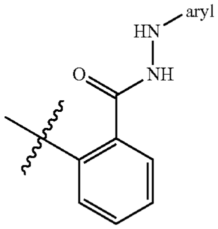
,
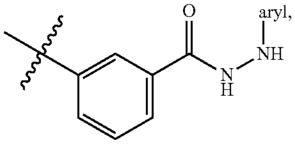
,
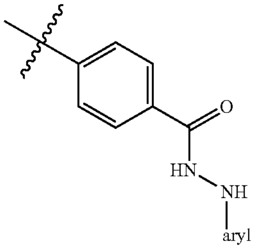
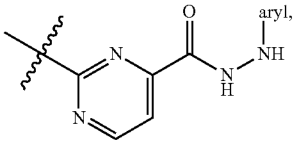
,
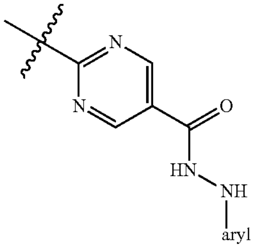
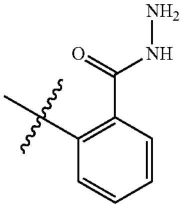
,
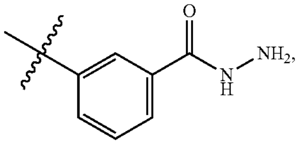
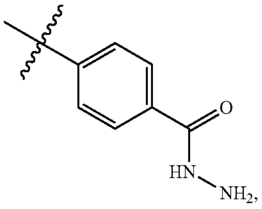
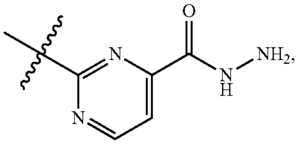
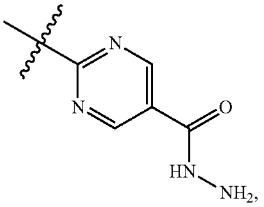
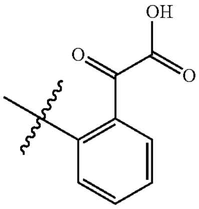
,
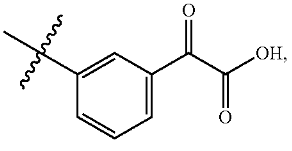
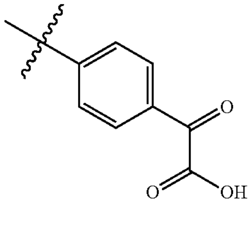
,
-continued
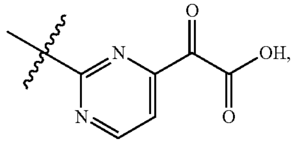
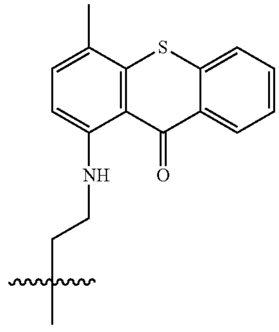
,
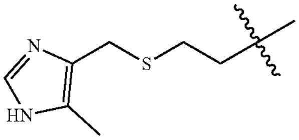
,
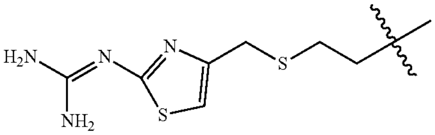
, and
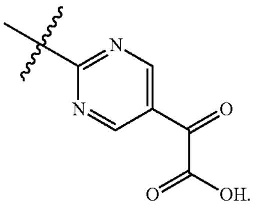
Such embodiments are not limited to a particular definition for $R_2$.
In some embodiments, $R_2$ is selected from hydrogen, methyl, ethyl,
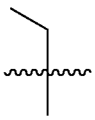
,
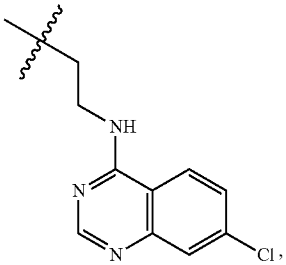
,
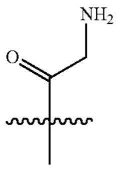
,
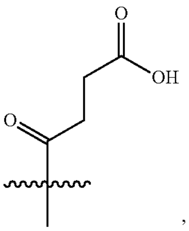
,
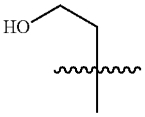
,
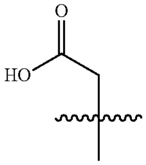
, -continued

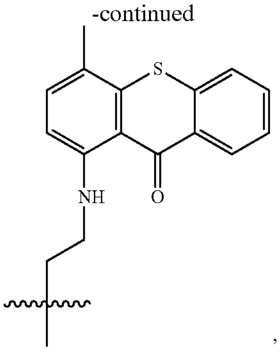

,

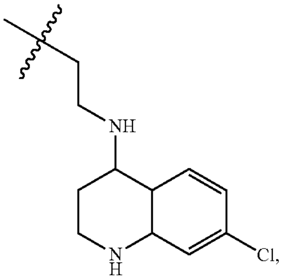

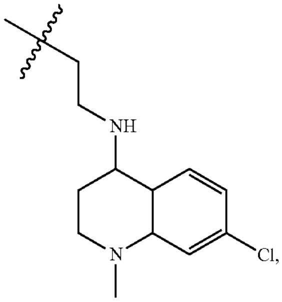

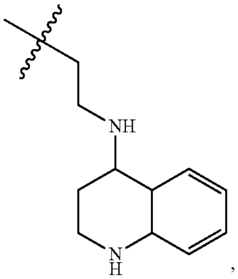

, and

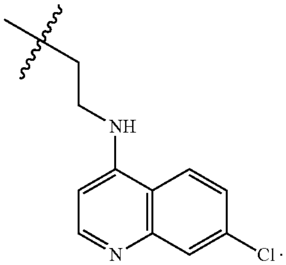

Such embodiments are not limited to a particular definition for $R_3$, $R_4$, $R_5$, and $R_6$.

In some embodiments, each of $R_3$, $R_4$, $R_5$, and $R_6$ is independently selected from hydrogen, fluorine, chlorine, bromine, iodine, hydroxyl, and $NH_2$.

Such embodiments are not limited to a particular definition for $R_7$.

In some embodiments, $R_7$ is selected from hydrogen, methyl, and deuterated methyl (e.g., $CD_3$).

Such embodiments are not limited to a particular definition for $R_8$.

In some embodiments, $R_8$ is selected from hydrogen,

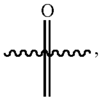

,

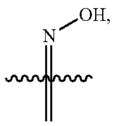

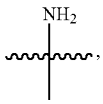

, and

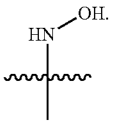

Such embodiments are not limited to a particular definition for $R_9$.

In some embodiments, $R_9$ is selected from hydrogen, methyl,

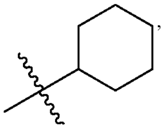

, and

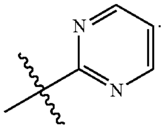

In some embodiments, the compound is recited in Table 1. Table 1 further includes partition coefficient values for each compound.

TABLE 1

| |
|---|
| 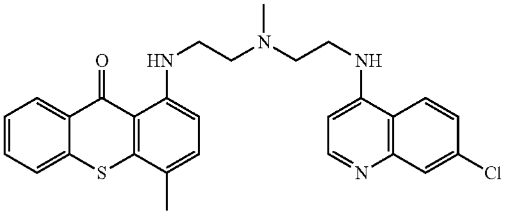 cLogP: 7.64 ROC-325 |
| 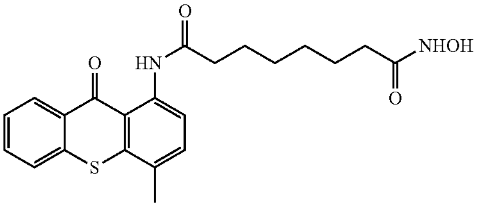 cLogP: 3.21 ROC-325H2 |
| 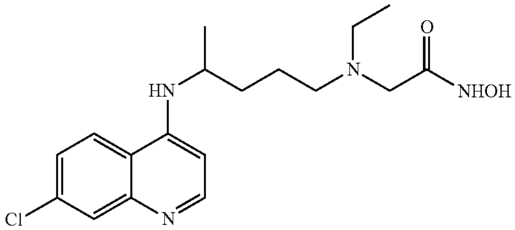 cLogP: 3.26 ROC-325H4 |
| 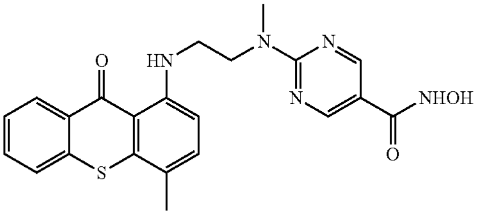 cLogP: 3.41 ROC-325H6 |

TABLE 1-continued
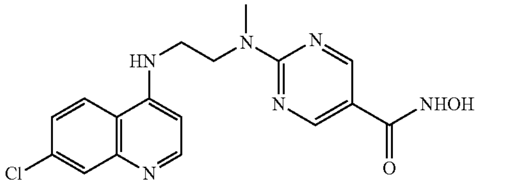
cLogP: 2.80
ROC-325H8
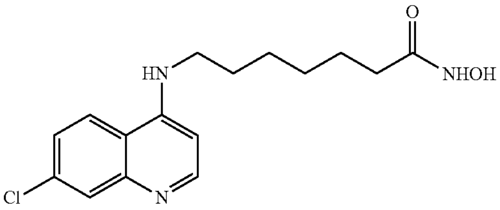
cLogP: 3.14
ROC-325H10
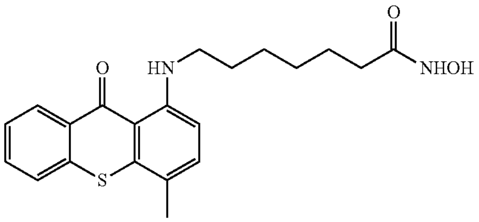
cLogP: 3.76
ROC-325H1
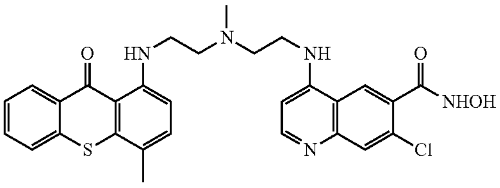
cLogP: 5.47
ROC-325H3
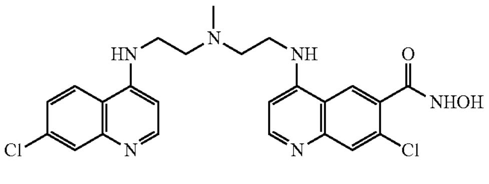
cLogP: 4.85
ROC-325H5
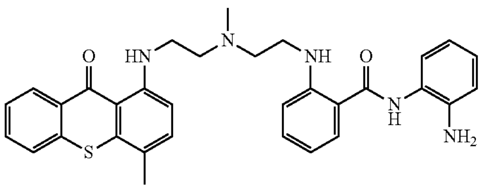
cLogP: 5.99
ROC-325H7
TABLE 1-continued
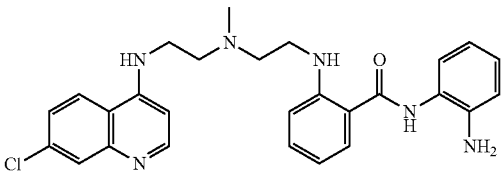
cLogP: 538
ROC-325H9
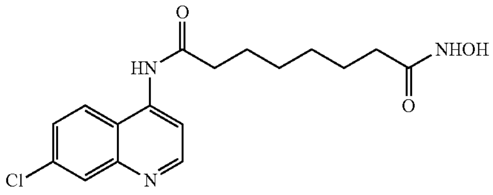
cLogP: 2.50
ROC-325H11
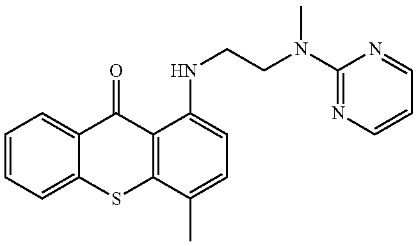
ROC-325P1
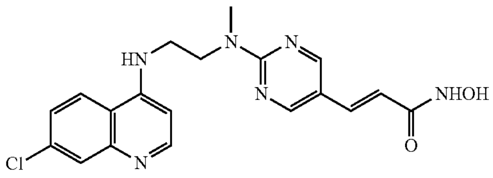
cLogP: 2.24
ROC-325H12
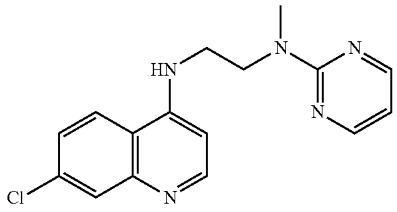
ROC-325P2
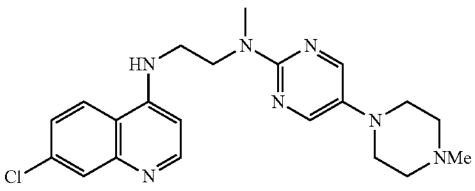
ROC-325P3

TABLE 1-continued
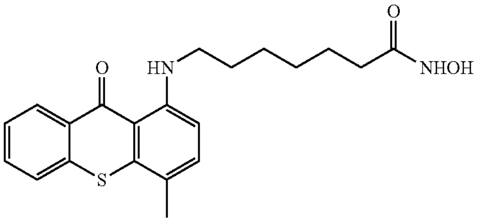
cLogP: 3.76
ROC-325H1
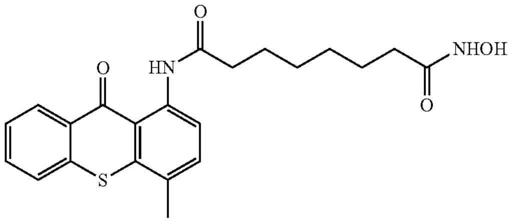
cLogP: 3.21
ROC-325H2
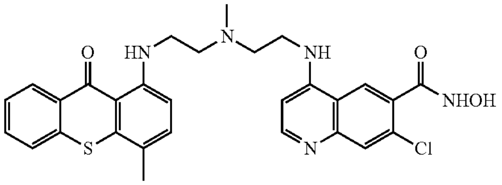
cLogP: 5.47
ROC-325H3
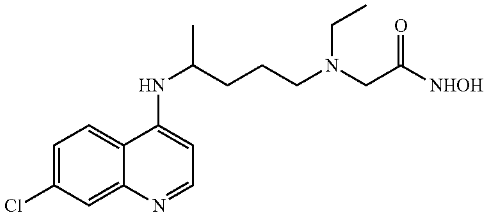
cLogP: 3.26
ROC-325H4
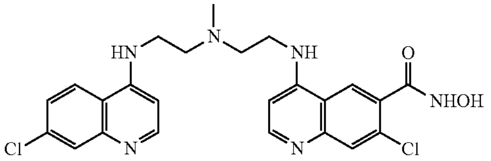
cLogP: 4.85
ROC-325H5
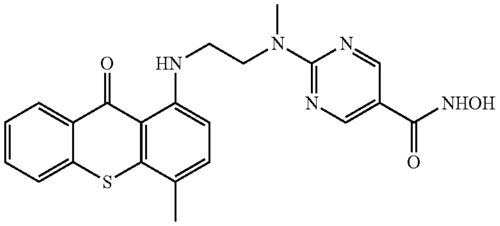
cLogP: 3.41
ROC-325H6
TABLE 1-continued
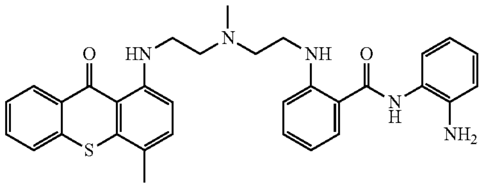
cLogP: 5.99
ROC-325H7
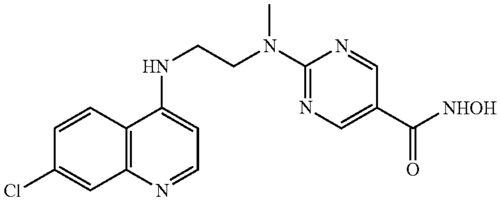
cLogP: 2.80
ROC-325H8
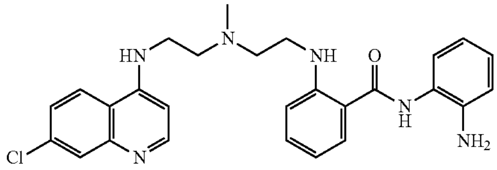
cLogP: 538
ROC-325H9
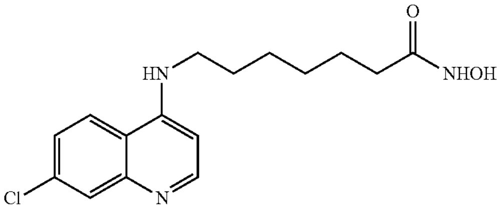
cLogP: 3.14
ROC-325H10
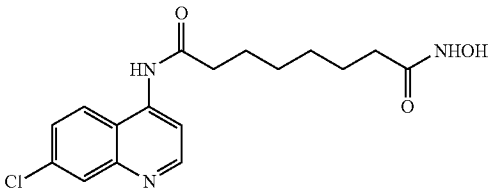
cLogP: 2.50
ROC-325H11
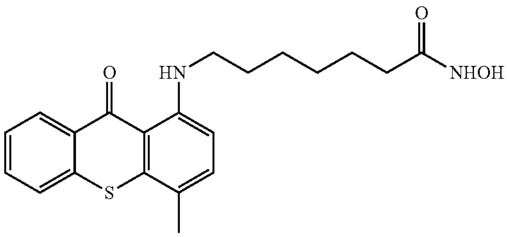
cLogP: 3.76

TABLE 1-continued
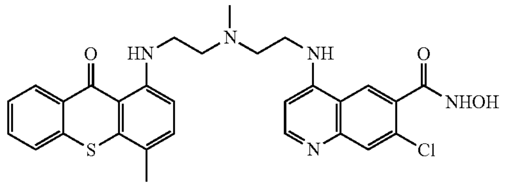
cLogP: 5.47
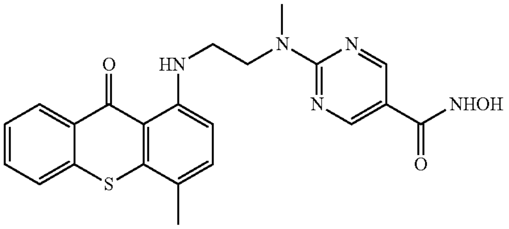
cLogP: 3.41
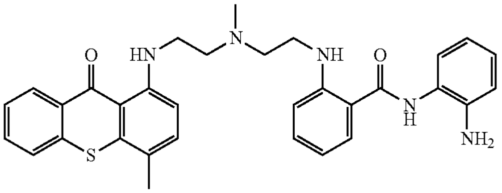
cLogP: 5.99
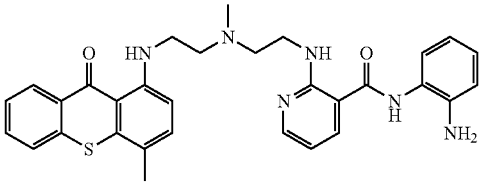
cLogP: 5.92
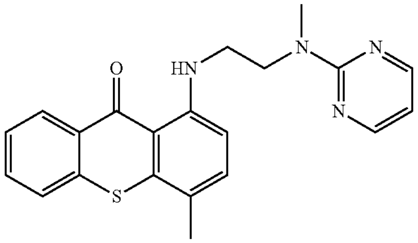
ROC-325P1
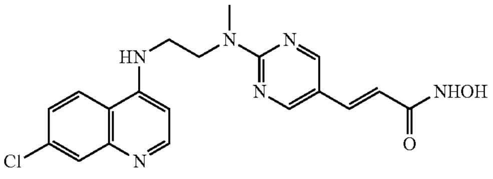
cLogP: 2.24
ROC-325H12
TABLE 1-continued
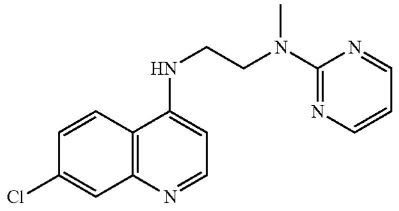
ROC-325P2
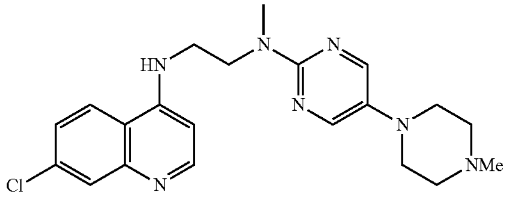
ROC-325P3
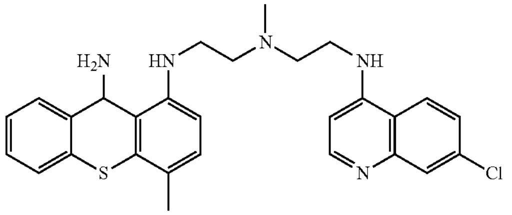
cLogP: 6.71
ROC-325A1
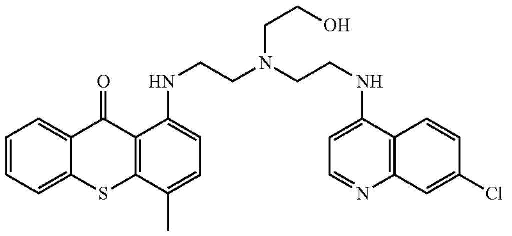
cLogP: 7.22
ROC-325A2
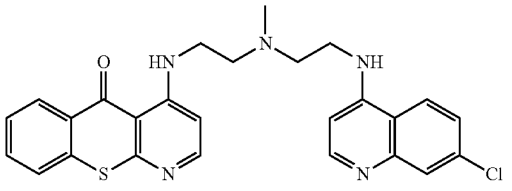
cLogP: 6.44
ROC-325A3
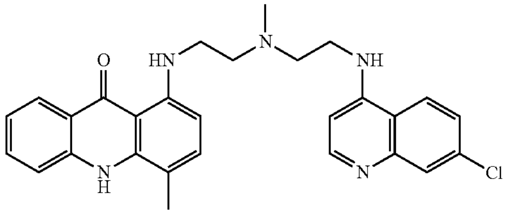
cLogP: 5.71
ROC-325A4

TABLE 1-continued
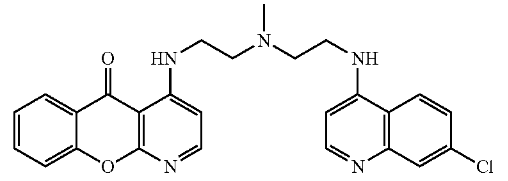
cLogP: 5.83
ROC-325A5
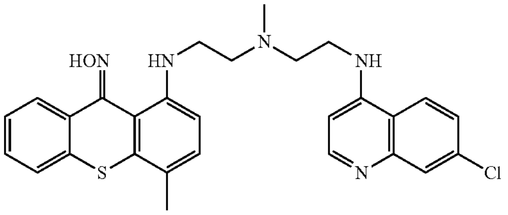
cLogP: 6.03
Compound 1
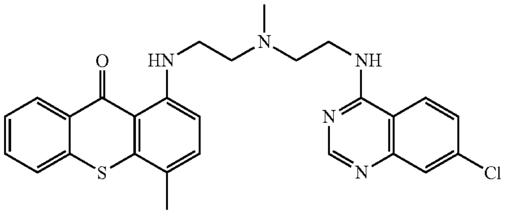
cLogP: 6.96
Compound 2
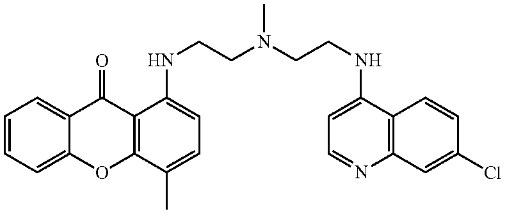
cLogP: 7.09
Compound 3
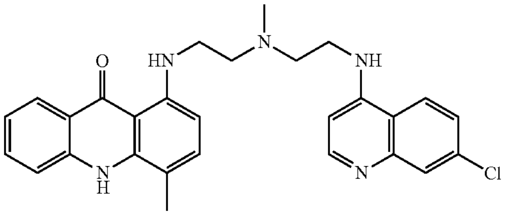
cLogP: 5.71
Compound 4
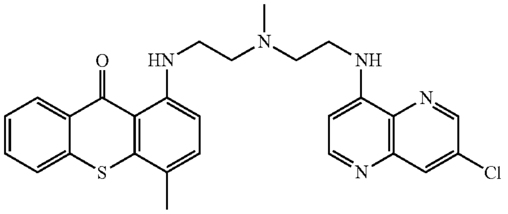
cLogP: 6.95
Compound 5
TABLE 1-continued
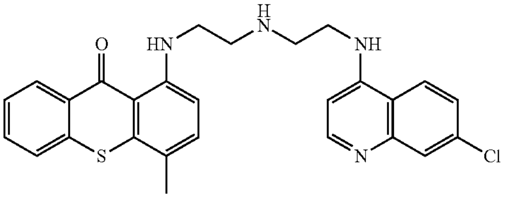
cLogP: 6.98
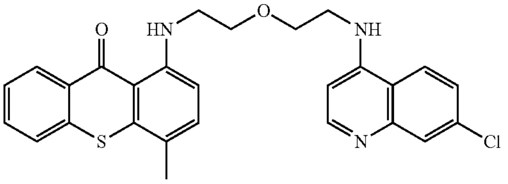
cLogP: 7.15
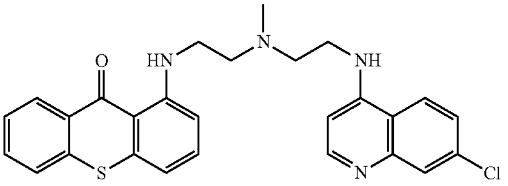
cLogP: 7.14
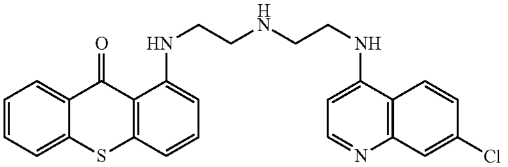
cLogP: 6.49
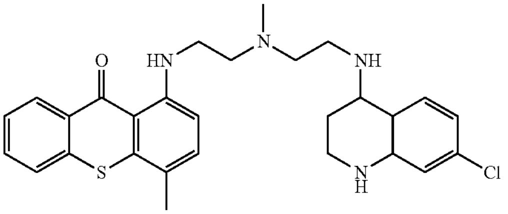 [SMILES: Cc1ccc(NCCN(C)CCNC2CCNC3C=C(Cl)C=CC32)c2c(=O)c3ccccc3sc12]
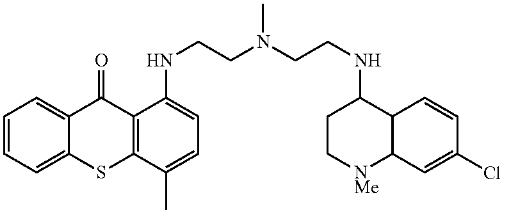 [SMILES: Cc1ccc(NCCN(C)CCNC2CCN(C)C3C=C(Cl)C=CC23)c2c(=O)c3ccccc3sc12]
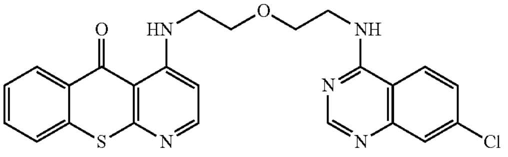
cLogP: 5.27

TABLE 1-continued
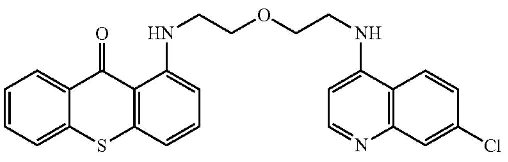
cLogP: 6.65
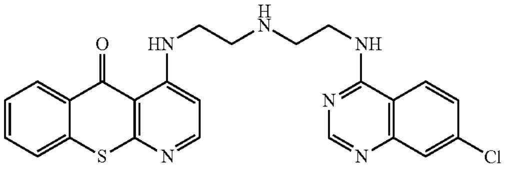
cLogP: 5.11
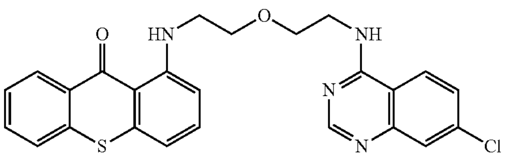
cLogP: 5.97
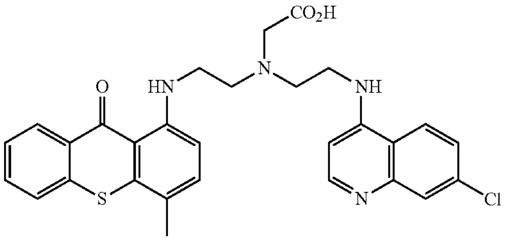
cLogP: 6.1
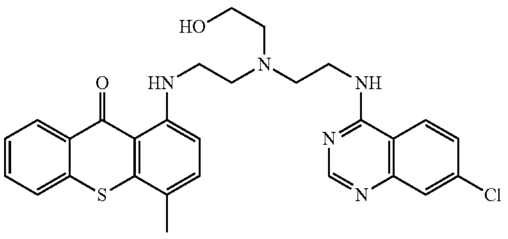
cLogP: 6.54
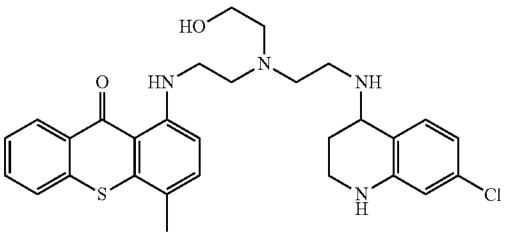 [SMILES: Cc1ccc(NCCN(CCO)CCNC2CCNc3cc(Cl)ccc32)c2c(=O)c3ccccc3sc12]
TABLE 1-continued
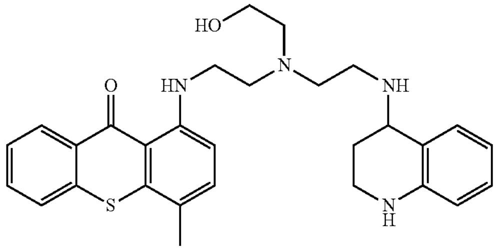 [SMILES: Cc1ccc(NCCN(CCO)CCNC2CCNc3ccccc32)c2c(=O)c3ccccc3sc12]
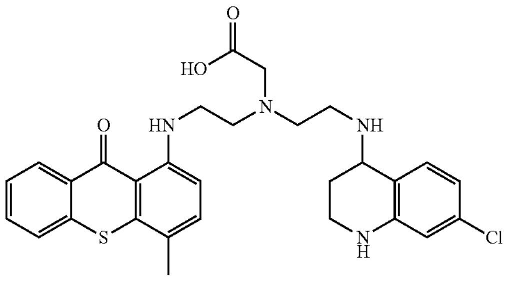 [SMILES: Cc1ccc(NCCN(CCNC2CCNc3cc(Cl)ccc32)CC(=O)O)c2c(=O)c3ccccc3sc12]
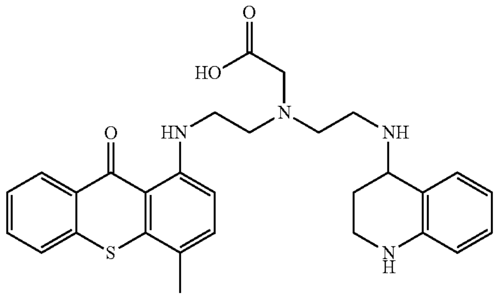 [SMILES: Cc1ccc(NCCN(CCNC2CCNc3ccccc32)CC(=O)O)c2c(=O)c3ccccc3sc12]
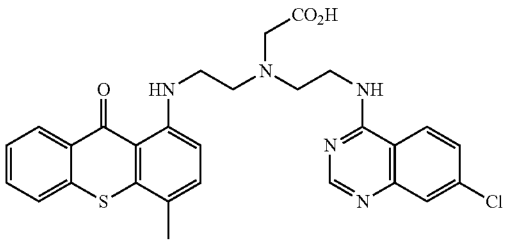
cLogP: 5.42
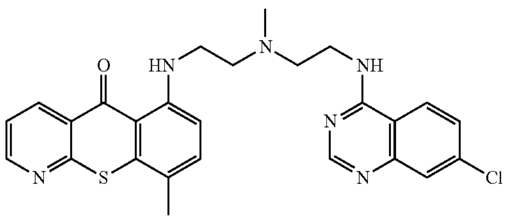
cLogP: 5.64
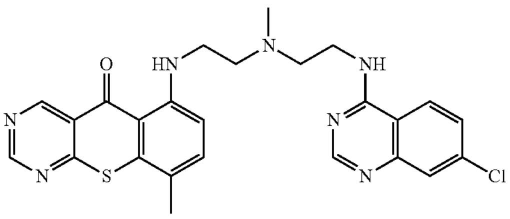
cLogP: 4.71

TABLE 1-continued
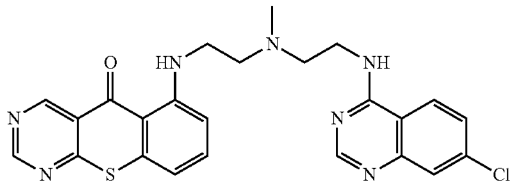
cLogP: 4.21
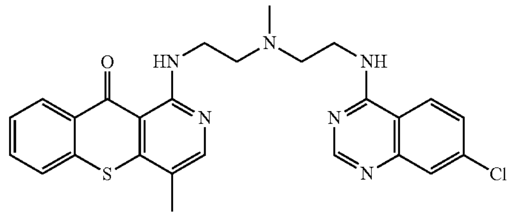
cLogP: 6.26
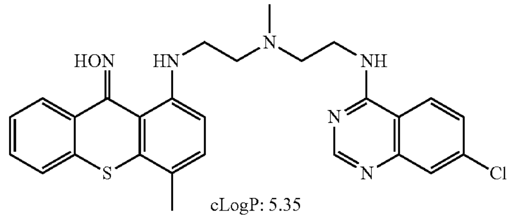
cLogP: 5.35
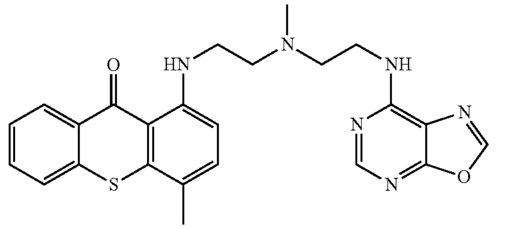
cLogP: 4.61
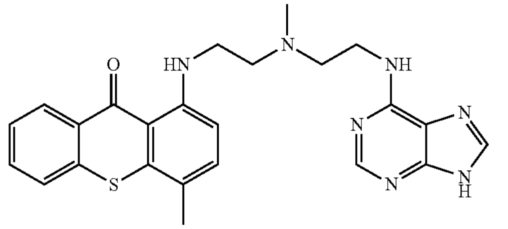
cLogP: 5
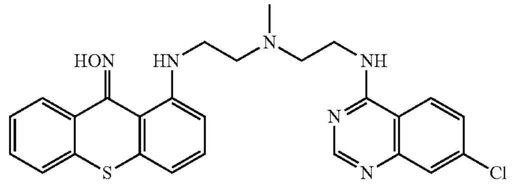
cLogP: 4.85
TABLE 1-continued
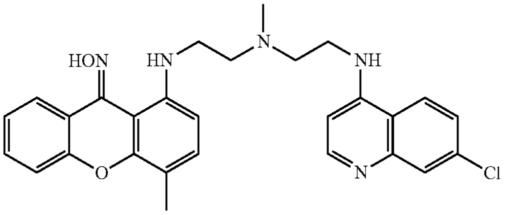
cLogP: 5.39
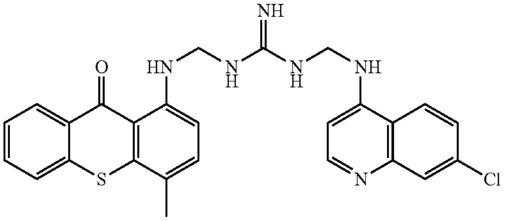
cLogP: 6.08
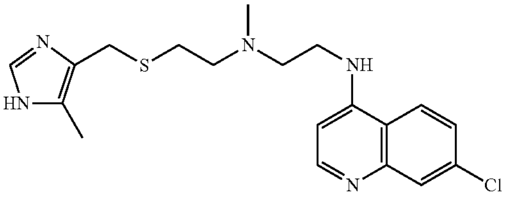
cLogP: 4.46
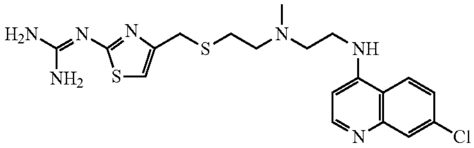
cLogP: 4.97
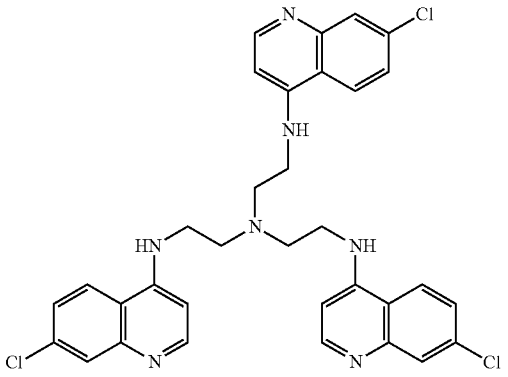
CLogP: 10.52

TABLE 1-continued
TABLE 1-continued
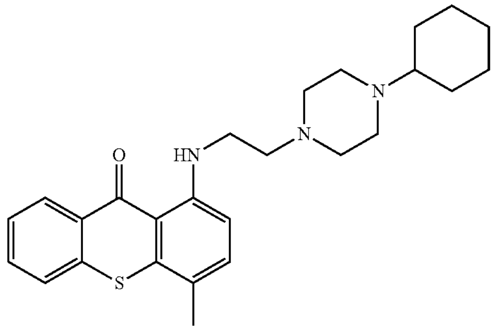 [SMILES: Cc1ccc(NCCN2CCN(C3CCCCC3)CC2)c2c(=O)c3ccccc3sc12]
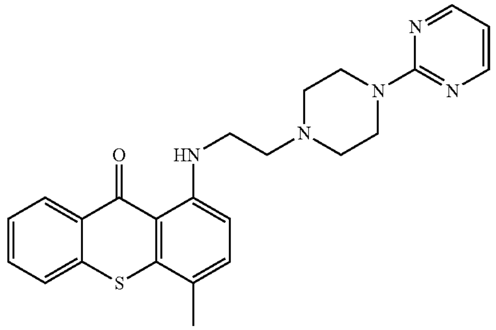 [SMILES: Cc1ccc(NCCN2CCN(c3ncccn3)CC2)c2c(=O)c3ccccc3sc12]
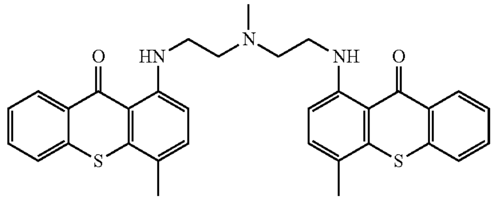 [SMILES: Cc1ccc(NCCN(C)CCNc2ccc(C)c3sc4ccccc4c(=O)c23)c2c(=O)c3ccccc3sc12]
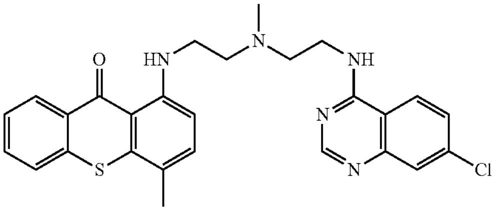 [SMILES: Cc1ccc(NCCN(C)CCNc2ncnc3cc(Cl)ccc23)c2c(=O)c3ccccc3sc12]
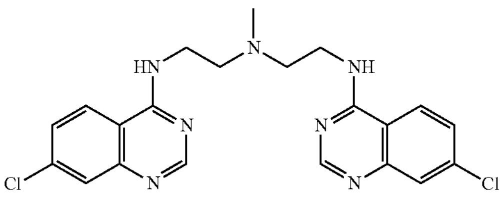 [SMILES: CN(CCNc1ncnc2cc(Cl)ccc12)CCNc1ncnc2cc(Cl)ccc12]
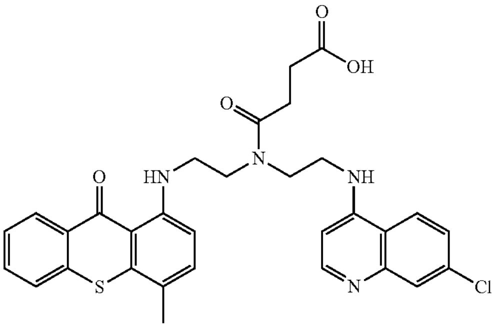 [SMILES: Cc1ccc(NCCN(CCNc2ccnc3cc(Cl)ccc23)C(=O)CCC(=O)O)c2c(=O)c3ccccc3sc12]
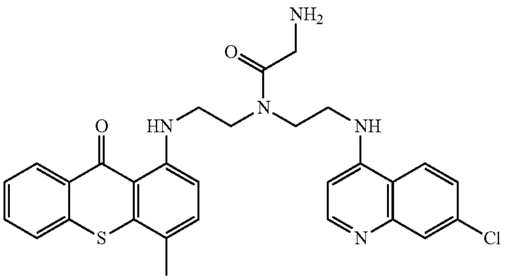 [SMILES: Cc1ccc(NCCN(CCNc2ccnc3cc(Cl)ccc23)C(=O)CN)c2c(=O)c3ccccc3sc12]
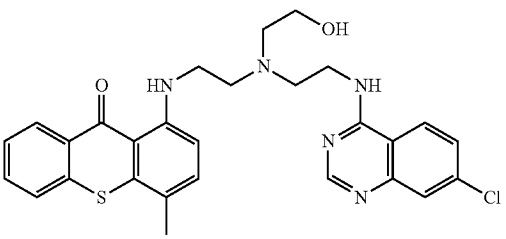 [SMILES: Cc1ccc(NCCN(CCO)CCNc2ncnc3cc(Cl)ccc23)c2c(=O)c3ccccc3sc12]
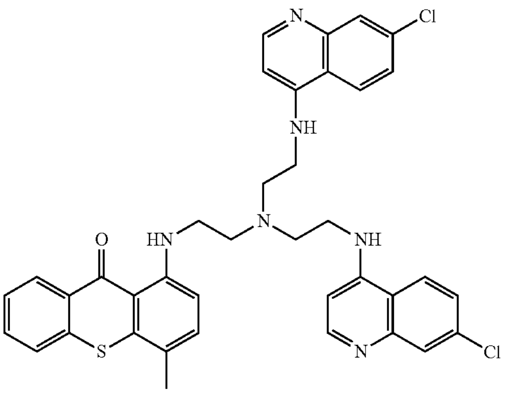
cLogP: 11.14
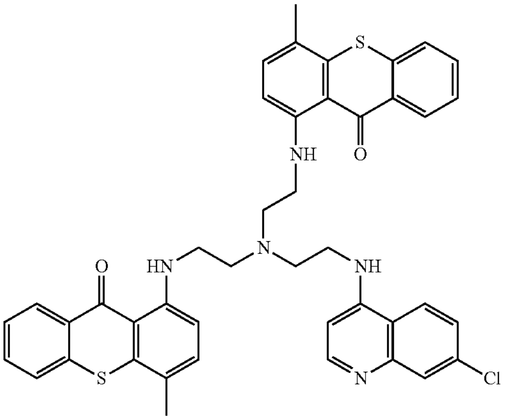
cLogP: 11.76

TABLE 1-continued

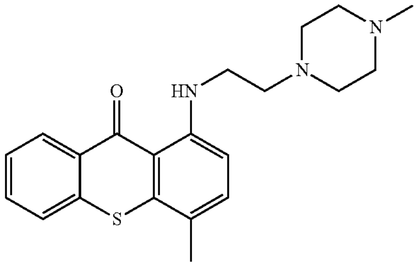 [SMILES: Cc1ccc(NCCN2CCN(C)CC2)c2c(=O)c3ccccc3sc12]

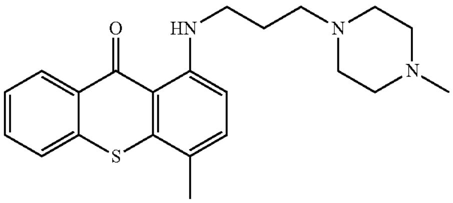 [SMILES: Cc1ccc(NCCCN2CCN(C)CC2)c2c(=O)c3ccccc3sc12]

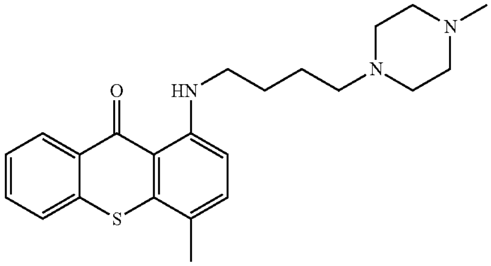 [SMILES: Cc1ccc(NCCCCN2CCN(C)CC2)c2c(=O)c3ccccc3sc12]

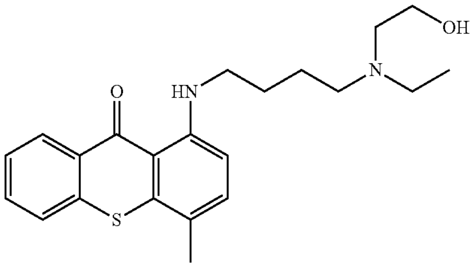 [SMILES: CCN(CCO)CCCCNc1ccc(C)c2sc3ccccc3c(=O)c12]

The invention further provides processes for preparing any of the compounds of the present invention.

As noted, the compounds of the invention are useful for the treatment, amelioration, or prevention of conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

The invention also provides pharmaceutical compositions comprising the compounds of the invention in a pharmaceutically acceptable carrier.

The invention also provides kits comprising a compound of the invention and instructions for administering the compound to an animal. The kits may optionally contain other therapeutic agents, e.g., agents useful in treating conditions that respond favorably to autophagy inhibition and/or HDAC inhibition (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

Severe acute respiratory syndrome coronavirus 2 (SARS-CoV-2) is an enveloped, positive-sense, single-stranded RNA beta-coronavirus that emerged in Wuhan in November 2019 and rapidly developed into a global pandemic. The associated disease, COVID-19, has an array of symptoms, ranging from flu-like illness and gastrointestinal distress (Xiao et al. 2020; Lin et al. 2020) to acute respiratory distress syndrome, heart arrhythmias, strokes, and death (Avula et al. 2020; Kochi et al. 2020). Drug repurposing has played an important role in the search for COVID-19 therapies. Recently, the FDA issued emergency approval of remdesivir (GS-5734), a monophosphoramidate prodrug of a nucleoside inhibitor developed for Ebola virus treatment (Mulangu et al. 2019), and hydroxychloroquine, an amino-quinoline derivative first developed in the 1940s for the treatment of malaria, for severely ill patients with COVID-19. However, there are no established prophylactic strategies or direct antiviral treatments available to limit SARS-CoV-2 infections and to prevent/cure the associated disease COVID-19.

Prophylactic strategies and/or direct antiviral treatments for preventing, treating and ameliorating the symptoms of SARS-CoV-2/COVID-19 are desperately needed.

In certain embodiments, the present invention provides methods for administering a pharmaceutical composition comprising one or more of the compounds of the present invention to a subject (e.g., a human subject) (e.g., a human subject suffering from or at risk of suffering from a condition related to SARS-CoV-2 infection (e.g., COVID-19)) for purposes of treating, preventing and/or ameliorating the symptoms of a viral infection (e.g., SARS-CoV-2 infection (e.g., COVID-19)).

In such embodiments, the methods are not limited treating, preventing and/or ameliorating the symptoms of a particular type or kind of viral infection. In some embodiments, the viral infection is a SARS-CoV-2 related viral infection (e.g., COVID-19). In some embodiments, the viral infection is any infection related to influenza, HIV, HIV-1, HIV-2, drug-resistant HIV, Junin virus, Chikungunya virus, Yellow Fever virus, Dengue virus, Pichinde virus, Lassa virus, adenovirus, Measles virus, Punta Toro virus, Respiratory Syncytial virus, Rift Valley virus, RHDV, SARS coronavirus, Tacaribe virus, and West Nile virus. In some embodiments, the viral infection is associated with any virals having $M^{pro}$ protease activity and/or expression.

In certain embodiments, the present invention provides methods for treating, ameliorating and/or preventing a condition related to viral infection in a subject, comprising administering to the subject a pharmaceutical composition comprising one or more of the compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the viral infection is a SARS-CoV-2 viral infection.

In certain embodiments, the present invention provides methods for treating, ameliorating and/or preventing symptoms related to viral infection in a subject, comprising administering to the subject a pharmaceutical composition comprising one or more of the compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection. In some embodiments, the one or more symptoms related to viral infection includes, but is not limited to, fever, fatigue, dry cough, myalgias, dyspnea, acute respiratory distress syndrome, and pneumonia.

In certain embodiments, the present invention provides methods for treating, ameliorating and/or preventing acute respiratory distress syndrome in a subject, comprising one or more of the compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In certain embodiments, the present invention provides methods for treating, ameliorating and/or preventing pneumonia in a subject, comprising administering to the subject a pharmaceutical composition comprising one or more compounds of the present invention. In some embodiments, the pharmaceutical composition is configured for any manner of administration (e.g., oral, intravenous, topical). In some embodiments, the subject is a human subject. In some embodiments, the subject is a human subject suffering from or at risk of suffering from a condition related to SARS-CoV-2 infection (e.g., COVID-19). In some embodiments, the subject is a human subject suffering from a SARS-CoV-2 viral infection.

In some embodiments involving the treatment of acute respiratory distress syndrome and/or pneumoina, the pharmaceutical composition is administered in combination with a known agent to treat respiratory diseases. Known or standard agents or therapies that are used to treat respiratory diseases include, anti-asthma agent/therapies, anti-rhinitis agents/therapies, anti-sinusitis agents/therapies, anti-emphysema agents/therapies, anti-bronchitis agents/therapies or anti-chronic obstructive pulmonary disease agents/therapies. Anti-asthma agents/therapies include mast cell degranulation agents, leukotriene inhibitors, corticosteroids, beta-antagonists, IgE binding inhibitors, anti-CD23 antibody, tryptase inhibitors, and VIP agonists. Anti-allergic rhinitis agents/therapies include H1 antihistamines, alpha-adrenergic agents, and glucocorticoids. Anti-chronic sinusitis therapies include, but are not limited to surgery, corticosteroids, antibiotics, anti-fungal agents, salt-water nasal washes or sprays, anti-inflammatory agents, decongestants, guaifensesin, potassium iodide, luekotriene inhibitors, mast cell degranulating agents, topical moisterizing agents, hot air inhalation, mechanical breathing devices, enzymatic cleaners and antihistamine sprays. Anti-emphysema, anti-bronchitis or anti-chronic obstructive pulmonary disease agents/therapies include, but are not limited to oxygen, bronchodilator agents, mycolytic agents, steroids, antibiotics, anti-fungals, moisterization by nebulization, anti-tussives, respiratory stimulants, surgery and alpha 1 antitrypsin.

In certain embodiments, the present invention provides kits comprising (1) a pharmaceutical composition comprising one or more compounds of the present invention, (2) a container, pack, or dispenser, and (3) instructions for administration. In some embodiments, the kit further comprises remdesivir or hydroxychloroquine.

BRIEF DESCRIPTION OF THE DRAWINGS

FIG. 1. Activity of SAHA, lucanthone, HCQ, ROC-325, and novel autophagy inhibitors in the MOLM-13 AML model. MOLM-13 cells were treated with the indicated concentrations of drugs for 72 hours and cell viability was determined by MTT assay. Mean±SD, n=4.

DEFINITIONS

The terminology as set forth herein is for description of the embodiments only and should not be construed as limiting of the invention as a whole. Unless otherwise specified, “a,” “an,” “the,” and “at least one” are used interchangeably. Furthermore, as used in the description of the invention and the appended claims, the singular forms “a”, “an”, and “the” are inclusive of their plural forms, unless contraindicated by the context surrounding such.

The term “compound” is used herein to describe any specific compound or bioactive agent disclosed herein, including any and all stereoisomers (including diasteromers), individual optical isomers (enantiomers) or racemic mixtures, pharmaceutically acceptable salts and prodrug forms. The term compound herein refers to stable compounds. Within its use in context, the term compound may refer to a single compound or a mixture of compounds as otherwise described herein. It is understood that the choice of substituents or bonds within a Markush or other group of substituents or bonds is provided to form a stable compound from those choices within that Markush or other group.

As used herein, the terms “alkyl”, “alkenyl”, and the prefix “alk-” are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

The term “aryl” as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

The term “autophagy” is used to describe a catabolic process in cells which involves the degradation of a cell's own components through lysosomes.

“Treat”, “treating”, and “treatment”, etc., as used herein, refer to any action providing a benefit to a patient at risk for or afflicted with a disease, including improvement in the condition through lessening or suppression of at least one symptom, delay in progression of the disease, delay in the onset of the disease, etc. Treatment also includes partial or total inhibition of autophagy and/or HDAC activity in a subject having a disease or condition that responds favorably to such inhibition.

As used herein, the term “prevention” includes either preventing the onset of a clinically evident disease or condition in individuals at risk. Also intended to be encompassed by this definition is the decrease of autophagy in cells to prevent the occurrence of a disease facilitated by autophagy. This includes prophylactic treatment of those having an enhanced risk of developing precancers and cancers facilitated by autophagy and/or aberrant HDAC activity. An elevated risk represents an above-average risk that a subject will develop a disease or condition involving autophagy (e.g., cancer), which can be determined, for example, through family history or the detection of genes causing a predisposition to autophagy-dependent disease.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent that will achieve the goal of decreasing disease severity while avoiding adverse side effects such as those typically associated with alternative therapies. The therapeutically effective amount may be administered in one or more doses. An effective amount, on the other hand, is an amount sufficient to provide a significant chemical effect, such as the inhibition of autophagy by a detectable amount.

The term "subject" for purposes of treatment includes any human or animal subject who has a disorder facilitated by autophagy and/or aberrant HDAC activity. Such disorders include, but are not limited to cancer, pulmonary hypertension, diabetes, neurodegenerative disorders, aging, heart disease, rheumatoid arthritis, infectious diseases, etc. For methods of prevention the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on. Besides being useful for human treatment, the compounds of the present invention are also useful for veterinary treatment of mammals, including companion animals and farm animals, such as, but not limited to dogs, cats, horses, cows, sheep, and pigs. Preferably, subject means a human.

DETAILED DESCRIPTION OF THE INVENTION

Autophagy is an evolutionarily conserved lysosomal protein degradation process. Aberrant autophagy plays a role in the pathogenesis of many health conditions including cancer, pulmonary hypertension, diabetes, neurodegenerative disorders, aging, heart disease, rheumatoid arthritis, infectious diseases, etc. The present invention relates to a new class of small-molecules having a quinoline or thioxanthenone (or similar) structure which function as autophagy inhibitors and/or histone deactylase inhibitors, and their use as therapeutics for the treatment of conditions characterized with aberrant autophagy activity and/or aberrant HDAC activity.

In a particular embodiment, compounds encompassed within the following formulas are provided:

(Formula I)

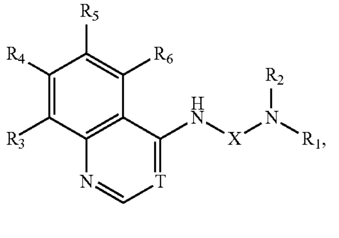

-continued (Formula II)

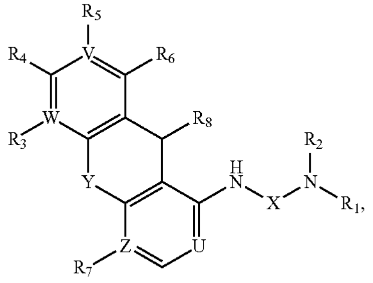

(Formula III)

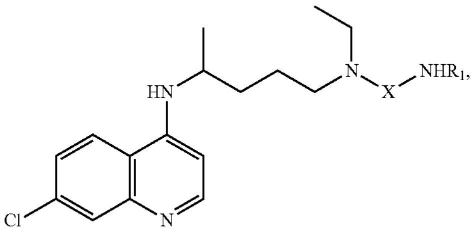

and (Formula IV)

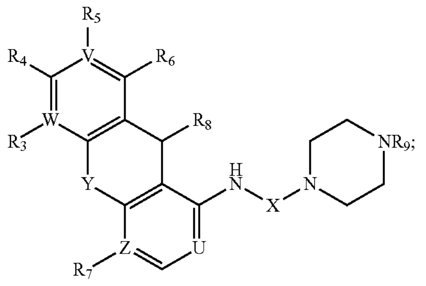

including pharmaceutically acceptable salts, solvates, and/or prodrugs thereof.

Formulas I, III, and III are not limited to a particular chemical moiety for T, U, V, W, X, Y, Z, $R_1$, $R_2$, $R_3$, $R_4$, $R_5$, $R_6$, $R_7$, $R_8$, and $R_9$. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular autophagy. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular HDAC activity. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to inhibit cellular autophagy and cellular HDAC activity. In some embodiments, the particular chemical moiety for T, U, V, W, X, Y, Z, $R_1$, $R_2$, $R_3$, $R_4$, $R_5$, $R_6$, $R_7$, $R_8$, and $R_9$ independently include any chemical moiety that permits the resulting compound to act as an effective therapeutic for treating conditions characterized with aberrant autophagy activity and/or aberrant HDAC activity (e.g., cancer, pulmonary hypertension, diabetes, neurodegenerative disorders, aging, heart disease, rheumatoid arthritis, infectious diseases, conditions and symptoms caused by a viral infection (e.g., COVID-19)).

Such embodiments are not limited to a particular definition for T.

In some embodiments, T is selected from Carbon and Nitrogen.

Such embodiments are not limited to a particular definition for U.

In some embodiments, U is selected from Carbon and Nitrogen.

Such embodiments are not limited to a particular definition for V.

In some embodiments, V is selected from Carbon and Nitrogen.

Such embodiments are not limited to a particular definition for W.

In some embodiments, W is selected from Carbon and Nitrogen.

Such embodiments are not limited to a particular definition for X.

In some embodiments, X is selected from

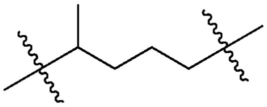 , 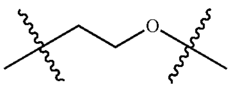 ,

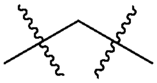 , 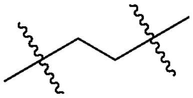 ,

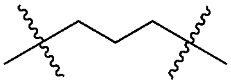 , 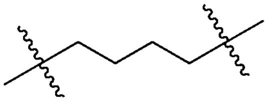 ,

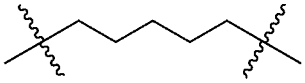 ,

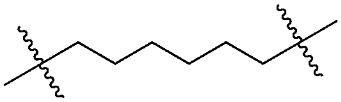 ,

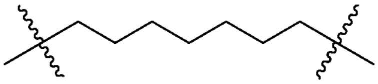 ,

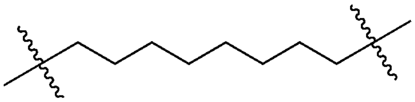 ,

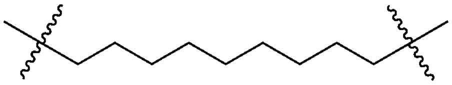 ,

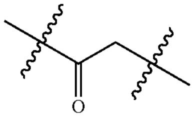 , 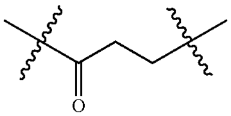 ,

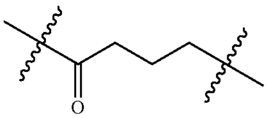 ,

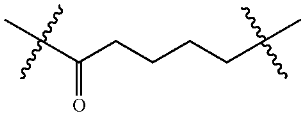 ,

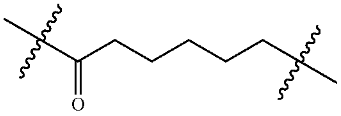 ,

-continued

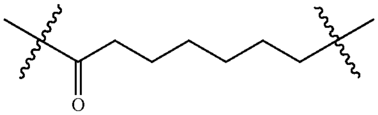 ,

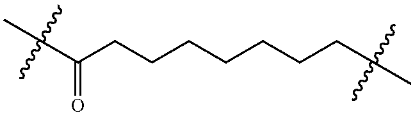 ,

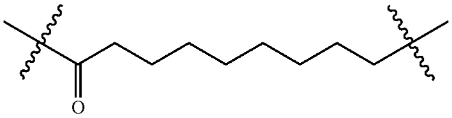 ,

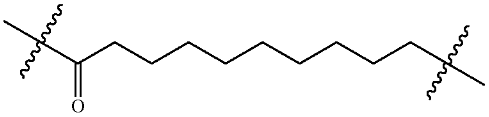 ,

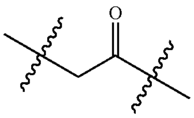 , 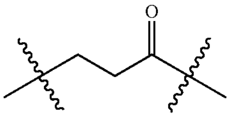 ,

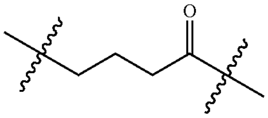 ,

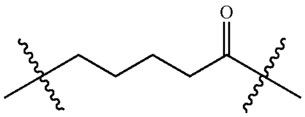 ,

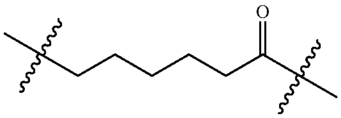 ,

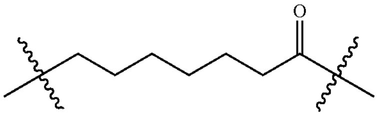 ,

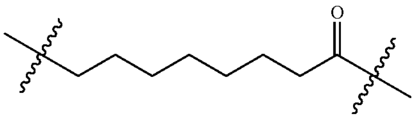 ,

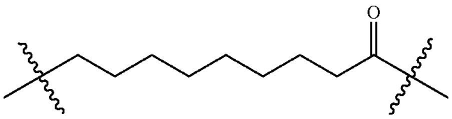 ,

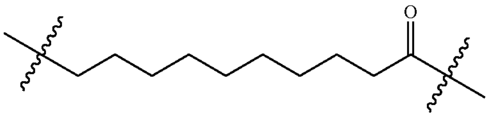 ,

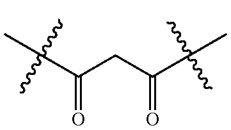 , 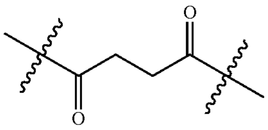 ,

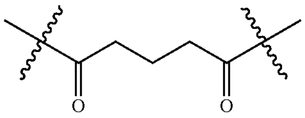 ,

-continued

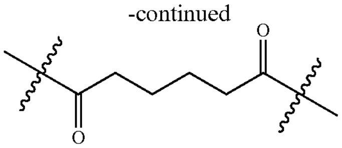
,

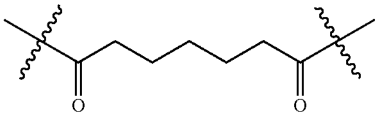
,

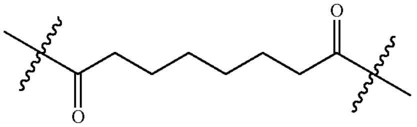
,

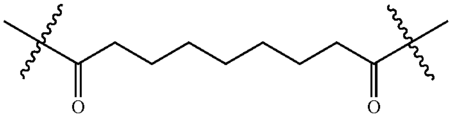
,

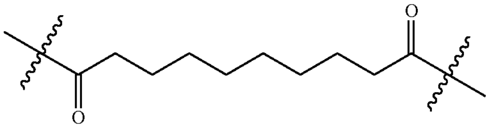
,

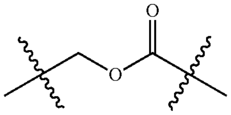
,
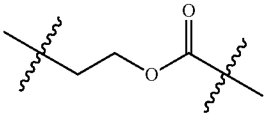
,

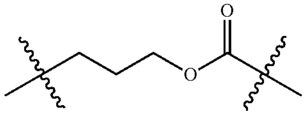
,

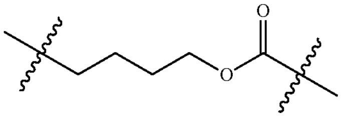
,

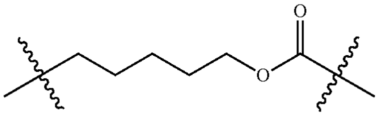
,

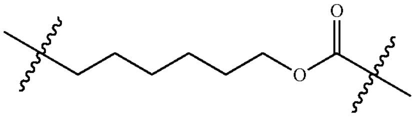
,

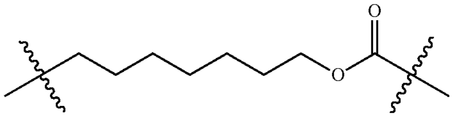
, and

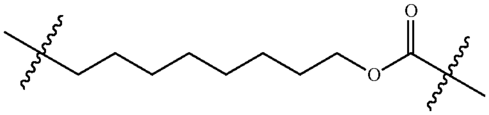
.

Such embodiments are not limited to a particular definition for Y.

In some embodiments, Y is selected from S, NH, $NCH_3$, and Oxygen.

Such embodiments are not limited to a particular definition for Z.

In some embodiments, Z is selected from Carbon and Nitrogen.

Such embodiments are not limited to a particular definition for $R_1$.

In some embodiments, $R_1$ is selected from hydrogen, methyl, ethyl, hydroxyl,

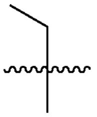
,
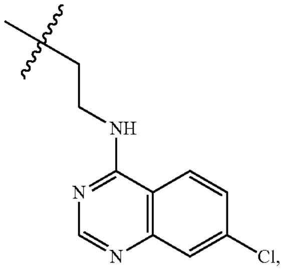
,

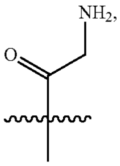
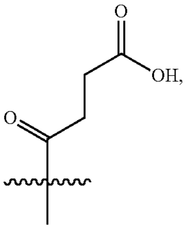
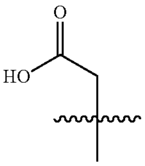
,

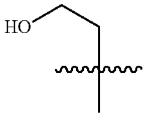
,
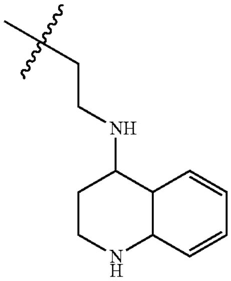
,

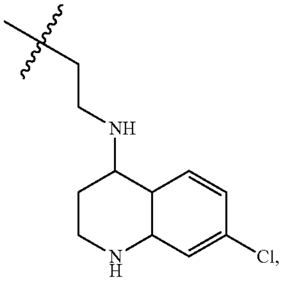
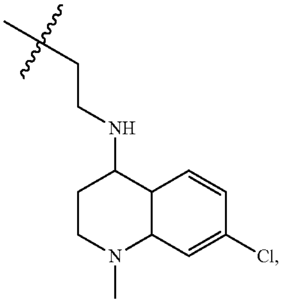

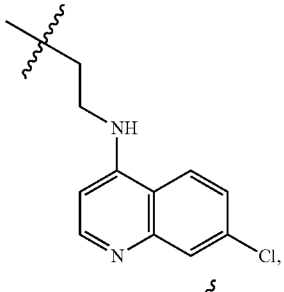
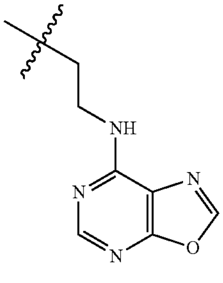
,

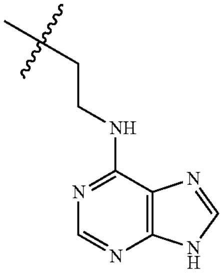
,

-continued
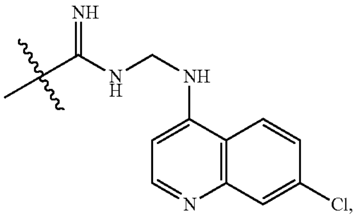
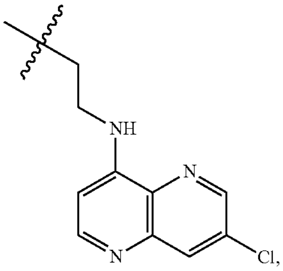
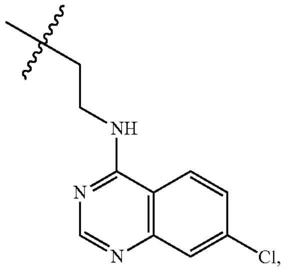
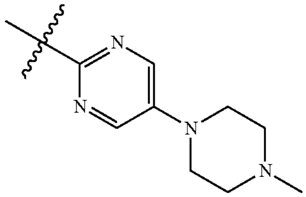
,
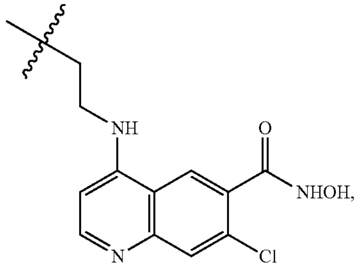
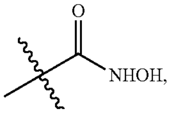
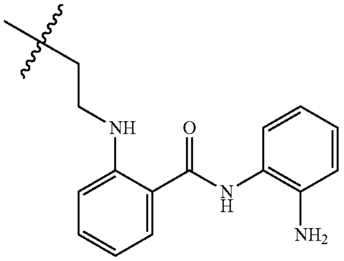
,
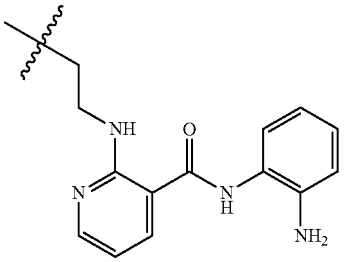
,
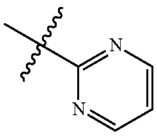
,
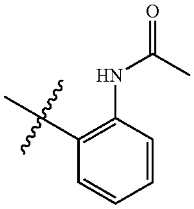
,
-continued
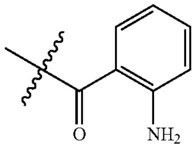
,
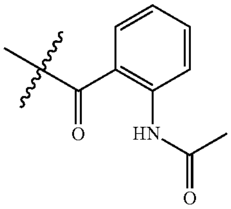
,
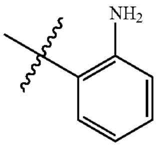
,
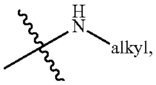
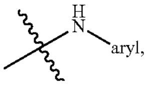
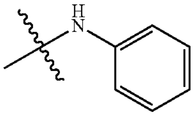
,
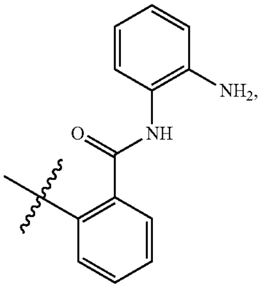
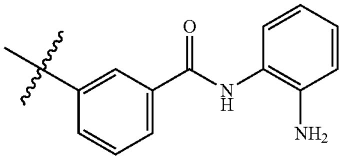
,
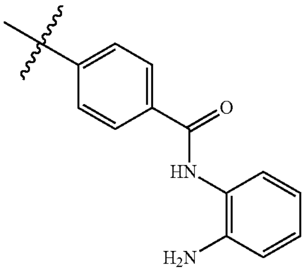
,
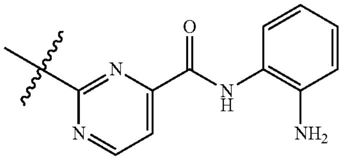
,
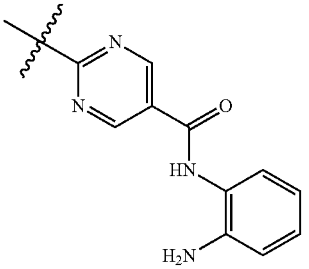
,
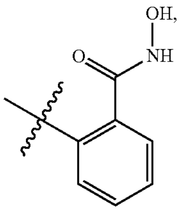
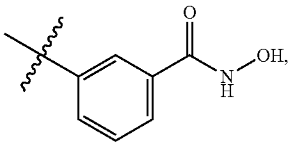
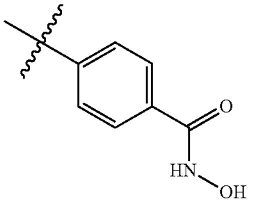
, -continued
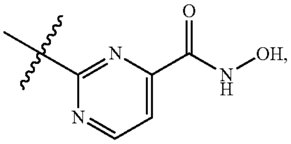
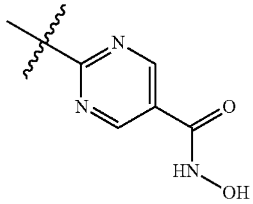
,
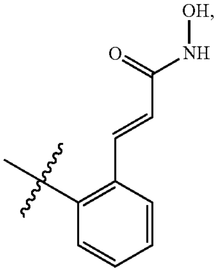
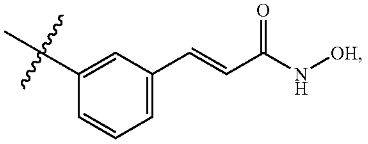
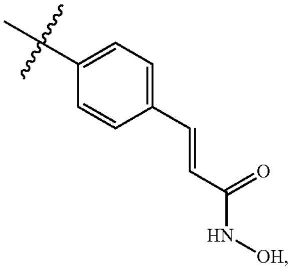
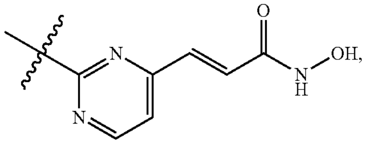
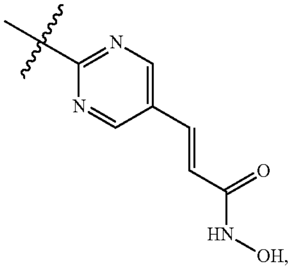
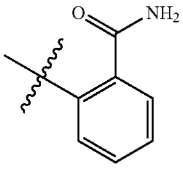
,
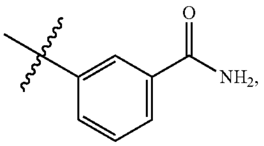
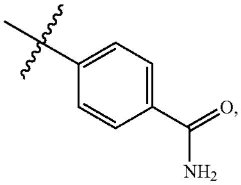
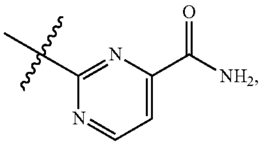
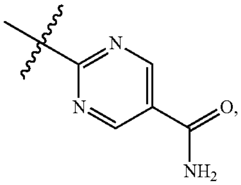
-continued
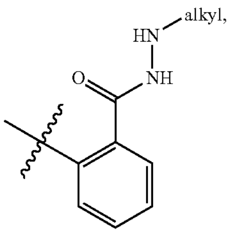
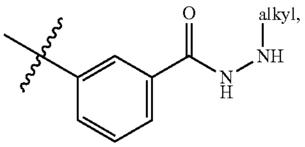
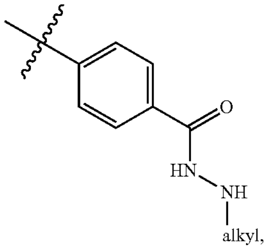
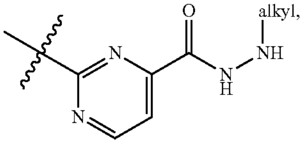
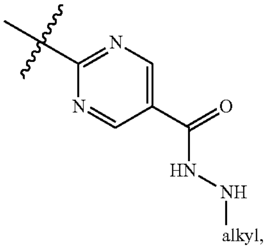
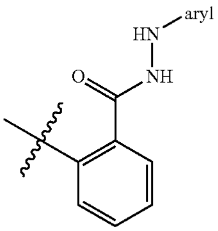
,
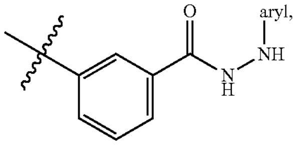
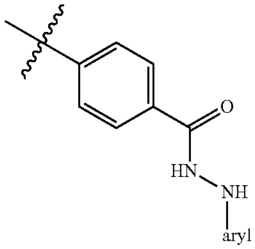
,
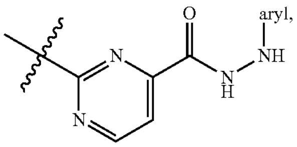
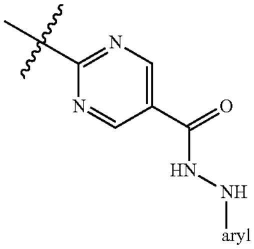
,
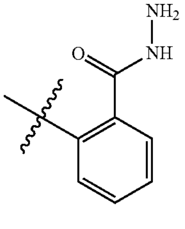
,
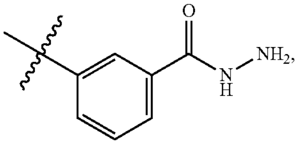

-continued
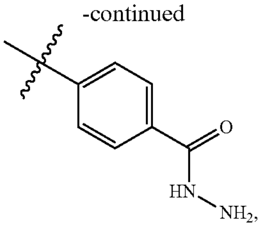
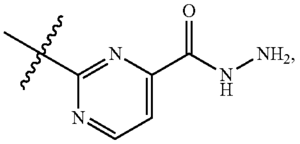
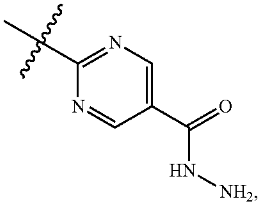 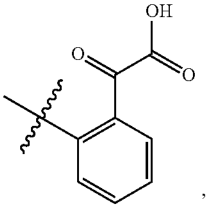 ,
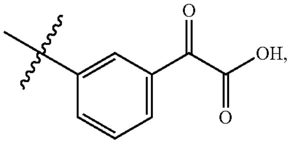 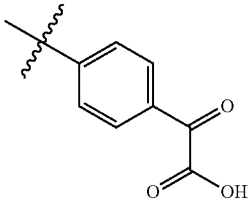 ,
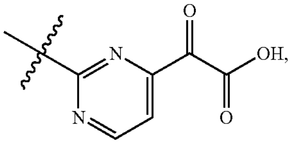
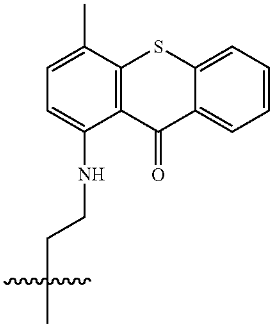 ,
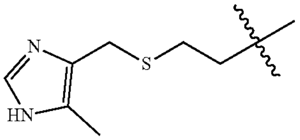 ,
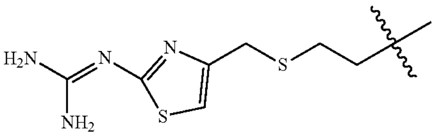 , and
-continued
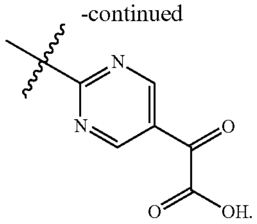
Such embodiments are not limited to a particular definition for $R_2$.
In some embodiments, $R_2$ is selected from hydrogen, methyl, ethyl,
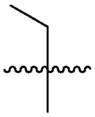 , 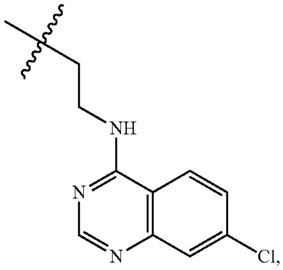
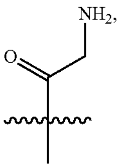 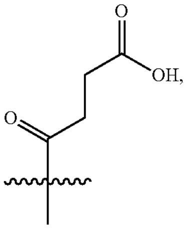 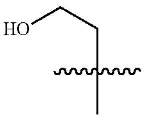 ,
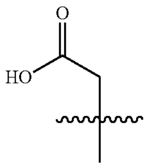 , 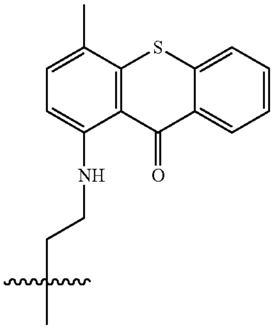 ,
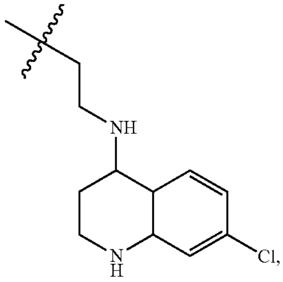 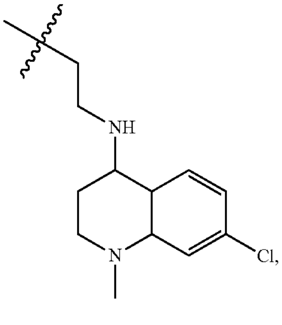

-continued

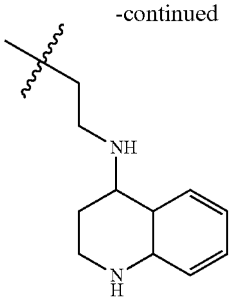

, and

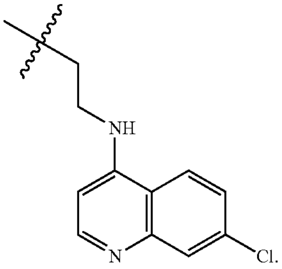

Such embodiments are not limited to a particular definition for $R_3$, $R_4$, $R_5$, and $R_6$.

In some embodiments, each of $R_3$, $R_4$, $R_5$, and $R_6$ is independently selected from hydrogen, fluorine, chlorine, bromine, iodine, hydroxyl, and $NH_2$.

Such embodiments are not limited to a particular definition for $R_7$.

In some embodiments, $R_7$ is selected from hydrogen, methyl, and deuterated methyl (e.g., $CD_3$).

Such embodiments are not limited to a particular definition for $R_8$.

In some embodiments, $R_8$ is selected from hydrogen,

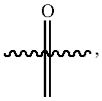

,

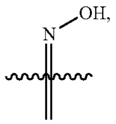

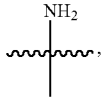

, and

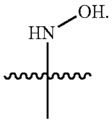

Such embodiments are not limited to a particular definition for $R_9$.

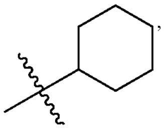

, and

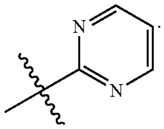

In some embodiments, $R_9$ is selected from hydrogen, methyl,

In some embodiments, the compound is recited in Table 1. Table 1 further includes partition coefficient values for each compound.

In some embodiments, the compound is one or more of the compounds recited in Table 1.

The invention further provides processes for preparing any of the compounds of the present invention.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions.

Autophagy is a type II programmed cell death and can initiate cell death in different circumstances. While autophagy plays an important and helpful role in many cells, in some cases it can result in undesirable damage. This damaging autophagic response have been attributed to many diseases and disorders such as neurodegenerative diseases (see, Fuchs Y, Steller H., Cell 2011; 147: 742-58), cancer, liver diseases (see, Hidvegi et al., Science 2010; 329: 229-32), cardiac diseases (see, Thapalia et al., Int J Clin Exp Pathol. 2014; 7(12):8322-41), metabolic syndromes (see, Codogno et al., Cell Metab 2010; 11: 449-51), diabetes (see, Pareek et al., Curr Med Res Opin 2014; 30: 1257-66), parasitic infection, aging (see, Rubinsztein et al., Cell 2011; 146: 682-95), and inflammation (see, Virgin H W, Levine B. Nat Immunol 2009; 10: 461-70).

A disease or condition that responds favorably to autophagy inhibition is a disease in which autophagy facilitates the progression of the disease or condition, and which is therefore treated by inhibiting autophagy. Examples of diseases or conditions which benefit from the inhibition of autophagy include cancer, diabetes, malaria, schistosomiasis, rheumatoid arthritis, antiphospolipid antibody syndrome, lupus, chronic urticaria, Sjogren's disease, reperfusion injury, and neurodegenerative diseases such as Huntington's disease, Alzheimer's disease, Parkinson's disease, and amyotrophic lateral sclerosis.

In some embodiments, the disease being treated is cancer. Cancer is a disease of abnormal and excessive cell proliferation. Cancer is generally initiated by an environmental insult, certain gene mutations or gene deletions, or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of malignant cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system.

Examples of types of cancer that can be treated using the compounds of the present invention include cancer is selected from the group consisting carcinomas (e.g., squamous-cell carcinomas, adenocarcinomas, hepatocellular carcinomas, and renal cell carcinomas), particularly those of the bladder, bone, bowel, breast, cervix, colon (colorectal), esophagus, head, kidney, liver, lung, nasopharyngeal, neck, ovary, pancreas, prostate, and stomach; leukemias, such as acute myclogenous leukemia, acute lymphocytic leukemia, acute promyelocytic leukemia (APL), acute T-cell lymphoblastic leukemia, adult T-cell leukemia, basophilic leukemia, eosinophilic leukemia, granulocytic leukemia, hairy cell leukemia, leukopenic leukemia, lymphatic leukemia, lynphoblastic leukemia, lymphocytic leukemia, megakaryocytic leukemia, micromyeloblastic leukemia, monocytic leukemia, neutrophilic leukemia and stem cell leukemia; benign and malignant lymphomas, particularly Burkitt's lymphoma, Non-Hodgkin's lymphoma and B-cell lymphoma; benign and malignant melanomas; myeloproliterative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germline tumors (e.g., bowel cancer, breast cancer, prostate cancer, cervical cancer, uterine cancer, lung cancer (e.g., small cell lung cancer, mixed small cell and non-small cell cancer, pleural mesothelioma, including metastatic pleural mnesothelioma small cell lung cancer and non-small cell lung cancer), ovarian cancer, testicular cancer, thyroid cancer, astrocytoma, esophageal cancer, pancreatic cancer, stomach cancer, liver cancer, colon cancer, and melanoma; mixed types of neoplasias, particularly carcinosarcoma and Hodgkin's disease; and tumors of mixed origin, such as Wilms' tumor and teratocarcinomas, among others. Certain epithelial tumors including ovarian, breast, colon, head and neck, medulloblastoma and B-cell lymphoma, among others are shown to exhibit increased autophagy and are principal target cancers for the autophagy inhibitors of the present invention in some embodiments, while in other embodiments the cancer is leukemia or acute myeloid leukemia.

In some embodiments, the method further comprises administration of an additional anticancer agent. An additional anticancer agent is known anticancer agent that can be co-administered with one or more compounds of the present invention for cancer treatment. Co-administration can either be simultaneous, or proximal in time. Examples of anticancer agents include angiogenesis inhibitors such as angiostatin KI-3, DL-α-difluoromethyl-omithine, endostatin, fumagillin, genistein, minocycline, staurosporine, and (±)-thalidomide; DNA intercalating or cross-linking agents such as bleomycin, carboplatin, carmustine, chlorambucil, cyclophosphamide, cisplatin, phenanthriplatin, meiphalan, mitoxantrone, and oxaliplatin; DNA synthesis inhibitors such as methotrexate, 3-Amino-1,2,4-henzotriazine 1,4-dioxide, aminopterin, cytosine β-D-arabinofuranoside, 5-Fluoro-5'-deoxyuridine, S-Fluorouracil, gaciclovir, hydroxyurea, and mitomycin C; DNA-RNA transcription regulators such as actinomycin D, daunorubicin, doxorubicin, homoharringtonine, and idarubicin; enzyme inhibitors such as S(+)-camptothecin, curcumin, (−)-deguelin, 5,6-dichlorobenz-imidazole 1-βD-ribofuranoside, etoposine, formestane, fistriecin, hispidin, cyclocreatine, mevinolin, trichostatin A, tyrophostin AG 34, and tyrophostin AG 879, Gene Regulating agents such as 5-aza-2'-deoxycitidine, azacitidine, decitabine, cholecalciferol, 4-hydroxytamoxifen, melatonin, mifepristone, raloxifene, all trans-retinal, all trans retinoic acid, 9-cis-retinoic acid, retinol, tamoxifen, and troglitazone; Microtubule Inhibitors such as colchicine, dolostatin 15, nocodazole, paclitaxel, podophyllotoxin, rhizoxin, vinblastine, vincristine, vindesine, and vinorelbine; and various other antitumor agents such as 17-(allylamino)-17-demethoxygeldanamycin, 4-Amino-1,8-naphthalimide, apigenin, brefeldin A, cimetidine, dichloromethylene-diphosphonic acid, leuprolide, luteinizing-hormone-releasing hormone, pifithrin-α, rapamycin, thapsigargin, and bikunin, and derivatives thereof.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that received a vehicle that does not contain the test agent. Transgenic animal models are also available and are commonly accepted as models for human disease (see, for instance. Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof.

Another aspect of the invention provides a method of inhibiting autophagy in cells of a subject, comprising contacting the cells with an effective amount of a compound recited herein.

Autophagy is a highly regulated process of biological systems that plays a normal part in cell growth development and homeostasis helping to maintain a balance between the synthesis, degradation, and subsequent recycling of cellular products. It is a major mechanism by which a cell allocates nutrients from unnecessary processes to more-essential processes.

A number of autophagic processes occur in nature, all of which have the degradation of intracellular components via the lysosome as a common feature. A well-known mechanism of autophagy involves the formation of a membrane around a targeted region of a cell, separating the contents from the rest of the cytoplasm. The resultant vesicle then fuses with a lysosome which subsequently degrades the contents.

Autophagy consists of the sequestration of organelles and proteins in autophagic vesicles (AV) and degradation of this cargo through lysosomal fusion. Autophagy allows tumor cells to survive metabolic and therapeutic stresses. Multiple publications by those skilled in the art indicate therapy-induced autophagy is a key resistance mechanism to many anti-cancer agents.

The present invention includes methods of inhibiting autophagy in a cell, particularly the cell of a subject. The methods can be used to inhibit autophagy in a cell in various environments. For example, in some embodiments, the cells are contacted in vivo, while in other embodiments the cells are contacted in vitro or ex vivo. The resulting inhibition of authophagy can be monitored or applied in the cell to evaluate effectiveness of the agent, effect a favorable result such as treatment of a disease or condition involving autophagy, or to study the effect of inhibition of autophagy in the cell.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

FIG. 1 shows cell viability analysis for several compounds of the invention. In particular, FIG. 1 shows the activity of SAHA, lucanthone, HCQ, ROC-325, and novel autophagy inhibitors in the MOLM-13 AML model. MOLM-13 cells were treated with the indicated concentrations of drugs for 72 hours and cell viability was determined by MTT assay. Mean±SD, n=4.

Example II

This example provides a synthesis scheme utilized in the development of compounds described herein.

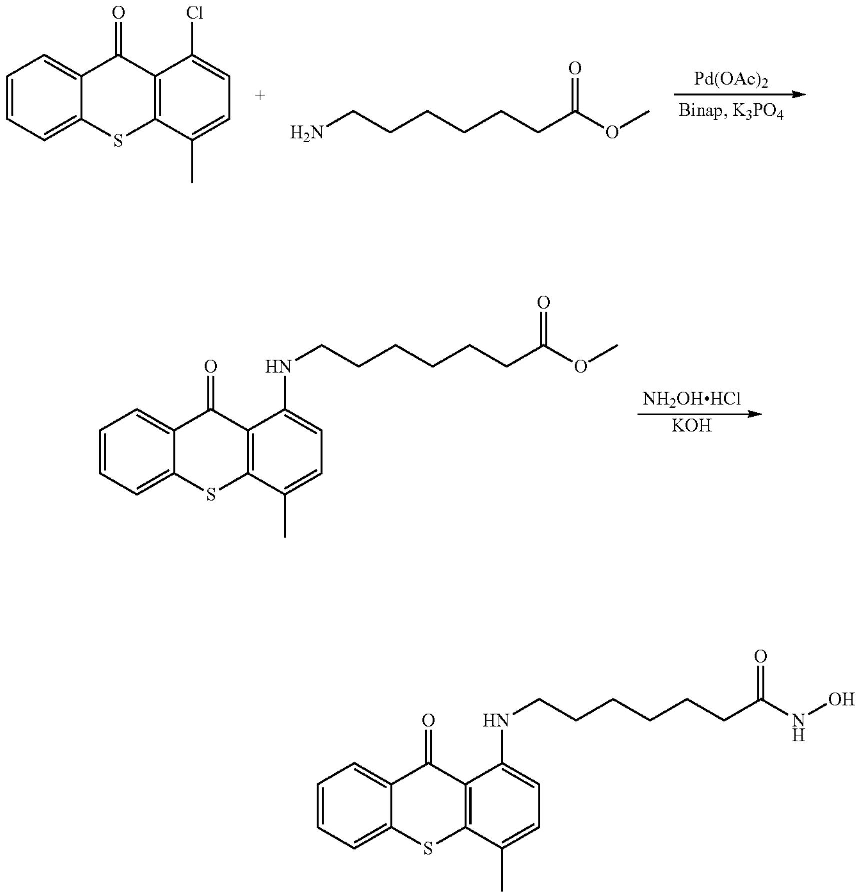

H1

-continued
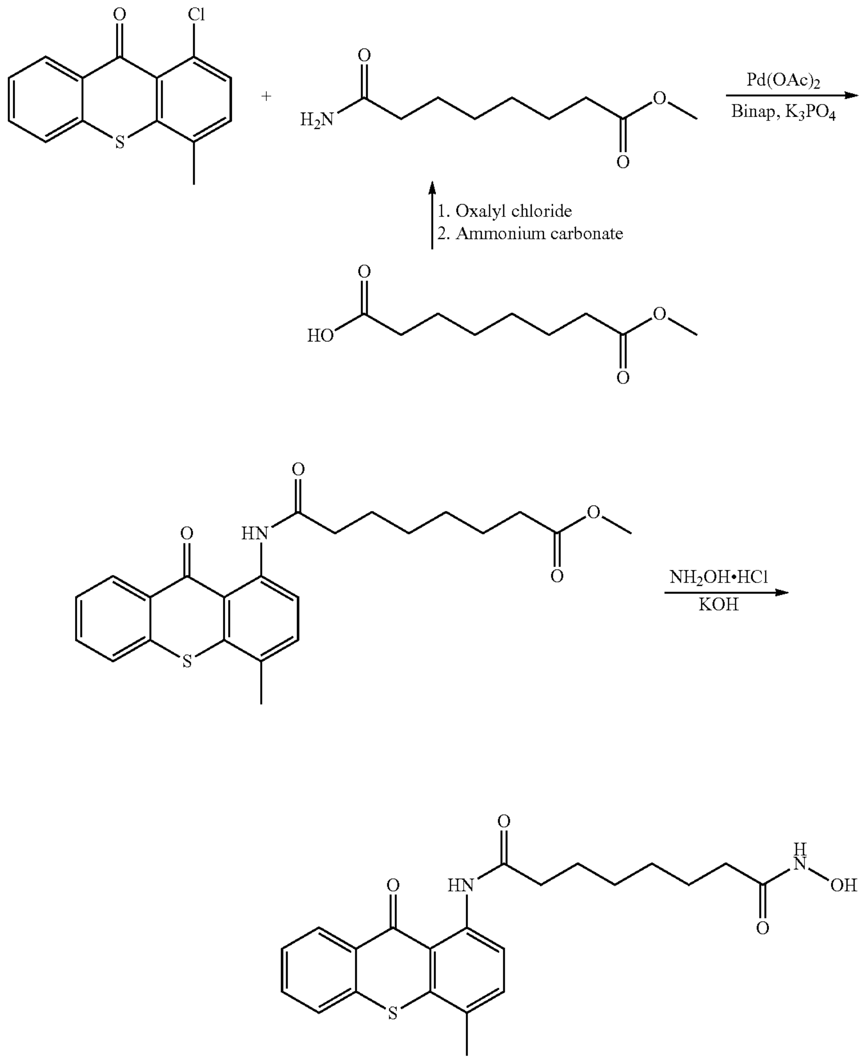
H2
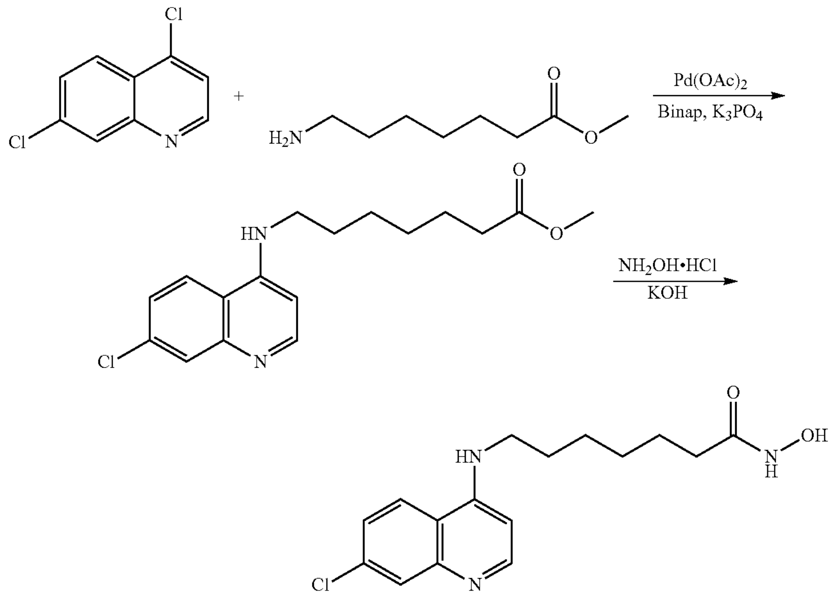
H10

-continued
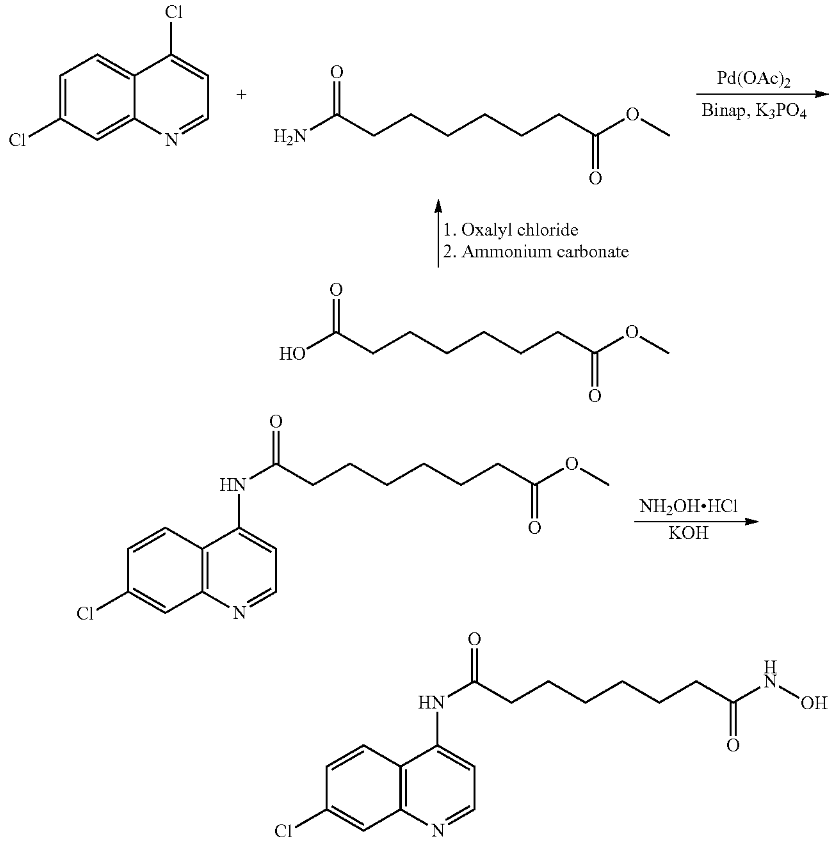
H11
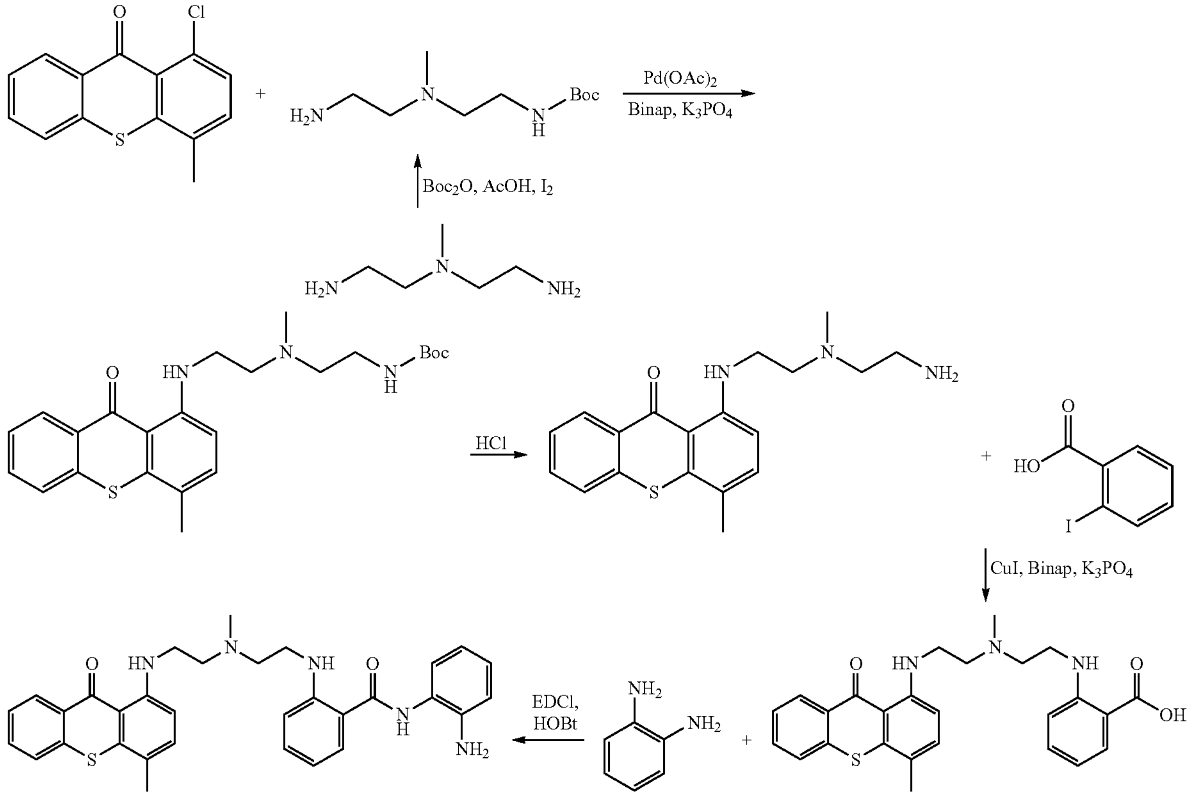
H7

Example III
This example provides a synthesis scheme utilized in the development of compounds described herein.
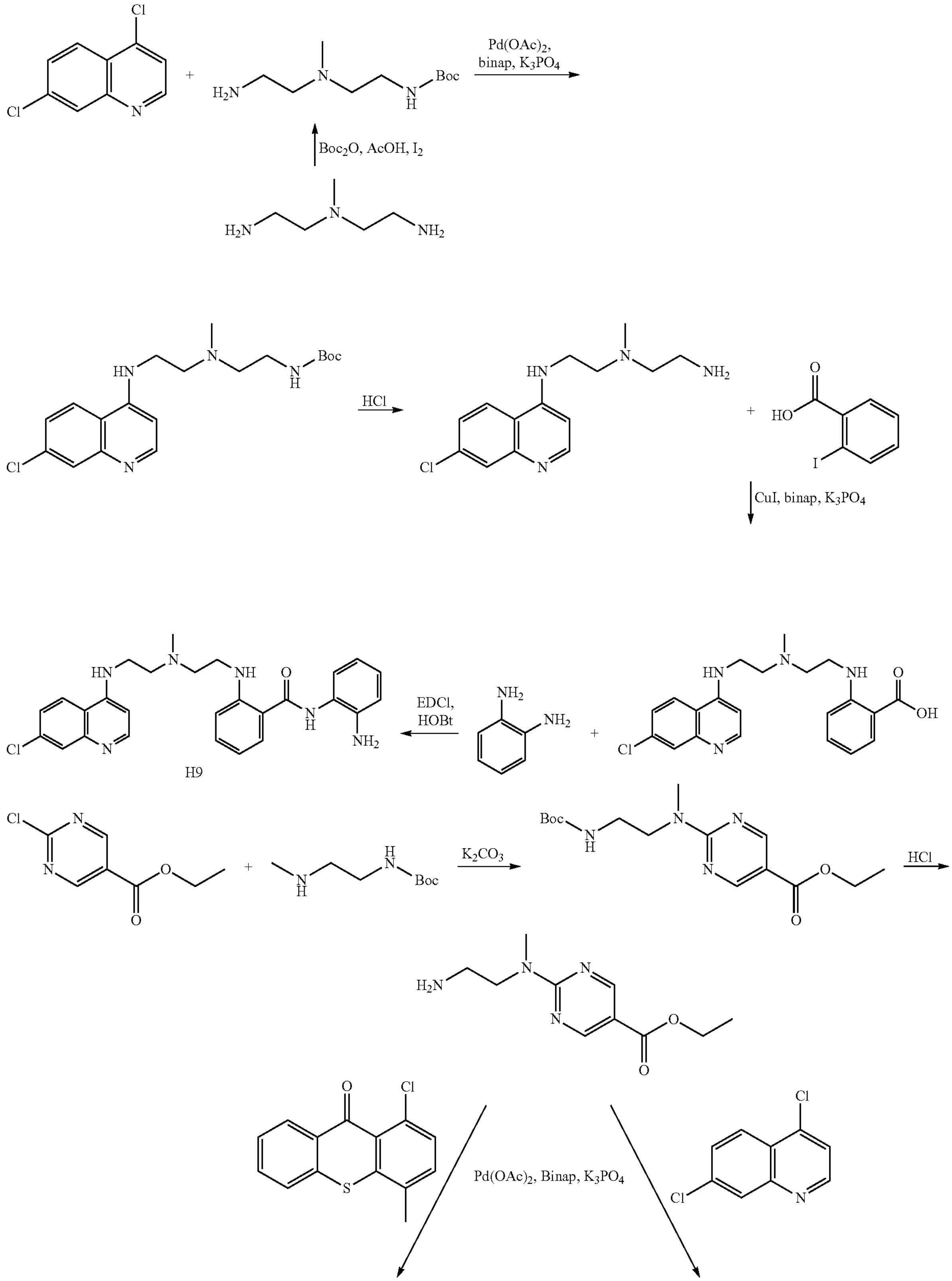

-continued
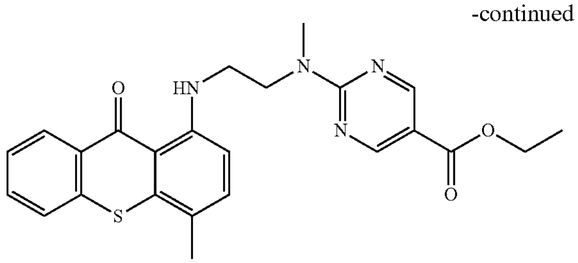
H6
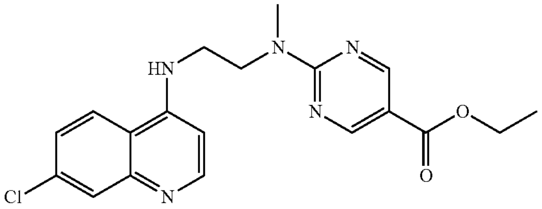
H8
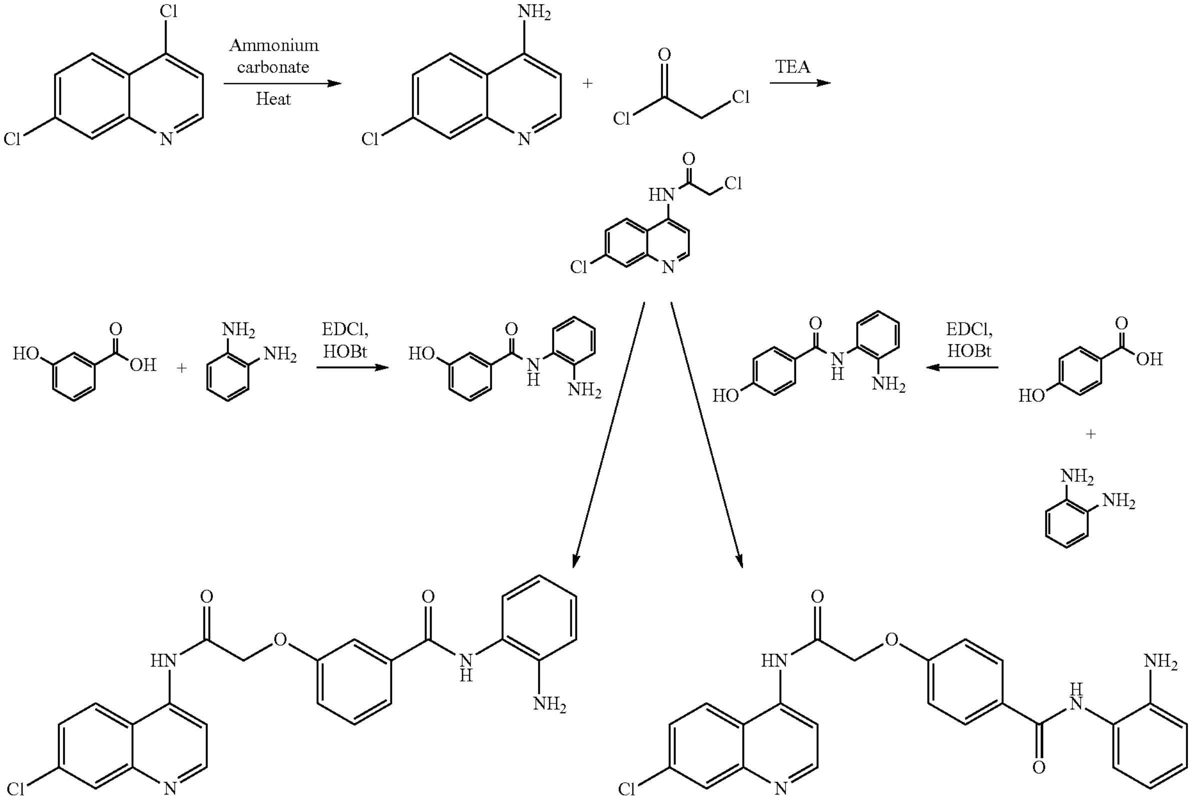
BFC-01-158 (H12)
BFC-01-159 (H13)
Example IV
This example provides a synthesis scheme utilized in the development of compounds described herein.
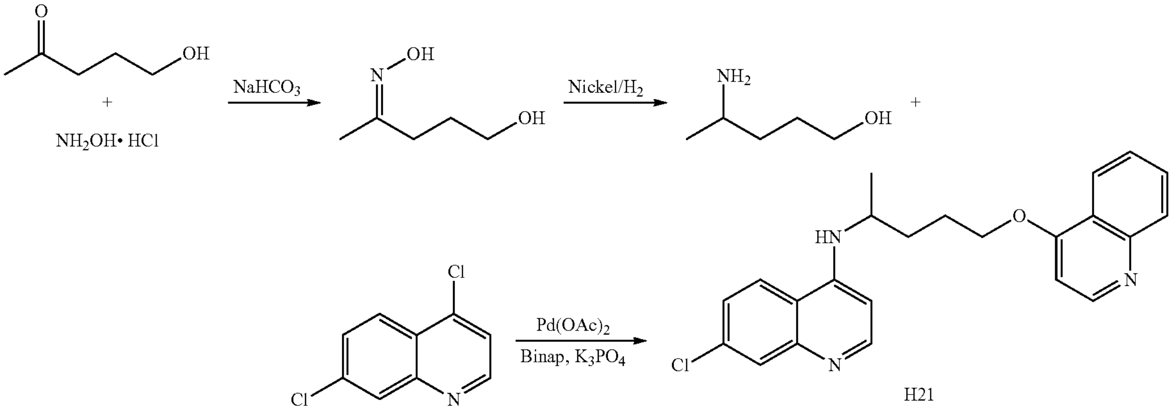
H21

-continued
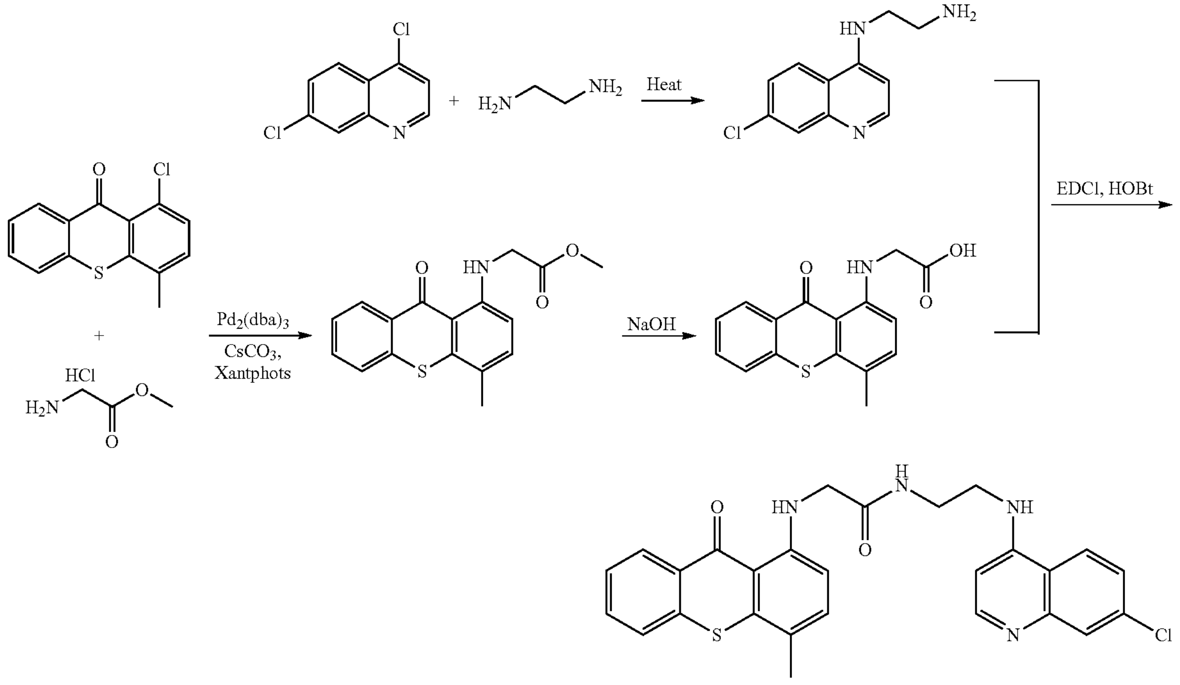
H22
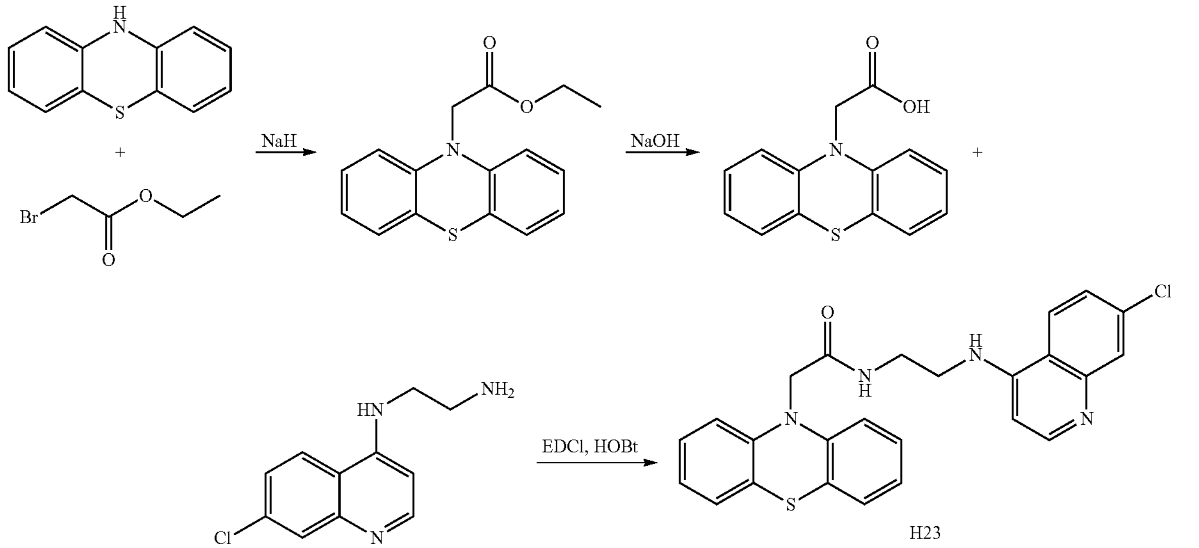
H23
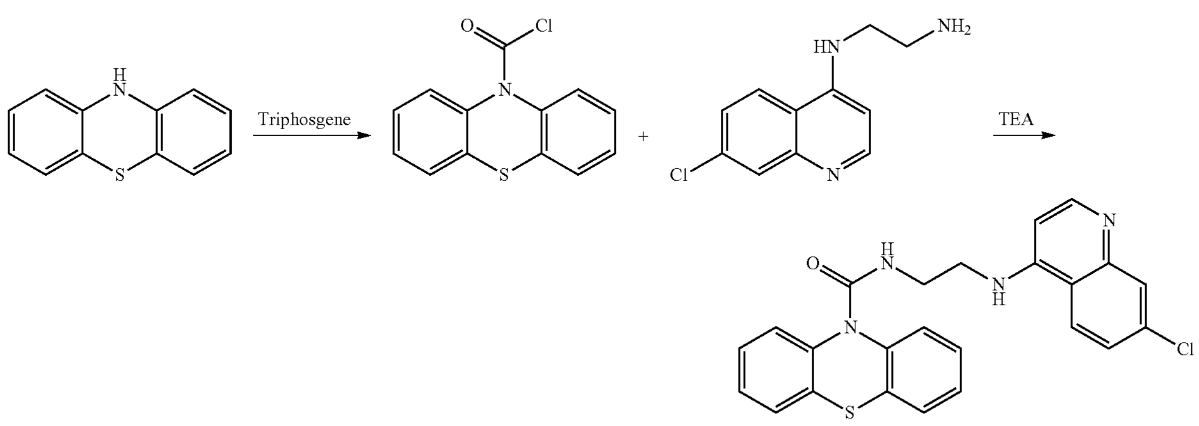
H24

-continued

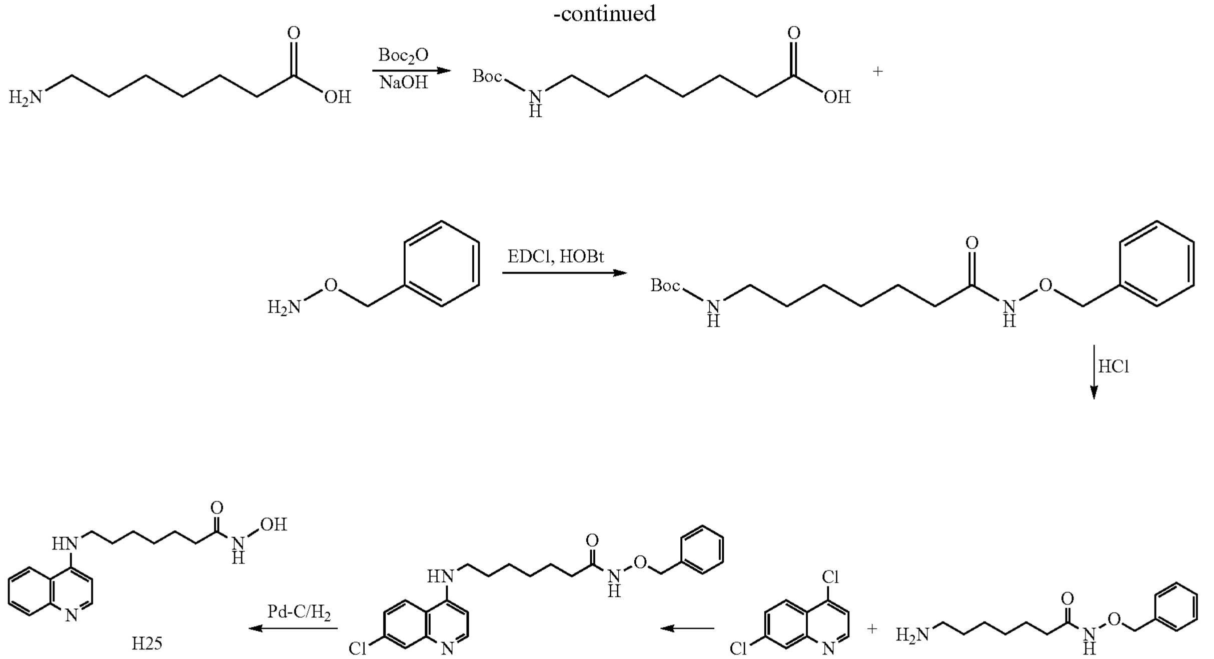

H25

INCORPORATION BY REFERENCE

The entire disclosure of each of the patent documents and scientific articles referred to herein is incorporated by reference for all purposes. The following references are herein incorporated by reference in their entireties:

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:

1. A compound encompassed within one of the following formulas:

(Formula II)

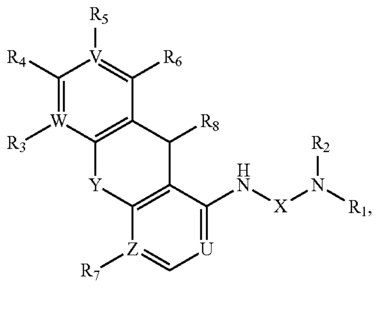

and

-continued (Formula IV)

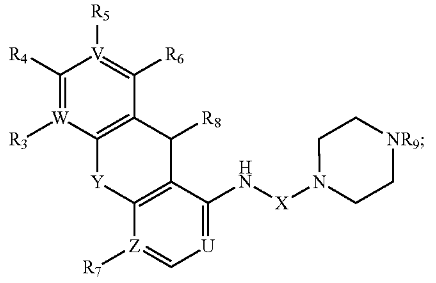

or a pharmaceutically acceptable salt, solvate, or prodrug thereof, wherein U is selected from carbon and nitrogen;

wherein V is selected from carbon and nitrogen;

wherein W is selected from carbon and nitrogen;

wherein X is selected from

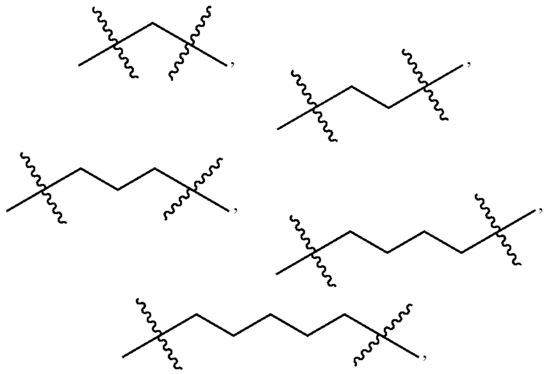

-continued
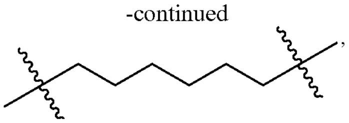,
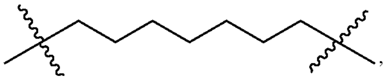,
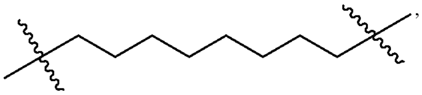,
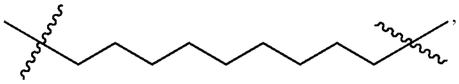,
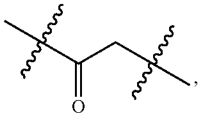,
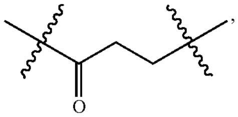,
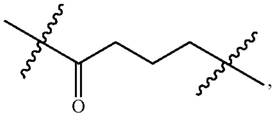,
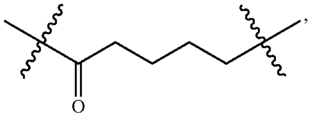,
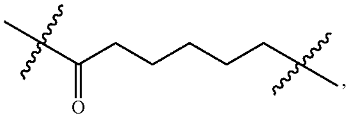,
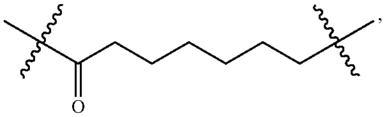,
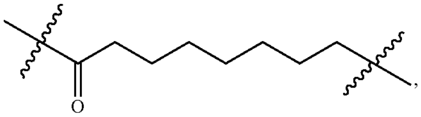,
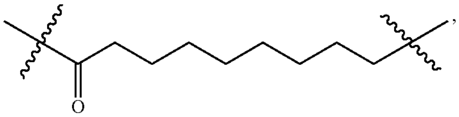,
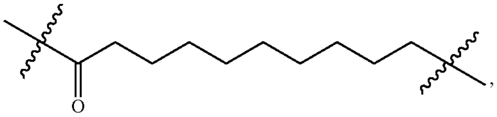,
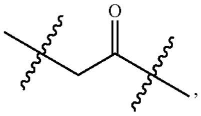,
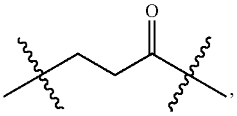,
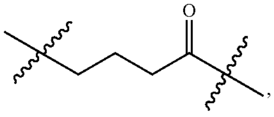,
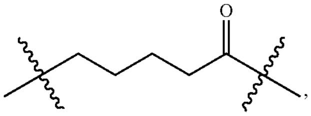,
-continued
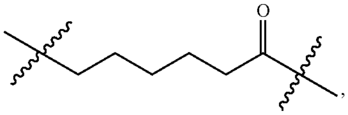,
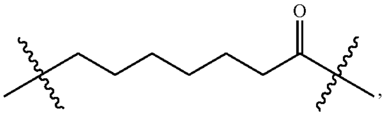,
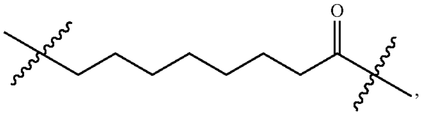,
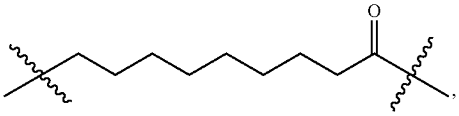,
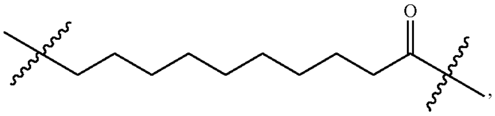,
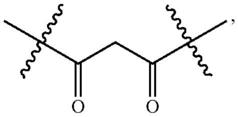,
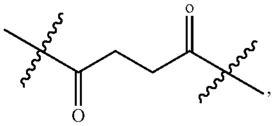,
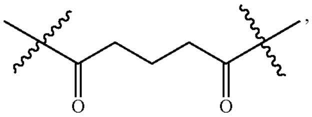,
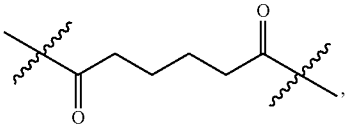,
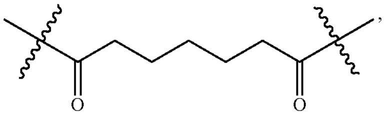,
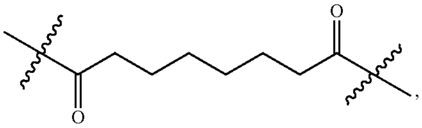,
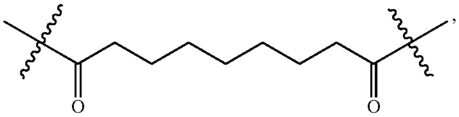,
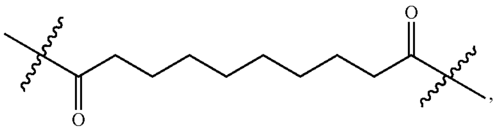,
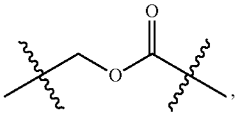,
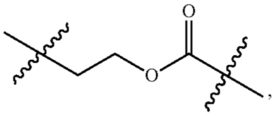, -continued
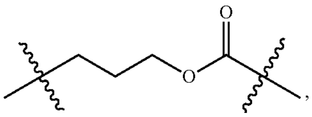
,
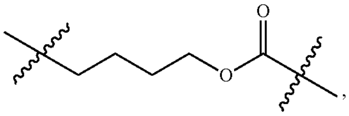
,
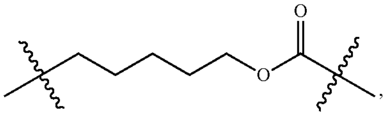
,
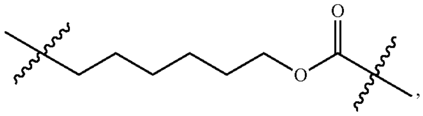
,
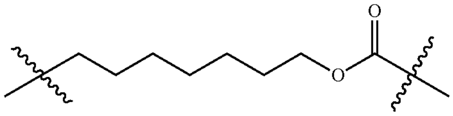
, and
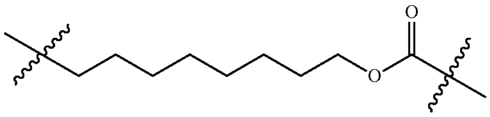
;
wherein Y is selected from S, NH, $NCH_3$, and oxygen; wherein Z is selected from carbon and nitrogen; wherein $R_1$ is selected from hydroxyl,
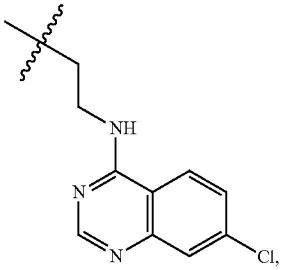
,
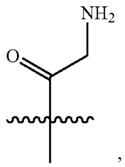
,
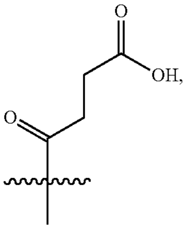
,
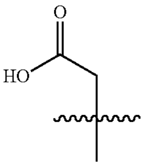
,
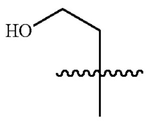
,
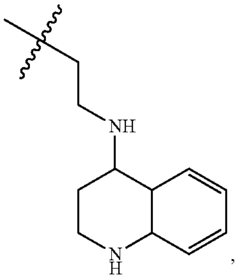
,
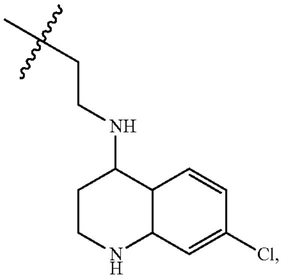
,
-continued
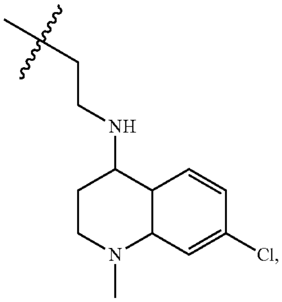
,
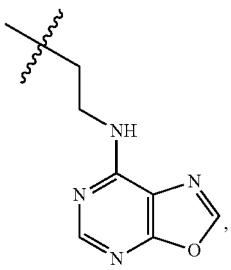
,
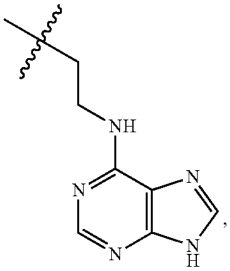
,
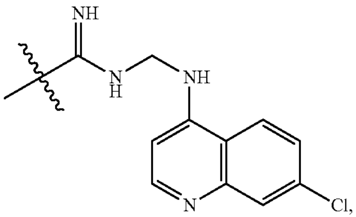
,
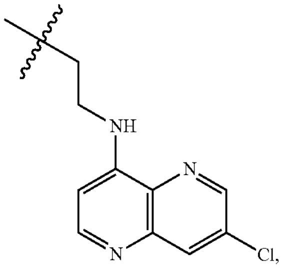
,
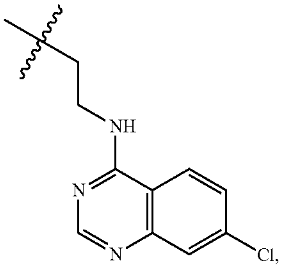
,
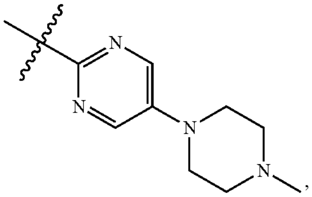
, -continued
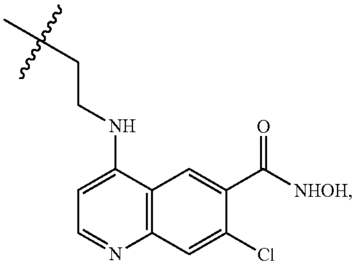
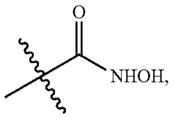
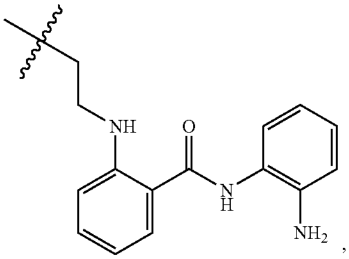
,
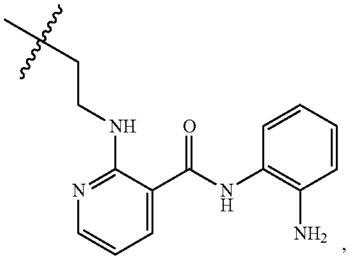
,
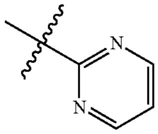
,
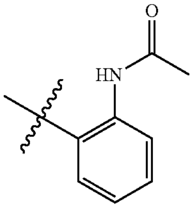
,
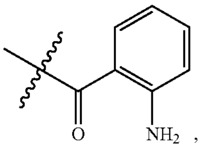
,
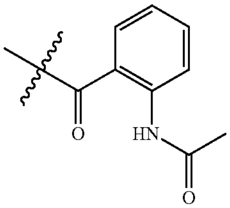
,
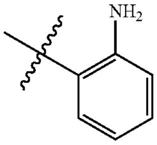
,
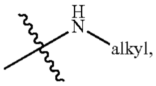
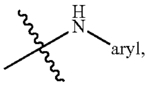
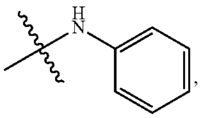
,
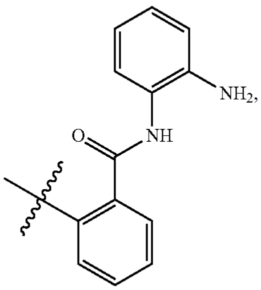
-continued
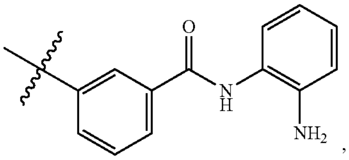
,
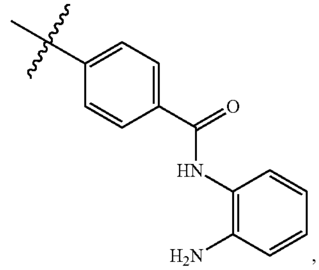
,
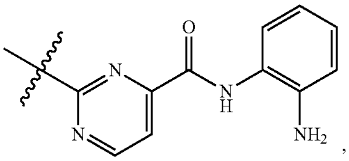
,
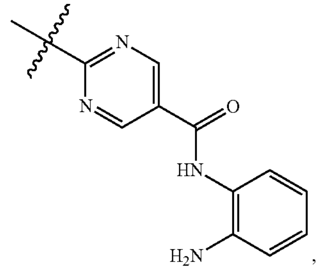
,
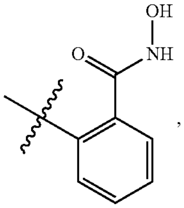
,
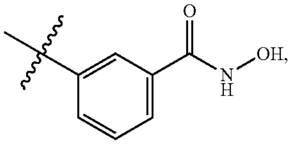
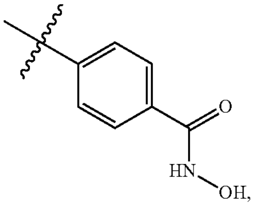
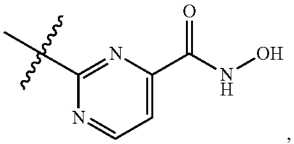
,
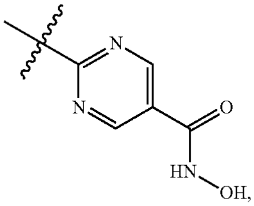
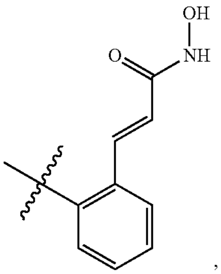
,
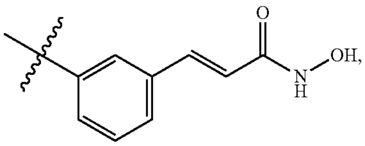

-continued
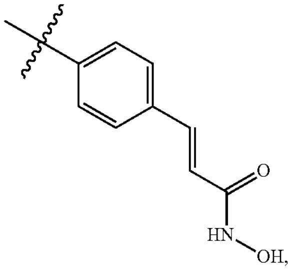
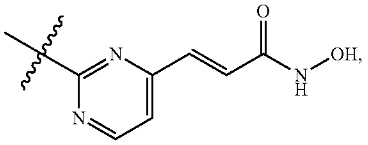
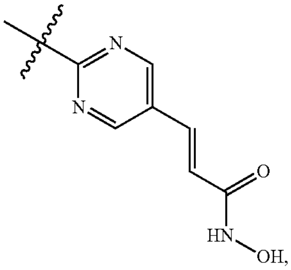
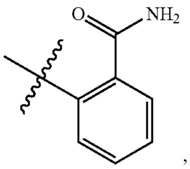
,
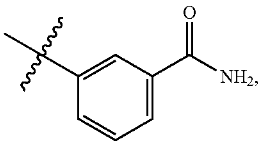
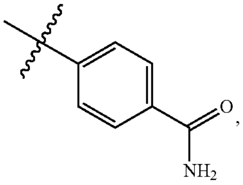
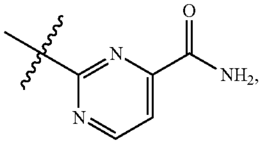
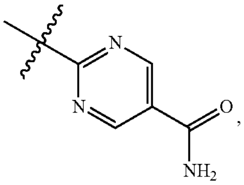
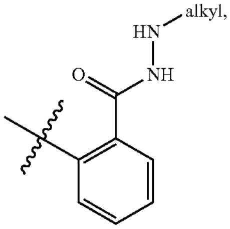
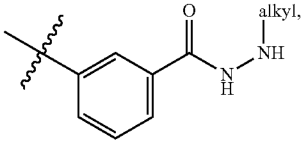
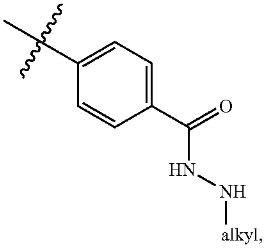
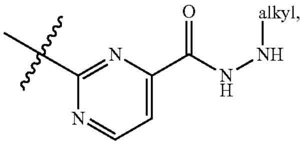
-continued
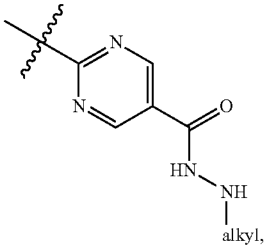
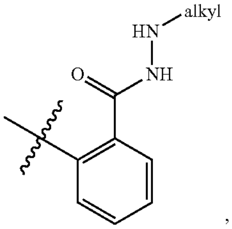
,
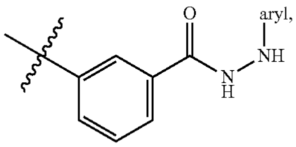
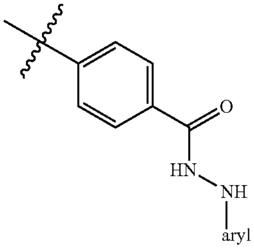
,
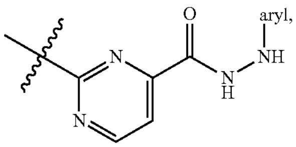
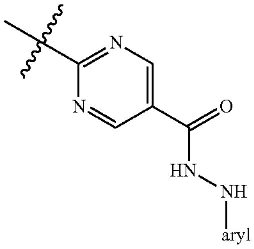
,
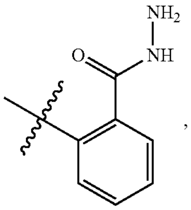
,
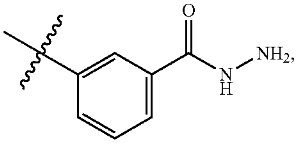
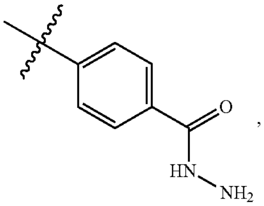
,
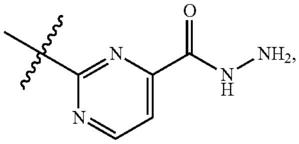
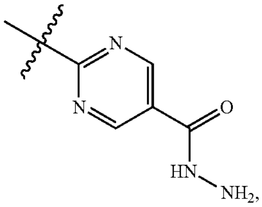
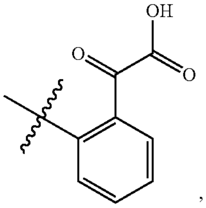
,
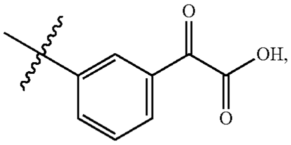
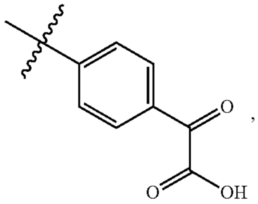
,
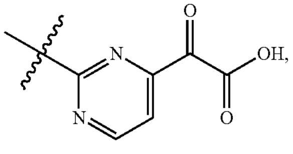

-continued

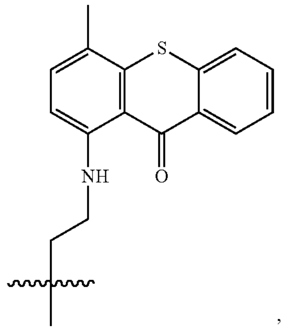

,

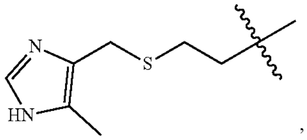

,

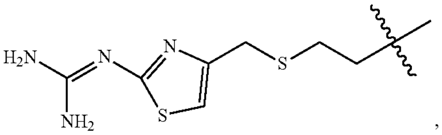

, and

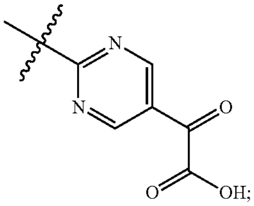

wherein $R_2$ is selected from hydrogen, methyl,

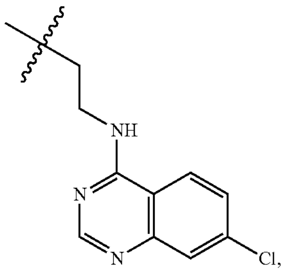

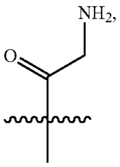

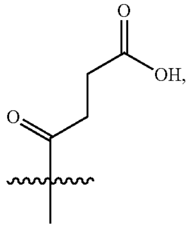

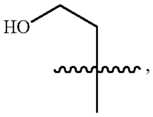

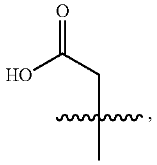

-continued

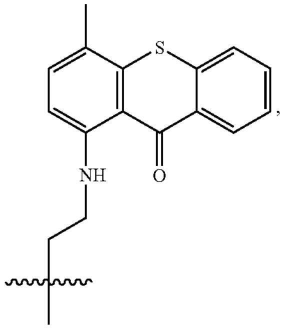

,

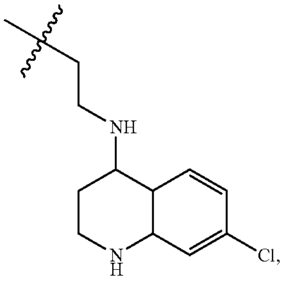

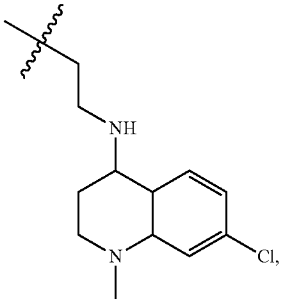

and

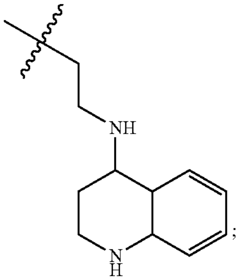

wherein each of $R_3$, $R_4$, $R_5$, and $R_6$ is independently selected from hydrogen, fluorine, chlorine, bromine, iodine, hydroxyl, and $NH_2$;

wherein $R_7$ is selected from hydrogen, methyl, and deuterated methyl;

wherein $R_8$ is selected from hydrogen,

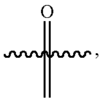

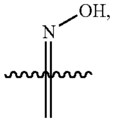

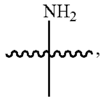

and

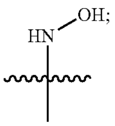

wherein $R_9$ is selected from hydrogen, methyl,

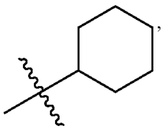

, and

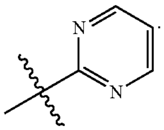

2. The compound of claim 1, wherein said compound is selected from the group of
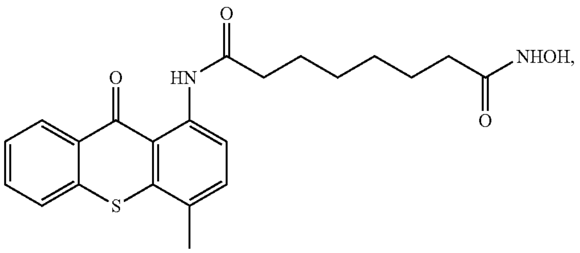
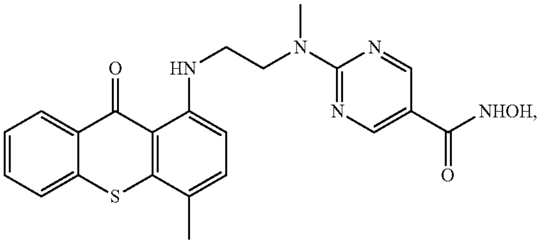
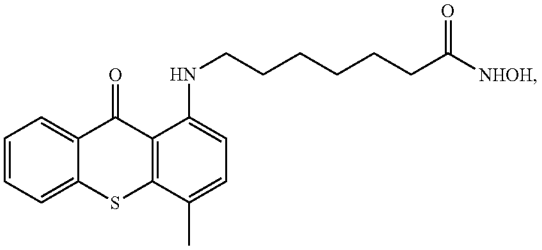
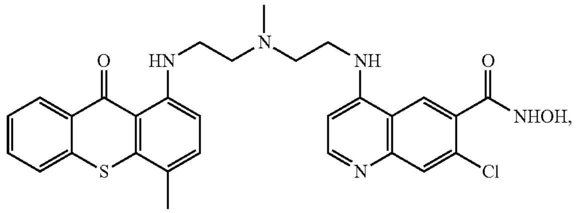
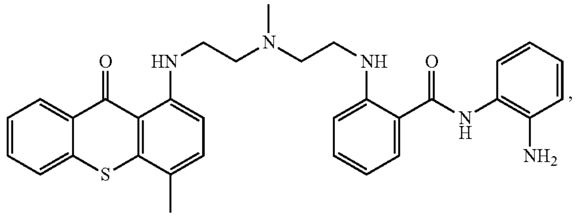
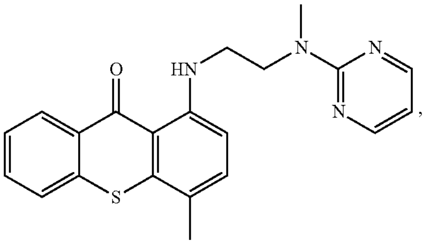
-continued
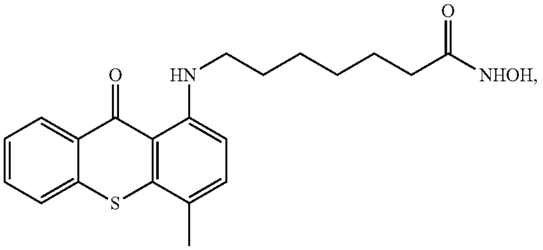
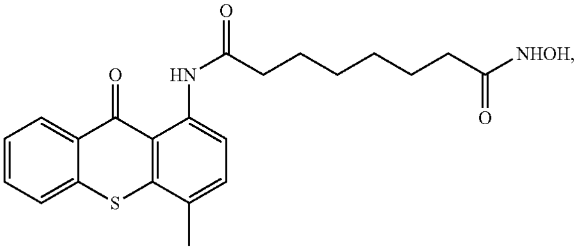
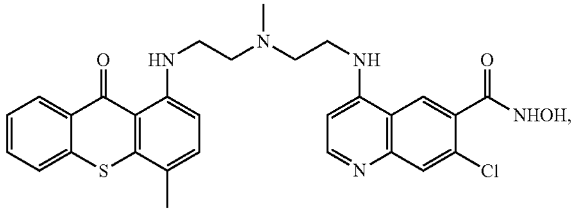
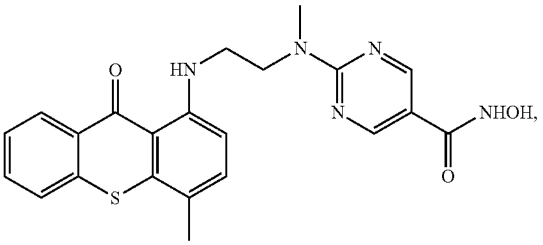
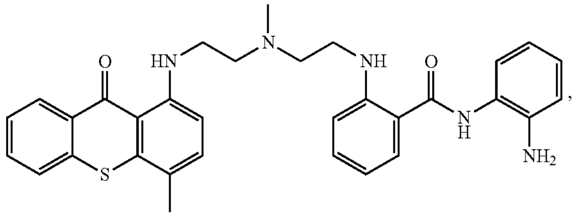
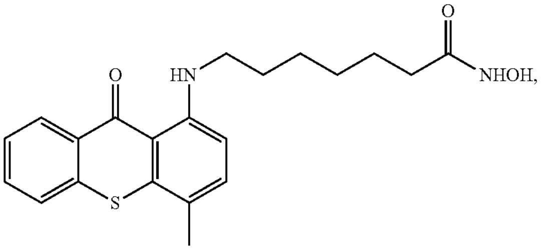
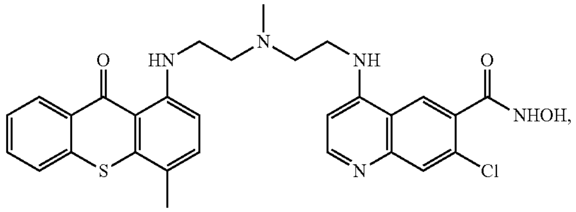

-continued
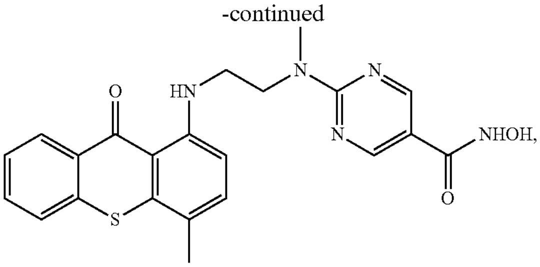
,
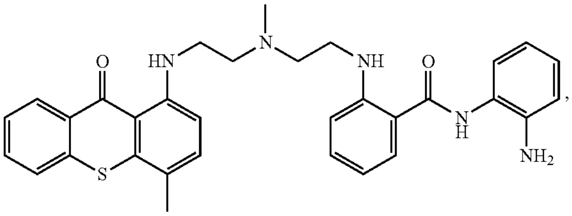
,
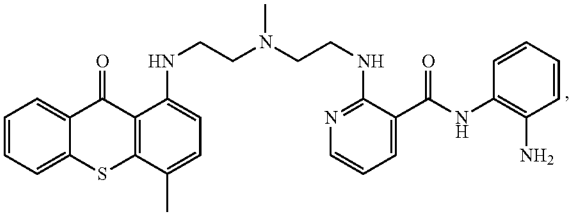
,
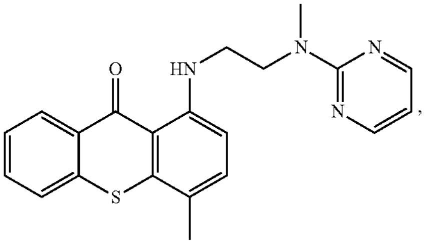
,
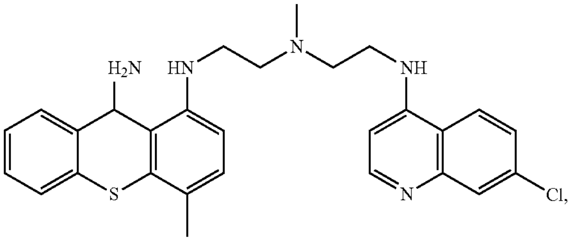
,
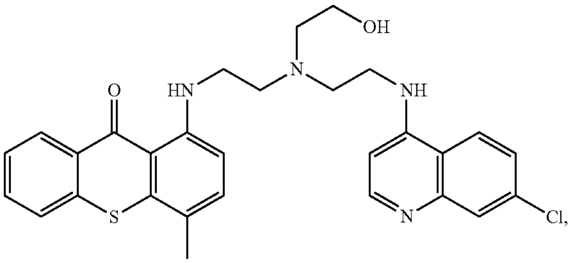
,
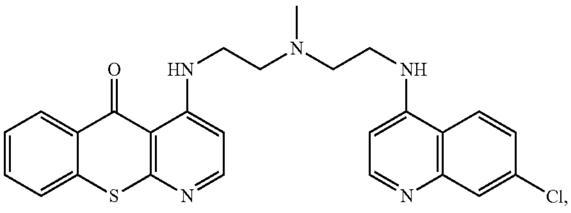
,
-continued
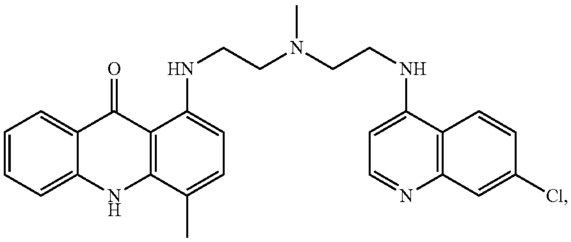
,
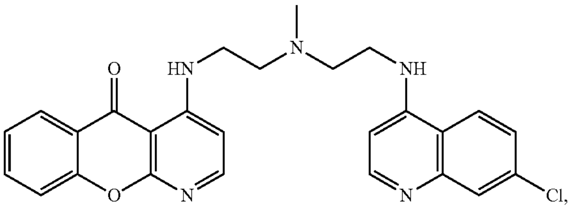
,
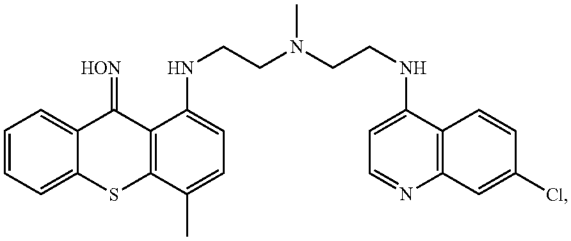
,
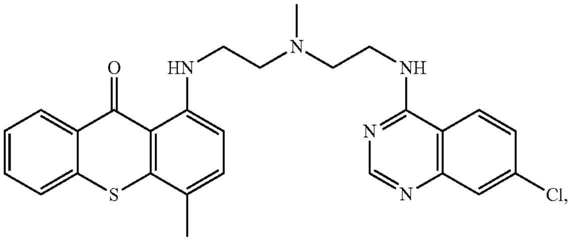
,
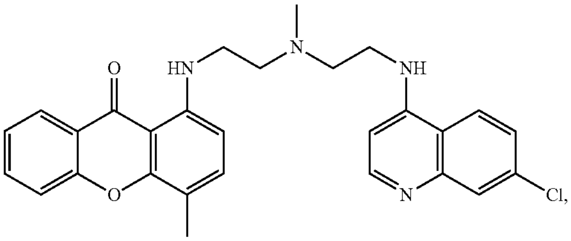
,
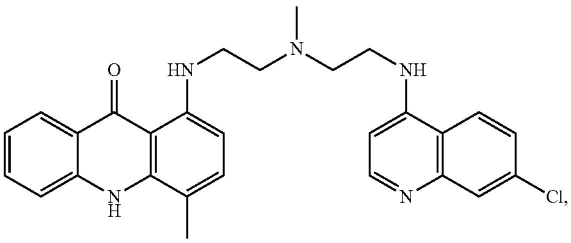
,
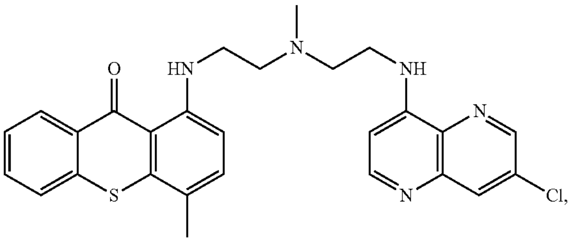
, -continued
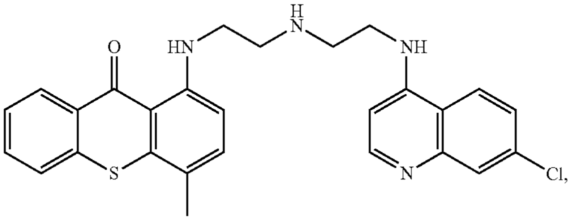
,
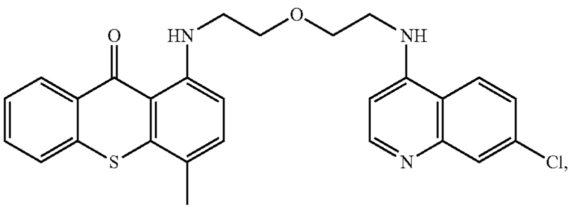
,
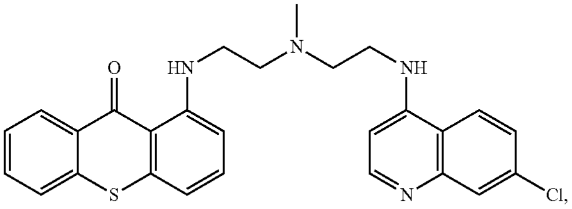
,
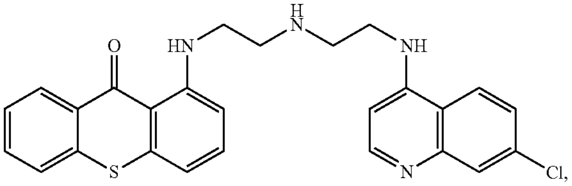
,
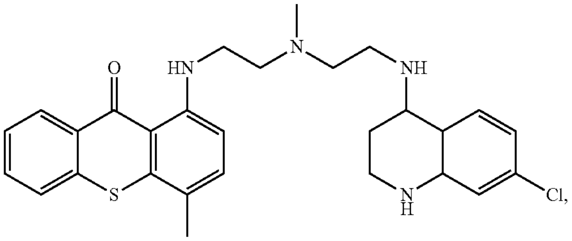
,
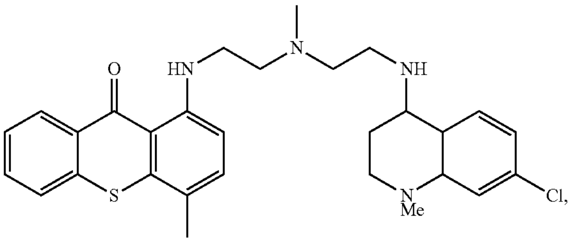
,
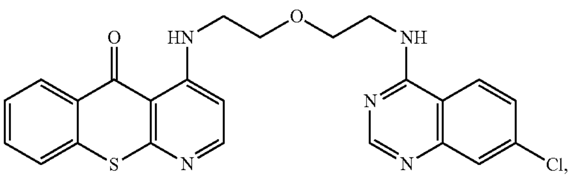
,
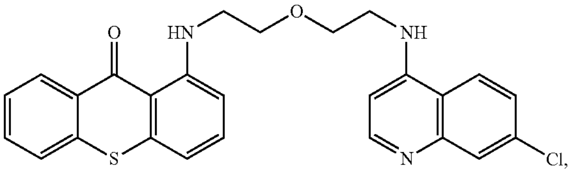
,
-continued
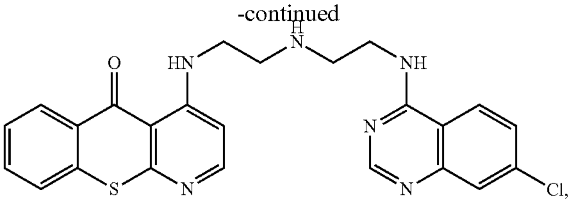
,
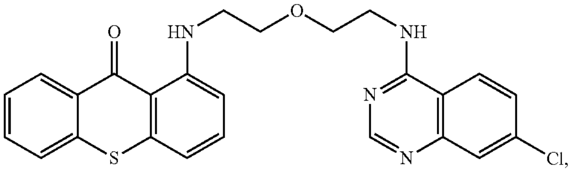
,
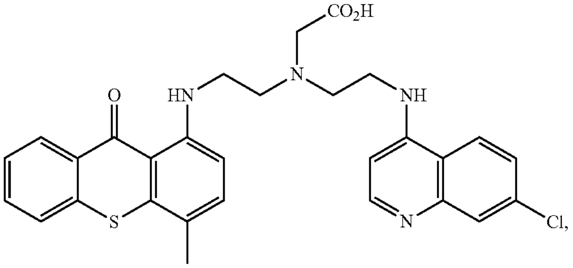
,
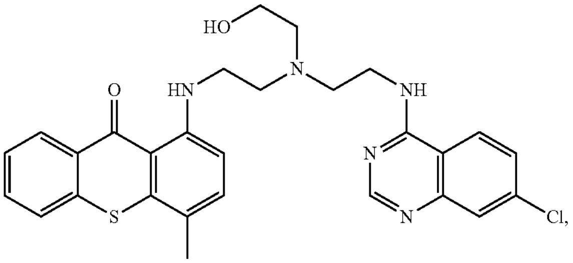
,
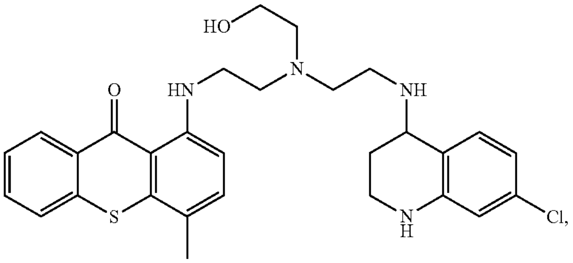
,
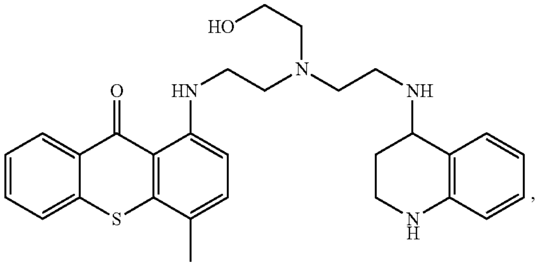
,
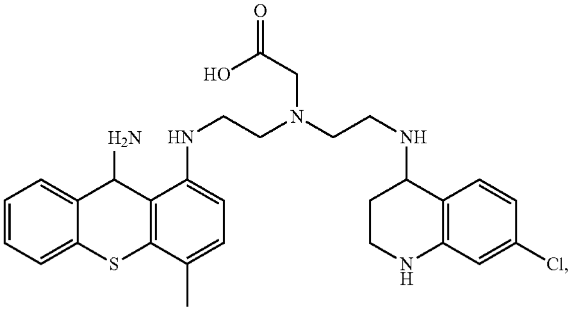
, -continued
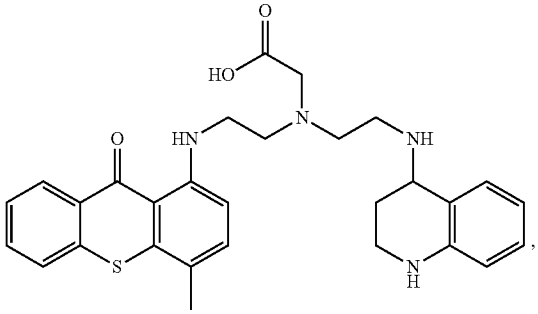
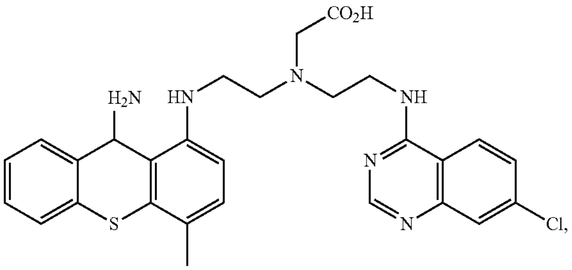
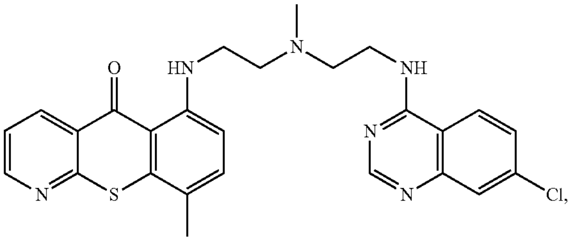
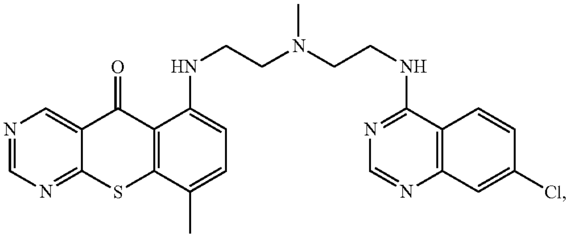
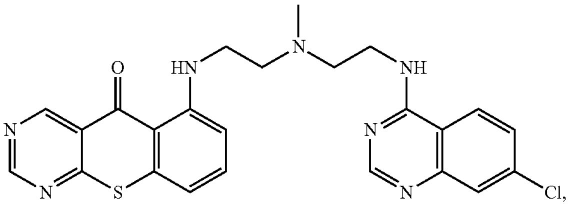
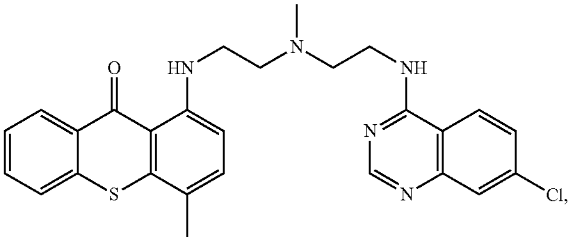
-continued
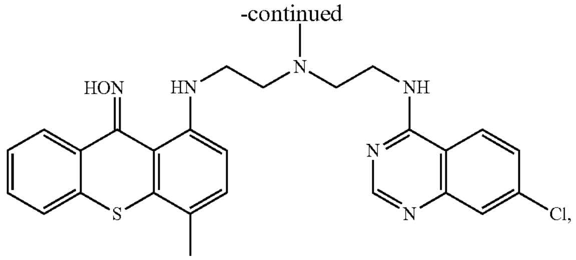
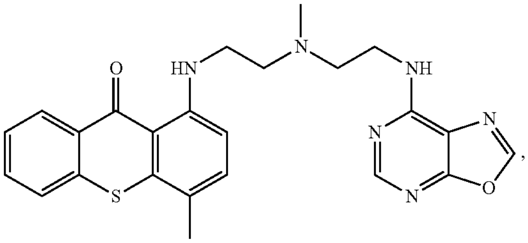
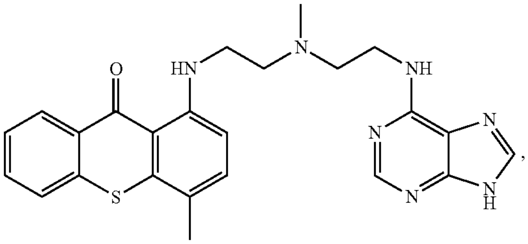
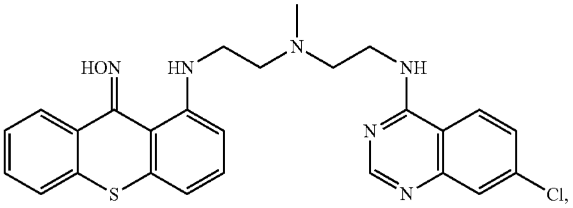
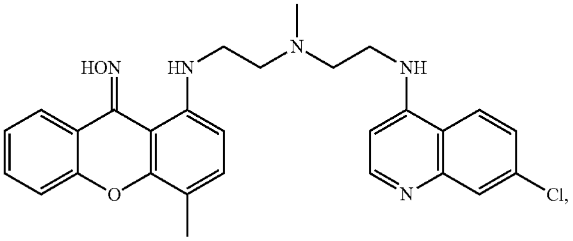
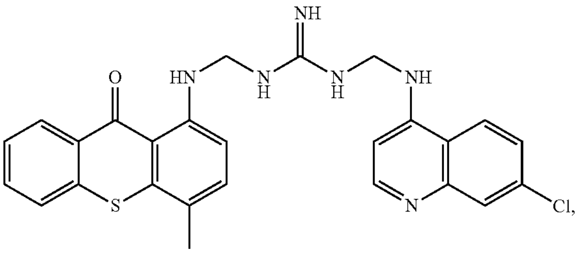

-continued
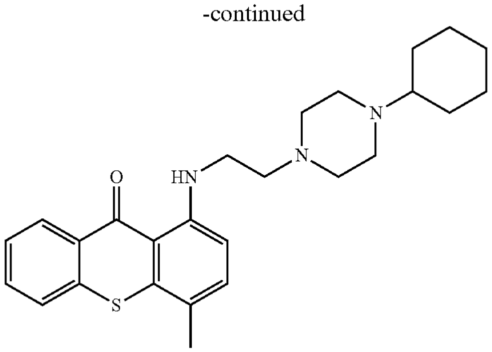
,
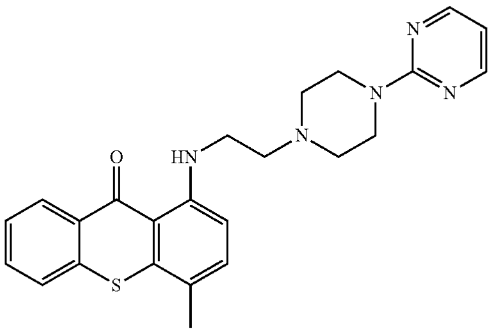
,
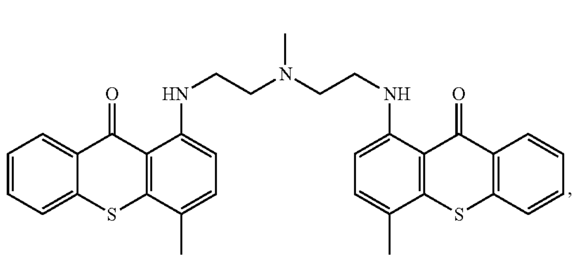
,
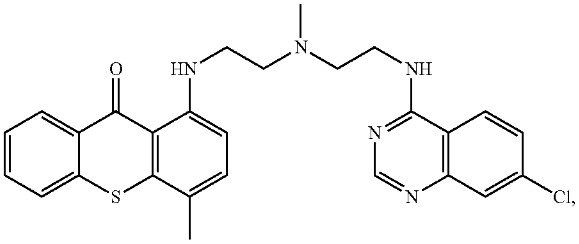
,
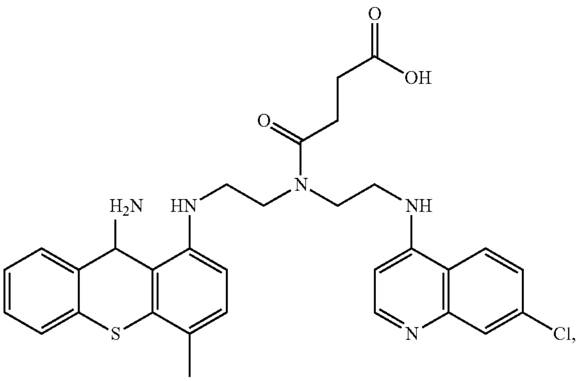
,
-continued
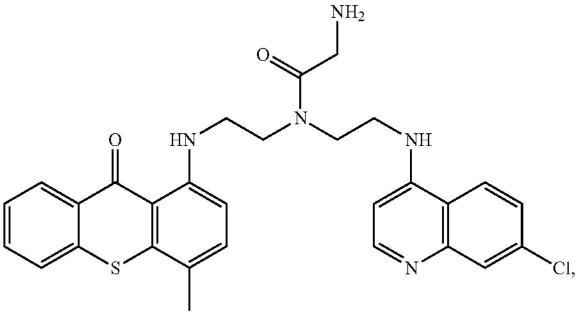
,
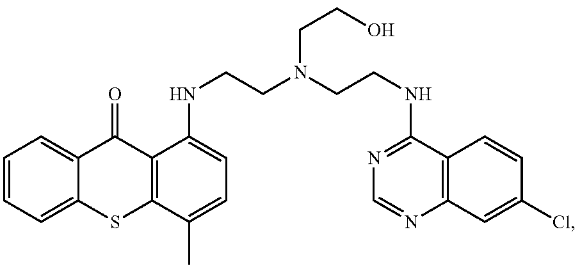
,
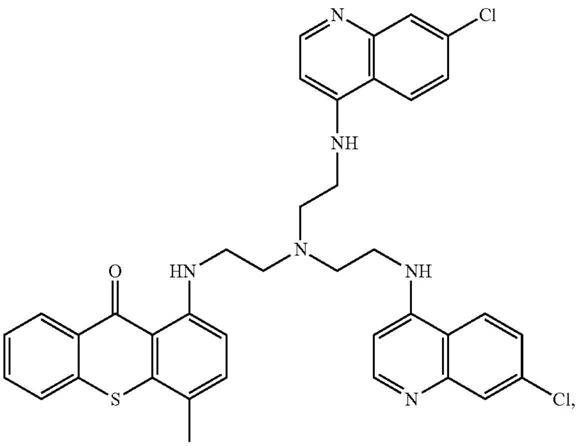
,
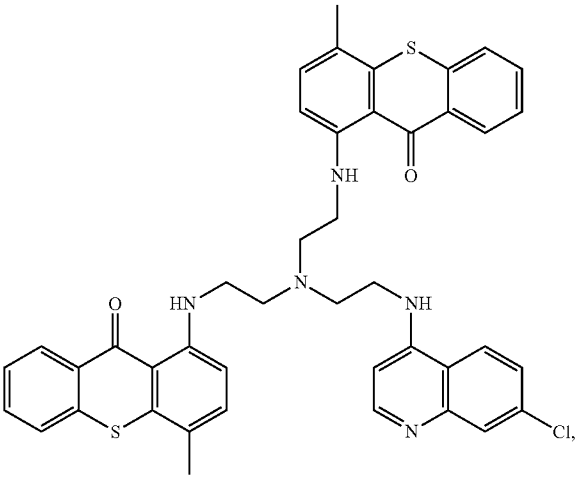
, -continued
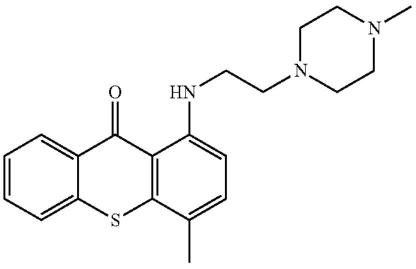
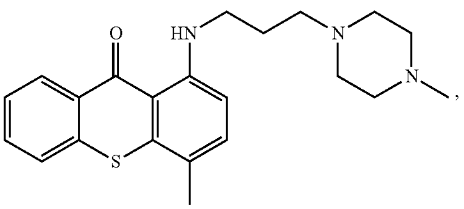
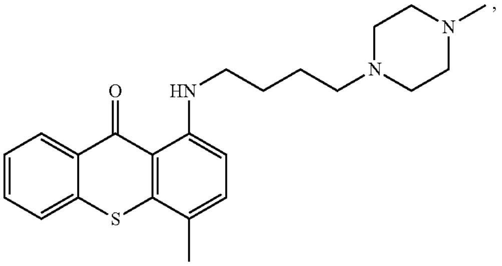
and
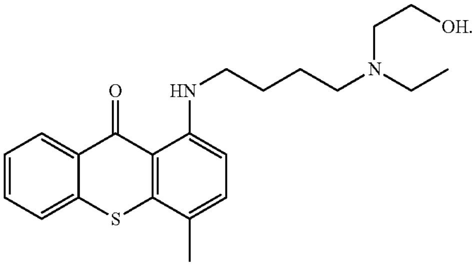
3. A compound selected from the group of
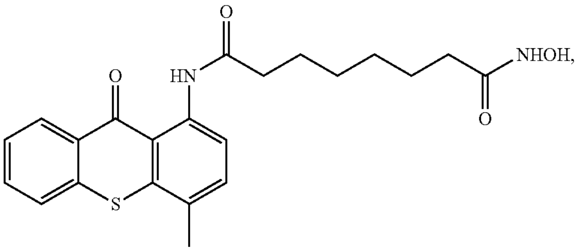
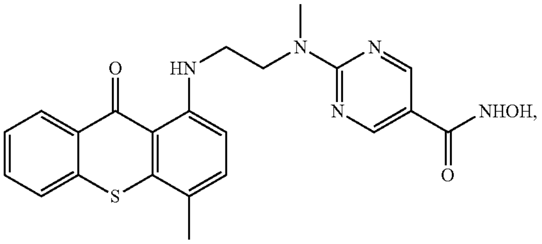
-continued
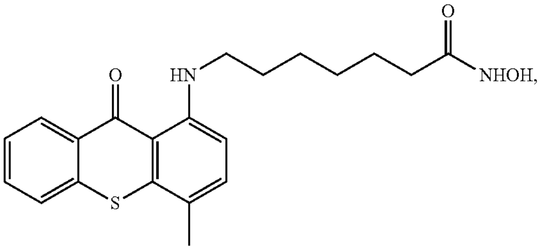
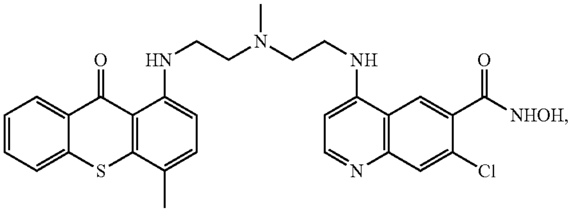
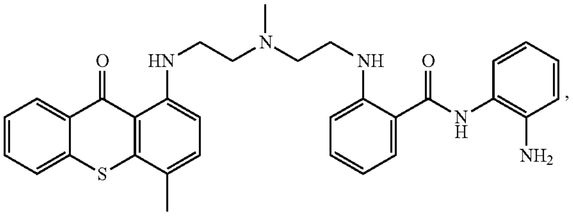
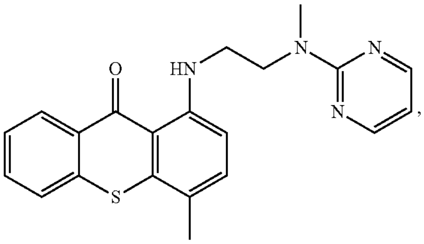
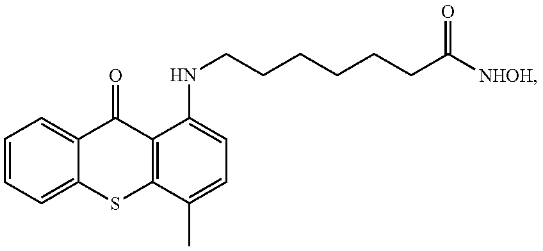
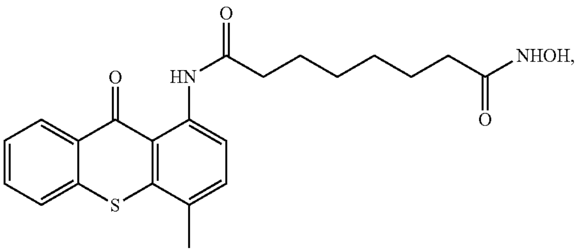
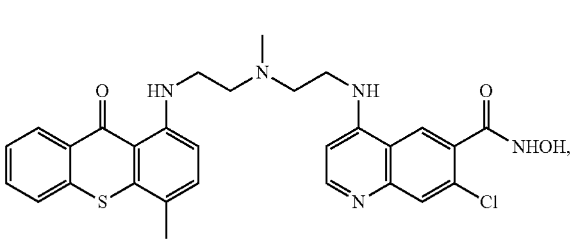

-continued
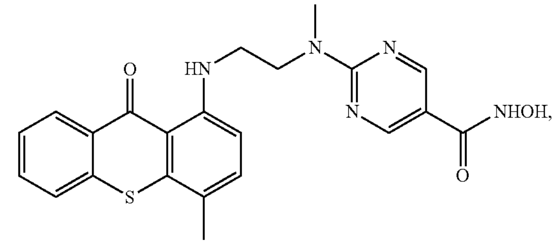
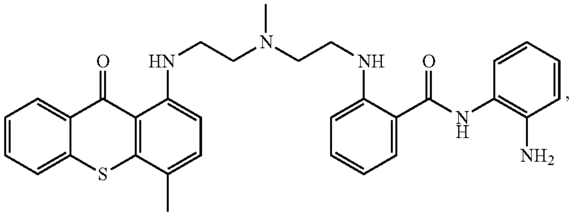
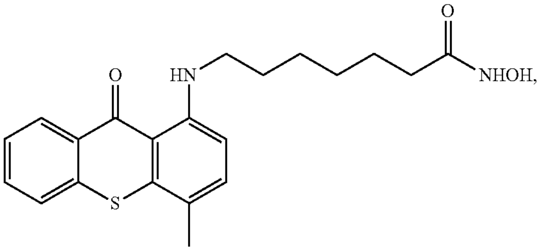
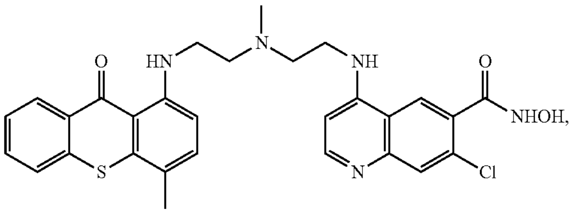
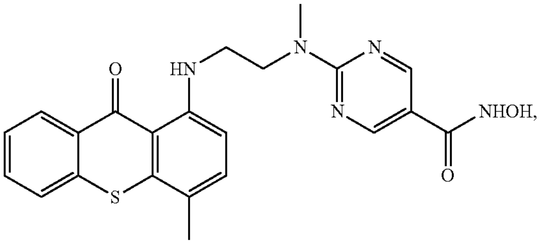
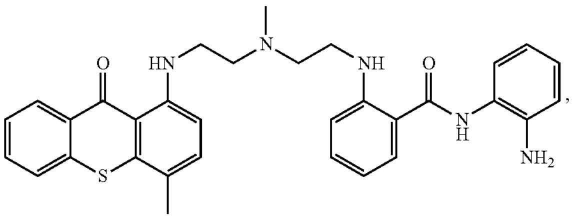
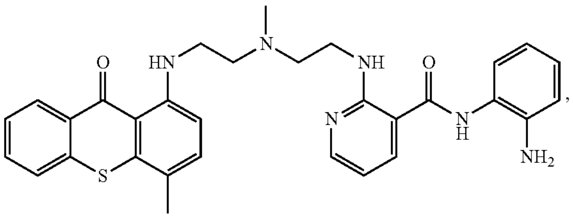
-continued
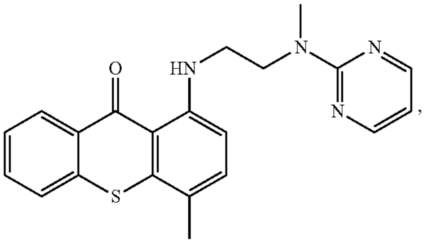
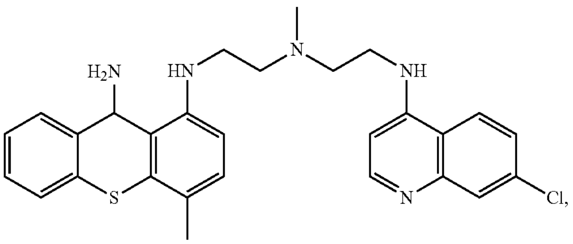
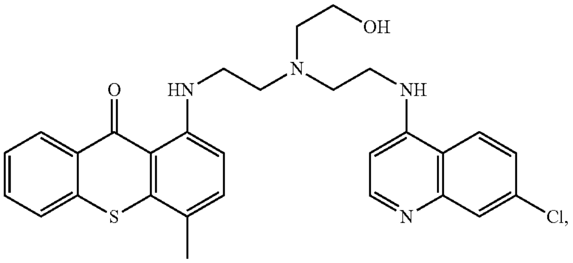
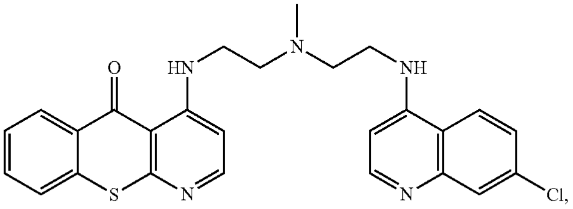
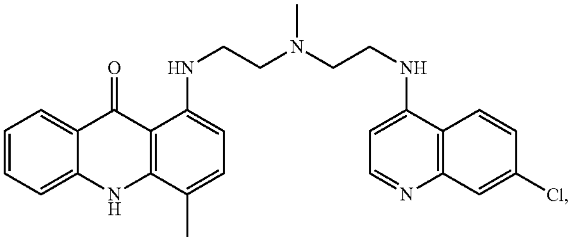
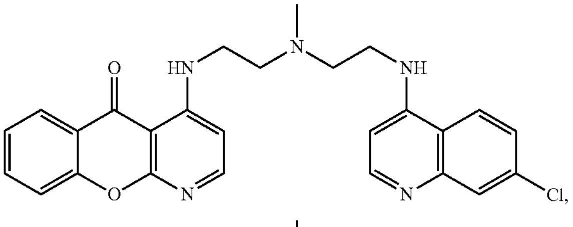
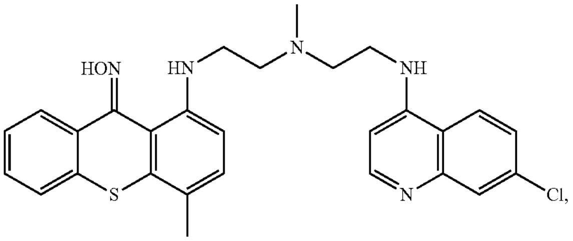

-continued
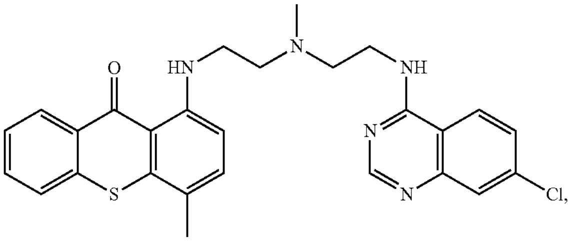
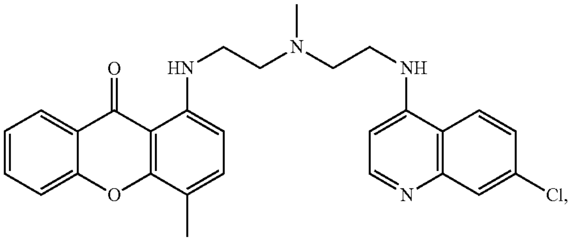
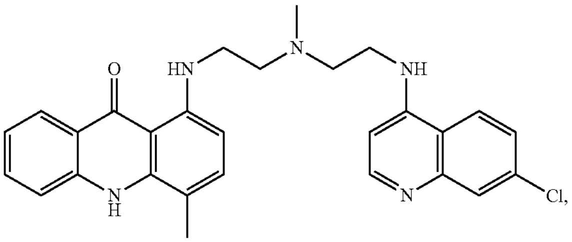
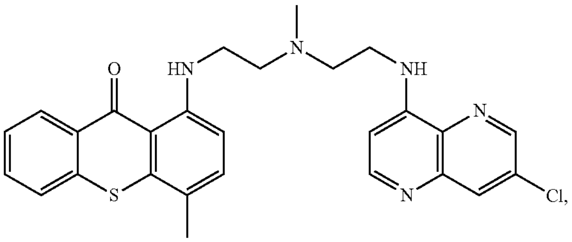
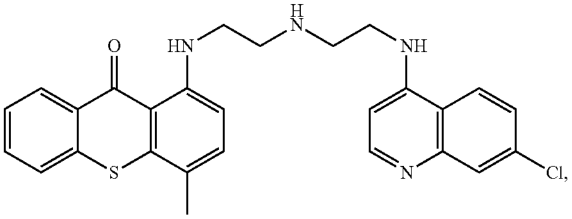
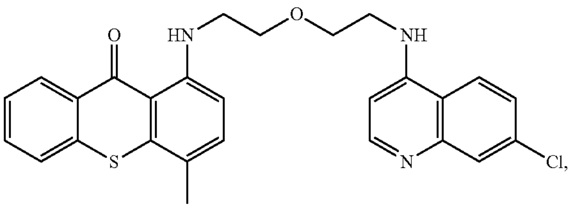
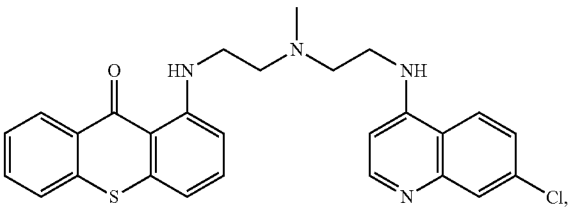
-continued
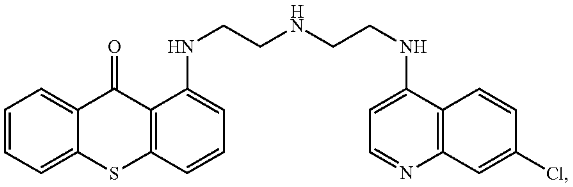
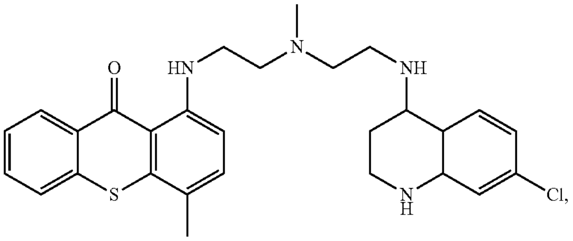
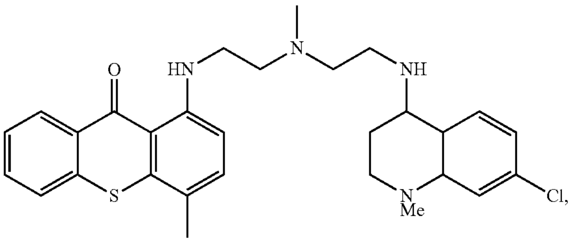
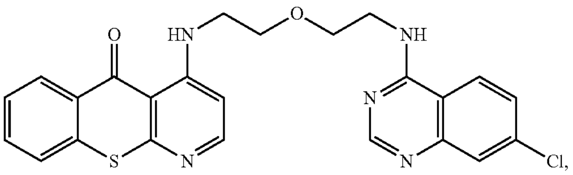
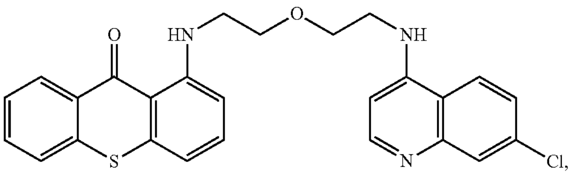
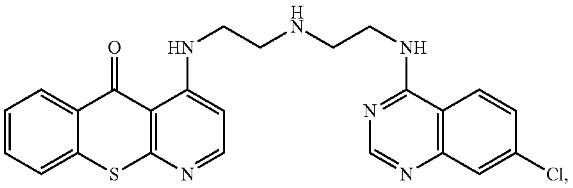
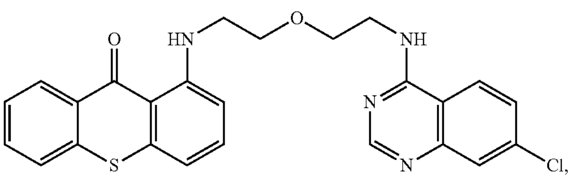
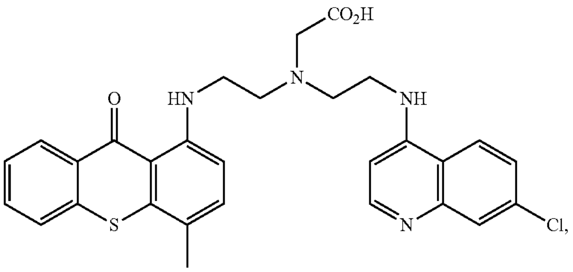

-continued
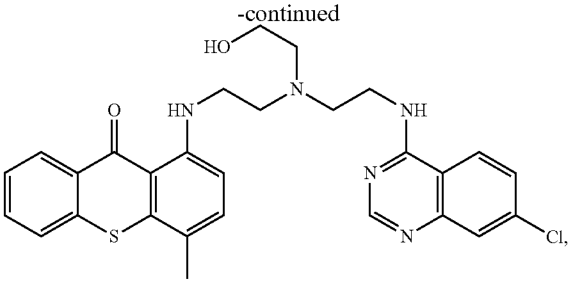
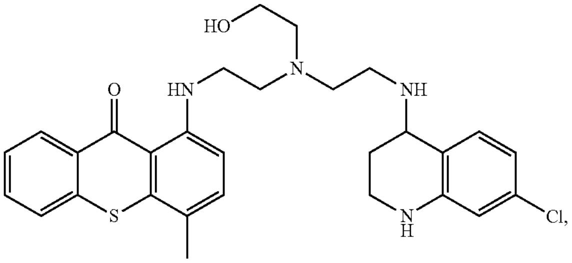
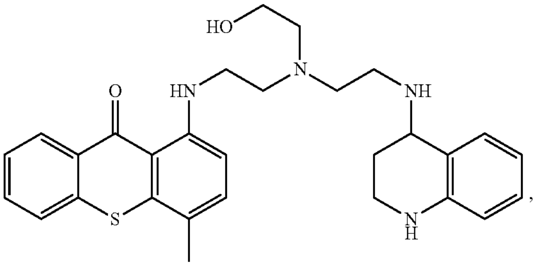
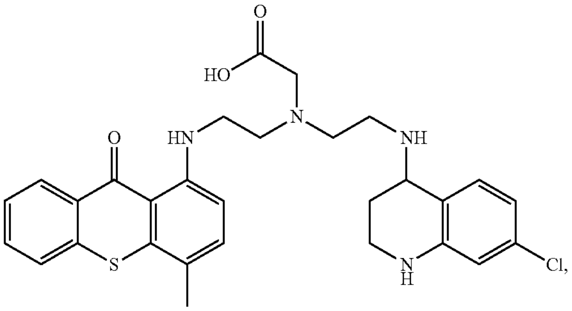
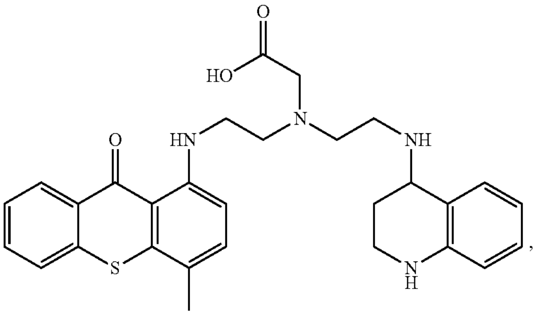
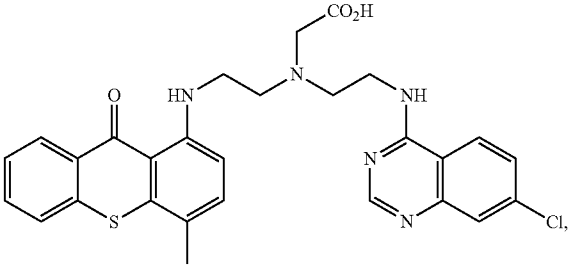
-continued
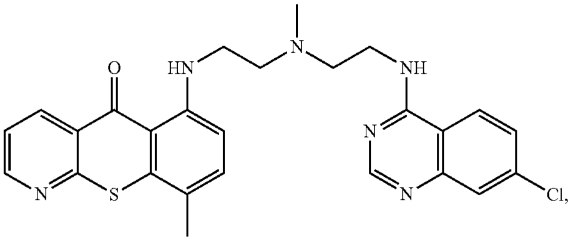
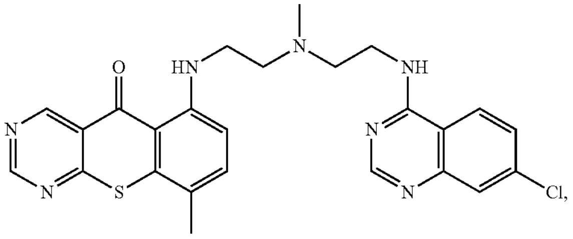
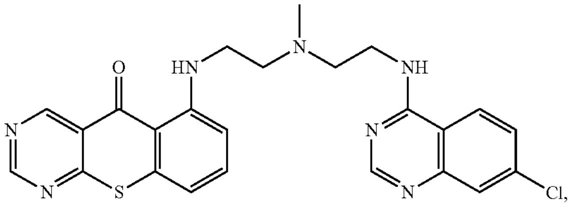
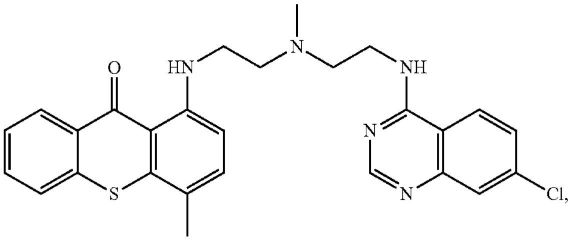
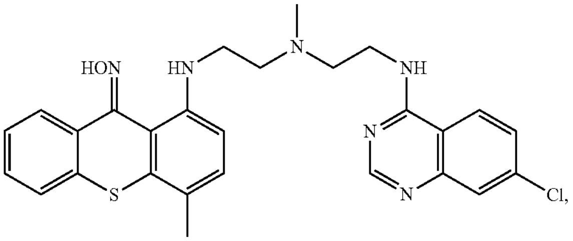
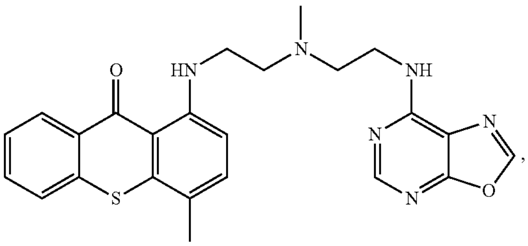
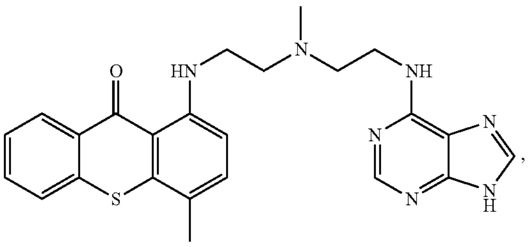

-continued
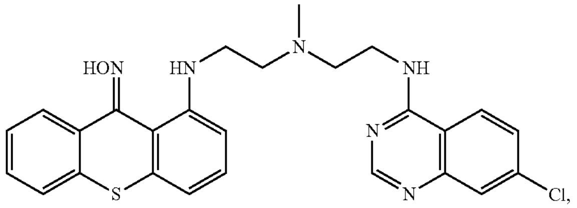
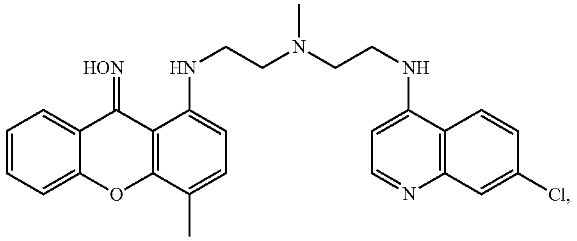
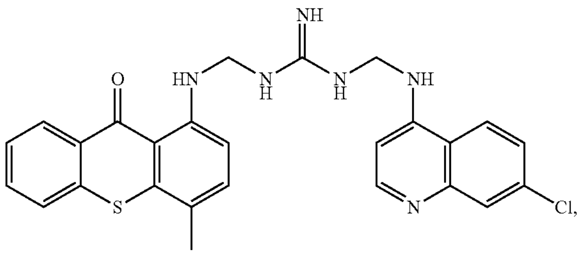
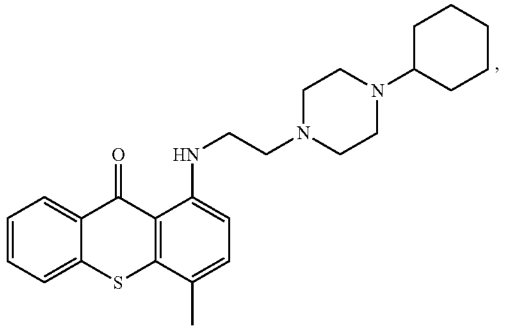
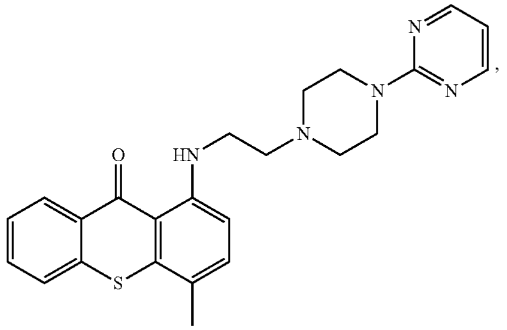
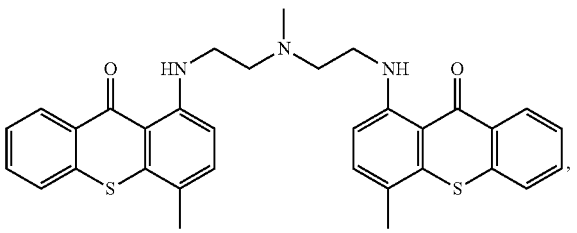
-continued
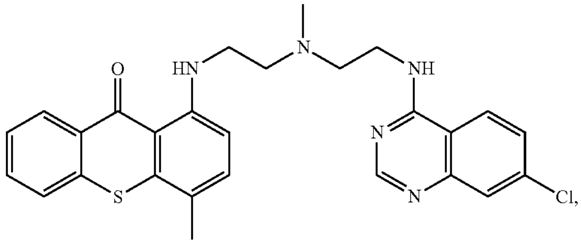
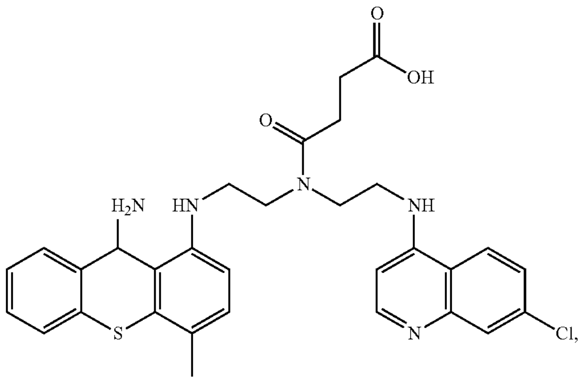
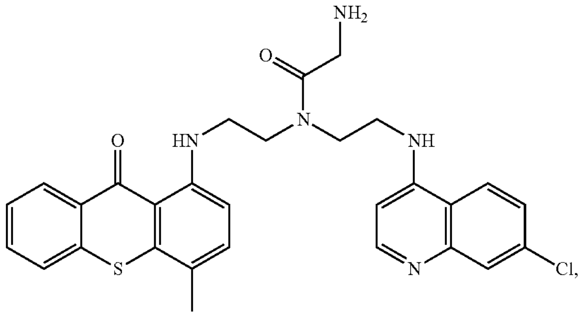
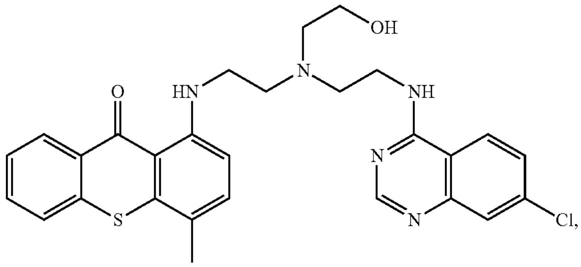
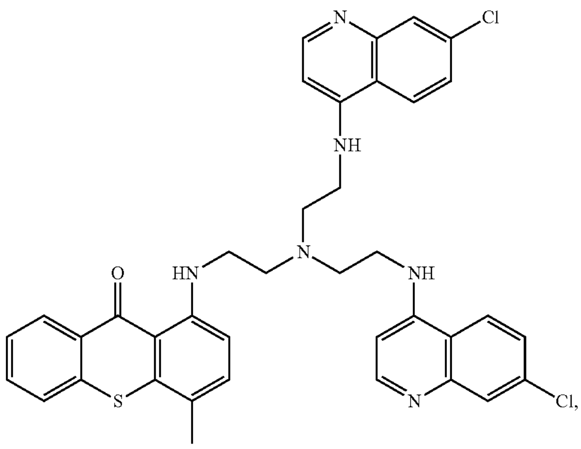

-continued

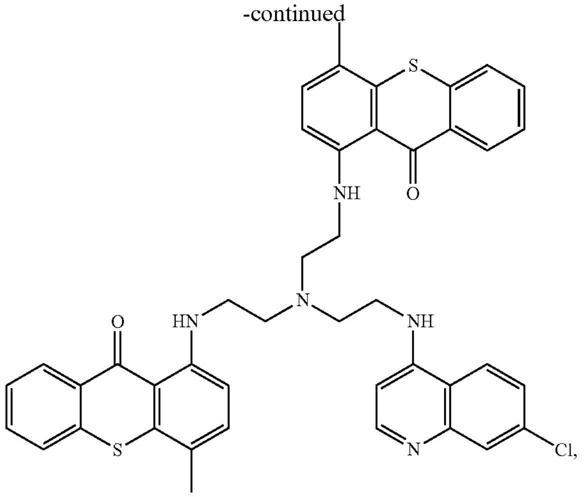

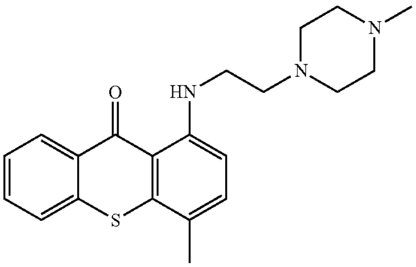

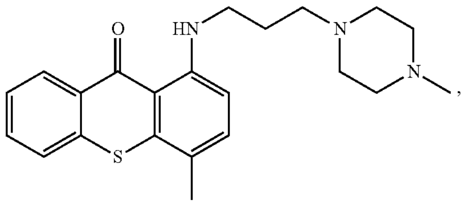

,

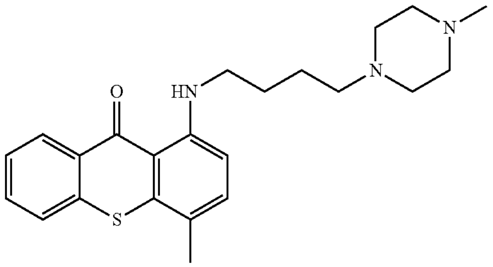

, and

-continued

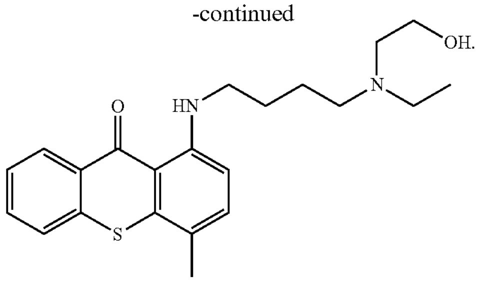

4. A method of treating or ameliorating a disorder related to aberrant cellular autophagy and/or HDAC activity in a patient comprising administering to said patient a therapeutically effective amount of a pharmaceutical composition comprising a compound of claim 1, wherein said disorder is selected from cancer, pulmonary hypertension, diabetes, neurodegenerative disorders, aging, heart disease, rheumatoid arthritis, and infectious diseases.

5. The method of claim 4, wherein said patient is a human patient.

6. The method of claim 4, further comprising administering to said patient one or more agents for treating the disorder.

7. A method for treating, ameliorating and/or preventing symptoms related to viral infection in a subject, comprising administering to the subject a therapeutically effective amount of a pharmaceutical composition comprising a compound of claim 1.

8. The method of claim 7, wherein the symptoms related to viral infection in a subject are one or more of fever, fatigue, dry cough, myalgias, dyspnea, acute respiratory distress syndrome, and pneumonia.

9. The method of claim 7, wherein the subject is a human subject suffering from or at risk of suffering from a condition related to SARS-COV-2 infection.

10. The method of claim 7, wherein the pharmaceutical composition is dispersed in a pharmaceutically acceptable carrier.

11. The method of claim 7, wherein the administering is oral, intravenous, or topical.

12. The method of claim 7, further comprising administering to the subject remdesivir and/or hydroxychloroquine.

* * * * *